United States Patent
Poojary et al.

(10) Patent No.: US 6,933,409 B1
(45) Date of Patent: Aug. 23, 2005

(54) AMINATION OF AROMATIC HYDROCARBONS AND HETEROCYCLIC ANALOGS THEREOF

(75) Inventors: Damodara M. Poojary, Cupertino, CA (US); Ramesh Borade, San Jose, CA (US); Alfred Hagemeyer, Sunnyvale, CA (US); Xiao Ping Zhou, Sunnyvale, CA (US); Christopher E. Dube, Arlington, MA (US); Ulrich Notheis, Dormagen (DE); Ralph Armbrust, Leverkusen (DE); Christian Rasp, Bergisch Gladbach (DE); David M. Lowe, Mountain View, CA (US)

(73) Assignees: Symyx Technologies, Inc., Santa Clara, CA (US); Bayer AG, Leverkusen (DE)

( * ) Notice: Subject to any disclaimer, the term of this patent is extended or adjusted under 35 U.S.C. 154(b) by 0 days.

(21) Appl. No.: 09/571,567

(22) Filed: May 15, 2000

Related U.S. Application Data

(60) Provisional application No. 60/148,057, filed on May 13, 1999.

(51) Int. Cl.$^7$ ............................................. C07C 209/00
(52) U.S. Cl. ........................................ 564/408; 564/395
(58) Field of Search ................................. 564/395, 408

(56) References Cited

U.S. PATENT DOCUMENTS

| | | | |
|---|---|---|---|
| 2,948,755 A | 8/1960 | Schmerling | 260/581 |
| 3,617,507 A | 11/1971 | Oettinger et al. | 208/111 |
| 3,832,364 A | 8/1974 | Coulson | 260/378 |
| 3,919,155 A | 11/1975 | Squire | 260/571 |
| 3,929,889 A | 12/1975 | Squire | 260/571 |
| 3,965,206 A | 6/1976 | Montgomery et al. | 260/669 R |
| 4,001,260 A | 1/1977 | DelPesco | 260/296 R |
| 4,031,106 A | 6/1977 | DelPesco | 260/296 R |
| 4,154,581 A | 5/1979 | Nack et al. | 48/197 R |
| 5,110,113 A | 5/1992 | Kanaya | 271/241 |
| 5,545,602 A | 8/1996 | Nelson et al. | 502/314 |
| 5,861,536 A | 1/1999 | Durante et al. | 564/408 |
| 5,866,737 A | 2/1999 | Hagemeyer et al. | 585/443 |
| 6,204,411 B1 * | 3/2001 | Axon et al. | 564/408 |

FOREIGN PATENT DOCUMENTS

| | | |
|---|---|---|
| CA | 553988 | 3/1958 |
| DE | 196 34 110 A1 | 8/1996 |
| EP | 0 785 177 A2 | 1/1997 |
| GB | 1327494 | 8/1973 |
| GB | 2297043 | 7/1996 |

(Continued)

OTHER PUBLICATIONS

Becker et al. "Amination of benzene in the presence of ammonia using a Group VIII metal supported on a carrier as catalyst" Catalysis Letters, vol. 54 (1998) pp. 125–128.

(Continued)

*Primary Examiner*—Samuel Barts
(74) *Attorney, Agent, or Firm*—Senniger Powers

(57) ABSTRACT

Noble metal/reducible metal oxide catalysts effective for the direct amination of aromatic hydrocarbons and heterocyclic analogs thereof are disclosed. In one embodiment, the cataloxidant comprises a noble metal selected from Pd, Rh, Ir and/or Ru and a reducible metal oxide. In another embodiment, the cataloxidant comprises a noble metal and a reducible oxide of a metal selected from Ni, Mn, V, Ce, Th, Pr, Te, Re, Co, Fe, Cu and/or Bi. A preferred cataloxidant comprises one or more noble metals selected from Pd, Rh, Ir and/or Ru, in combination with nickel oxide and/or manganese oxide. In preferred applications, benzene can be aminated in the presence of the cataloxidants to form aniline. A benzene conversion of at least 5% is achieved, with more than 90% selectivity for aniline. Significantly, the cataloxidant can be regenerated without a substantial loss of performance.

114 Claims, 4 Drawing Sheets

FOREIGN PATENT DOCUMENTS

| | | |
|---|---|---|
| GB | 1463997 | 2/1997 |
| JP | 6-198178 | 7/1994 |
| JP | 6-293715 | 10/1994 |
| JP | 8-206500 | 8/1996 |
| JP | 8-281111 | 10/1996 |
| JP | 9-155364 | 6/1997 |
| JP | 9-220470 | 8/1997 |
| JP | 10-99687 | 4/1998 |
| WO | WO 99/10311 | 3/1999 |
| WO | 00/09473 | 2/2000 |

OTHER PUBLICATIONS

Itoh et al. "Reductive Deamination of Aromatic Amines with Nitric Oxide (NO)$^1$" Tetrahedron Letters, vol. 37, No. 24 (1996) pp. 4165–4168.

Lopez Nieto et al. "Oxidative Dehydrogenation of N–butane and 1–butene on Undoped and K–doped $Vo_x/Al_2O_3$ catalysts" Proceedings ISO'99, Rimini (Italy), Sep. 10–11, 1999. G. Centi and S. Perathoner Ed., SCI Pub. 1999.

Lopez Nieto et al. Oxidative dehydrogenation of n–butane in a two–zone fluid bed reactor Book of Abstracts, 217th ACS National Meeting, Anaheim, CA Mar. 21–25, (1999) (Abstract Only).

Ramos et al. "Oxidation of Hydrocarbons in an in Situ Redox Fluidized Bed Reactor" Journal of Catalysis, vol. 163 (1996) pp. 218–221.

Soler et al. "Oxidative Dehydrogenation of n–Butane in a Two–Zone Fluidized–Bed Reactor" Ind. Eng. Chem. Res., vol. 38, No. 1 (1999) pp. 90–97.

Soler et al. "Oxidative dehydrogenation of n–butane on V/MgO catalysts. Influence of the type of contactor" Catalysis Letters, vol. 50, (1998) pp. 25–30.

A. Hagemeyer notes from Nieto et al. presentation, given at EuropaCat–IV Conference, held in Rimini, Italy from Sept. 5–10, 1999.

* cited by examiner

AMINATION OF AROMATIC HYDROCARBONS AND HETEROCYCLIC ANALOGS THEREOF

REFERENCE TO RELATED APPLICATION

This application claims priority from U.S. provisional application, U.S. Ser. No. 60/148,057, filed on May 13, 1999.

BACKGROUND OF INVENTION

The present invention generally relates to the amination of aromatic compounds and to heterocyclic analogs thereof, and specifically, to the direct, catalytic amination of aromatic compounds and heterocyclic analogs thereof. The invention particularly relates, in a preferred embodiment, to the preparation of aniline directly from benzene and ammonia using heterogeneous catalysts.

Current commercial methods for preparing aromatic amines such as aniline involve multiple reaction steps. For example, aniline is typically prepared by converting benzene to a derivative, such as nitrobenzene, phenol or, chlorobenzene, and then converting the derivative to aniline. Such indirect methods, summarized in U.S. Pat. No. 5,861,536 to Durante et al., have long been recognized as less than optimal with respect to corrosive material handling, environmental and/or feedstock cost concerns.

Alternative methods for preparing aromatic amines directly from aromatic hydrocarbons have been reported in the art. For example, aniline can be produced by direct amination of benzene according to Reaction I:

Reaction I

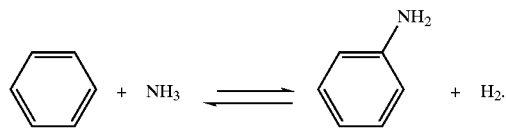

Reaction I is, however, thermodynamically disfavored in the forward direction at reasonable temperatures and pressures. Approaches have been proposed, therefore, to react the hydrogen produced in Reaction I with oxygen to form water, thereby driving the thermodynamic equilibrium in the forward direction, and improving the conversion of benzene to aniline. The overall reaction according to this approach is represented by Reaction II:

Reaction II

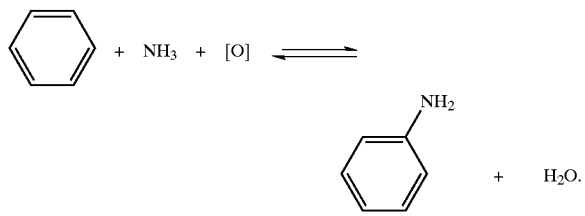

Canadian patent No. 553,988 to Thomas et al. proposed two distinct embodiments for effecting the approach involving Reaction II. In a first embodiment, Thomas et al. disclose effecting the reaction by contacting benzene, ammonia and gaseous oxygen with a platinum catalyst maintained at a temperature of about 1000° C. Platinum-containing catalysts effective for use in connection with this first embodiment are reported to include, independently, platinum alone, platinum alloyed with certain specifically-recited metals, and platinum combined with certain specifically-recited metal oxides. In a second, independent embodiment, Thomas et al. disclose effecting Reaction II by contacting benzene and ammonia in the vapor phase with a reducible metal oxide at a temperature of from about 100° C. to about 1000° C., without supplying gaseous oxygen to the reaction. The reducible metal oxides said to be suitable for use in connection with this second embodiment include oxides of Fe, Ni, Co, Sn, Sb, Bi and Cu.

Other processes for the direct amination of benzene and other aromatic hydrocarbons have also involved catalysts comprising a reducible metal oxide—with or without also supplying gaseous oxygen to the reactor. U.S. Pat. No. 2,948,755 to Schmerling, for example, describes an approach for effecting Reaction II in which benzene and ammonia, and optionally gaseous oxygen, are reacted in the presence of a catalyst comprising a reducible metal oxide in combination with, independently, molybdenum, tungsten or chromium. U.S. Pat. Nos. 3,919,155 and 3,929,889 to Squire, and U.S. Pat. Nos. 4,001,260 and 4,031,106 to Del Pesco, disclose reacting benzene and ammonia in the presence of a nickel/nickel oxide cataloreactant for effecting Reaction II.

A number of processes for the direct amination of benzene and other aromatic hydrocarbons have also involved catalysts comprising noble metals. Recently, for example, Becker et al. reported the preparation of aniline by reaction of benzene and ammonia with a gaseous oxygen or carbon monoxide co-feed in a plug-flow or continuous-stirred-tank reactor over a Group VIII-metal catalyst. Specific catalysts consisted of, independently, Pd, Pt, Ru, Rh and Ni supported on alumina, and for one experiment, CuO supported on zirconium oxide. (See Becker et al., *Amination of Benzene in the Presence of Ammonia Using a Group VIII Metal Supported on a Carrier as a Catalyst,* Cat. Let. 54, 124–128 (1998).) The published German patent application DE 19634110 A1 of Hölderich et al. discloses direct amination of benzene with catalysts comprising, independently, Pd, Pt, Rh and Ru. U.S. Pat. No. 5,861,536 to Durante et al. discloses direct oxidative amination of benzene using a supported catalyst comprising a transition metal and a mono- or bi-nucleating ligand. In one example, catalysts comprising palladium with and without a nitroso-group ligand are compared. Axon at al. report, in PCT application WO 99/10311, the reaction of benzene, ammonia and gaseous oxygen in the presence of a catalyst comprising transition metals, lanthanides and actinides, with specific examples involving, independently, a Pt/rh gauze, Pt supported on silica, Pt supported on alumina and V supported on alumina.

The reported approaches for the direct, single-step amination of benzene to aniline have not been adopted commercially. These approaches generally suffer from relatively low benzene conversion and/or relatively low selectivity for aniline. Moreover, the reported catalyst systems involving a metal-oxide cataloreactant are not sufficiently regenerable for commercial viability; that is, such known catalysts do not maintain commercially acceptable benzene conversion and/or aniline selectivity for a commercially-attractive number of cycles. Hence, there remains a need in the art for a commercially viable heterogeneous catalyst and process for the direct amination of benzene and other aromatic compounds or heterocyclic analogs thereof to the corresponding amino compounds.

SUMMARY OF INVENTION

It is therefore an object of the present invention to provide improved heterogeneous catalysts and improved protocols for aminating substituted or unsubstituted aromatic compounds or heterocyclic analogs thereof. In particular, it is an object of the invention to effect such aminations with relatively high levels of conversion and with commercially acceptable selectivities for the desired arylamine or heteroarylamine products. It is likewise an object of the invention to provide catalysts and amination processes that are commercially viable.

Briefly, therefore, the present invention is directed to methods for preparing arylamines or heteroaryl amines. An aromatic hydrocarbon (e.g., benzene) or a heterocyclic analog thereof (e.g., pyridine) is reacted with an aminating agent (e.g., ammonia) over a heterogeneous catalyst.

In one embodiment, the catalyst comprises a noble metal selected from Pd, Rh, Ir and/or Ru and a reducible metal oxide.

In another embodiment, the catalyst comprises a noble metal and a reducible oxide of a metal selected from Ni, Mn, V, Ce, Th, Pr, Te, Re, Co, Fe, Cu and/or Bi.

In an additional embodiment, the catalyst comprises one or more noble metals selected from Pd, Pt, Rh, Ir, Ru and/or Os, and one or more reducible oxides of a metal selected from Ni, Mn, V, Ce, Th, Pr, Te, Re, Co, Fe, Cu and/or Bi.

In a further embodiment, the catalyst comprises a noble metal, a first metal oxide and a second metal oxide. The first metal oxide is a reducible metal oxide. The second metal oxide is an oxide of an alkali metal, an alkaline earth metal, a rare earth metal or a selected metal chosen from among Ga, Al, Y, Co, Mo, Cr, Mn, Zn, In, Fe, Bi, Sb or V. The second metal oxide is, in a preferred case, a dopant metal oxide.

In a preferred embodiment, the catalyst is a supported catalyst and comprises a noble metal and nickel oxide. The noble metal can be selected from Pd, Pt, Rh, Ir and Ru, and is preferably selected from Pd, Rh, Ir and Ru. In some cases, Rh and Ir are particularly preferred noble metals. Nickel oxide can be employed as the reducible metal oxide component alone, or can be employed in combination with other metal oxides, of which manganese oxide is preferred.

The invention is directed, moreover, to methods for preparing aniline by direct amination of benzene with ammonia in the presence of the catalyst. The catalyst can be any of the aforementioned catalysts.

According to one process embodiment, benzene and ammonia are reacted in a reaction zone of a reactor without providing an oxygen co-feed (or any co-feed comprising an oxygen-containing gas such as air); that is, benzene and ammonia are reacted without supplying a feed-line to supply an oxygen-containing gas to the reaction zone.

In another process embodiment, the catalyst (or at least a portion thereof) can be regenerated by oxidation (e.g., calcination), after deactivation in a catalyst run, and thereafter used in a series of successive catalyst runs between which the catalyst is again regenerated, up to a total of at least five regeneration cycles (i.e., at least six catalyst runs), without substantial reduction in benzene conversion from run to run and with at least about 90% selectivity for aniline based on weight and relative to benzene in each run. The substantially stable benzene conversion for the six or more amination reactions can be characterized by a difference in the benzene conversion for the initial amination reaction (with fresh catalyst) versus the benzene conversion for the amination reaction over the 5-time-regenerated catalyst, with such difference being less than about 50 %, and preferably even smaller (e.g., less than about 25%, less than about 10%, or less than about 5%).

In another process embodiment, the catalyst (or at least a portion thereof) is regenerated by oxidation, but without a separate reduction step. Specifically, the catalyst is exposed to oxidizing conditions to oxidize the metal (or lower oxidation state metal oxide), without exposing the catalyst to reducing conditions during the regeneration protocol. Any noble-metal oxides formed during regeneration arc effectively reduced in situ during the next amination reaction.

The invention is directed, as well, to catalyst compositions, and to methods for preparing the catalyst compositions. The catalyst compositions are generally characterized as described above. In a preferred embodiment, the catalyst composition comprises a noble metal component in an amount ranging from about 0.05% to about 5% by weight relative to total weight of the catalyst, nickel oxide ranging from about 5% to about 50%, and preferably from about 5% to about 30%, in each case by weight relative to total weight of the catalyst, manganese oxide and a support (i.e., a carrier). Manganese is preferably present in an amount ranging from about 0.5% to about 30% and more preferably from about 0.5% to about 20%, while in some cases it ranges from about 0.5% to about 3% and in others from about 10% to about by 20%, in each case by weight relative to total weight of the catalyst.

The invention is further directed to an unsupported, bulk catalyst composition comprising a noble metal component in an amount ranging from about 0.5% to about 5% by weight relative to the total weight of the catalyst, nickel oxide, with the amount of nickel ranging from about 30% to about 90%, and preferably from about 40% to about 80%, in each case by weight relative to the total weight of the catalyst, and a binder in an amount ranging from about 10% to about 20%, based on the total weight of the catalyst. Hence, the catalysts and processes of the present invention offer commercially meaningful advantages over the prior art. In particular, the catalysts and processes of the invention can be employed to prepare aromatic amines and heterocyclic analogs thereof with reproducible, commercially attractive yields. Moreover, such attractive yields can be substantially achieved even after numerous catalyst regeneration cycles. These performance advantages, coupled with efficient, controllable regeneration protocols, demonstrate the commercial potential for the catalysts and processes of the present invention. Additionally, the catalysts of the present invention are compatible with commercial catalyst-preparation and reaction protocols.

The catalysts and processes of the present invention can be used to prepare a number of important chemical intermediates, including, for example, aniline, 4-aminodiphenylamine (4-ADPA), methyldianiline and toluenediimine. Aniline is a commodity chemical useful as an intermediate for the production of many commercially-important materials, including isocyanates, polyurethanes, dyes, pigments, photochemicals, rubber chemicals, specialty fibers, oxidation-inhibiting additives, pesticides and pharmaceuticals, among others.

Other features, objects and advantages of the present invention will be in part apparent to those skilled in art and in part pointed out hereinafter. All patents and literature references cited in the instant specification are hereby incorporated by reference for all purposes. Moreover, as the patent and non-patent literature relating to the subject matter disclosed and/or claimed herein is substantial, many relevant references are available to a skilled artisan that will provide further instruction with respect to such subject matter.

The invention is described in further detail below with reference to the figures.

DETAILED DESCRIPTION OF THE INVENTION

Figure 1:
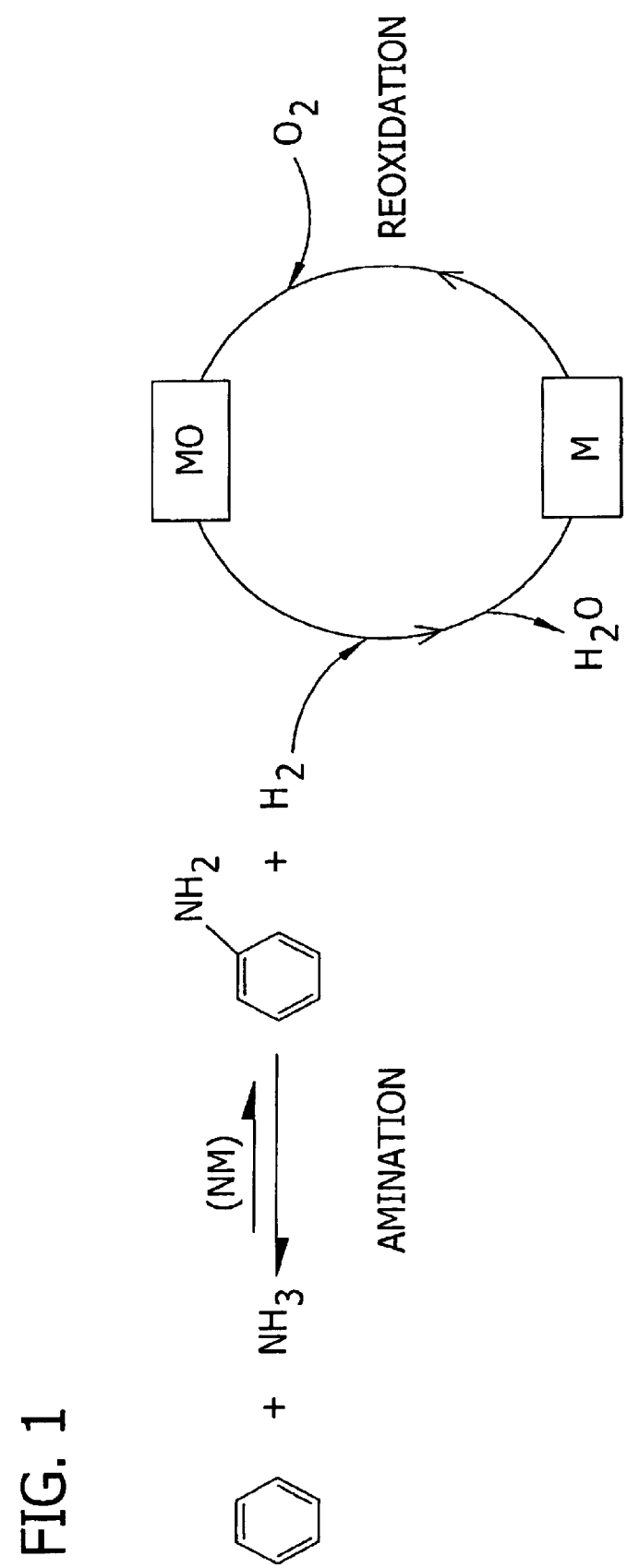
FIG. 1 is a schematic representation of an exemplary amination reaction, in which benzene is reacted with ammonia in the presence of a catalyst comprising a noble metal (NM) and a reducible metal oxide (MO) to form aniline. The metal oxide is reduced by hydrogen from the amination reaction, and can be regenerated by oxidation with, for example, molecular oxygen.

In the present invention, a substituted or unsubstituted arylamine or a substituted or unsubstituted heteroarylamine is prepared by direct catalytic amination of the corresponding aromatic compound or heterocyclic analog thereof. In a preferred application, benzene is aminated in the presence of a heterogeneous catalyst to form aniline. The catalyst generally comprises a noble metal component and a reducible metal oxide component. Without being bound by theory, and with reference to FIG. 1, the noble metal (NM) component catalyzes the amination reaction (Reaction I, above), and the reducible metal oxide (MO) component oxidizes hydrogen produced by the amination reaction to form water and a metal (M) (or a metal oxide in a lower oxidation state), such that the overall reaction proceeds according to Reaction II (above). Hence, the catalyst of the present invention can be aptly referred to as a cataloxidant.

Combinatorial materials science approaches have been employed to identify useful noble metal/reducible metal oxide cataloxidants, and specifically, to identify noble metal components, reducible metal oxide components, and combinations thereof that are advantageous with respect to reactant conversion, product selectivity and catalyst regenerability. Additional components, such as dopant metal oxides, have also been identified as being advantageous with respect to performance and regenerability. As such, a number of advantageously useful noble metal/reducible metal oxide cataloxidants have been discovered for the aforementioned amination reactions.

Cataloxidants

It is to be noted that, as used herein, the terms "catalyst," "cataloxidant" and "cataloreactant" are intended to refer to the compositions of the present invention; that is, each term may be used interchangeably herein to refer to compositions which act to catalyze, and which are consumed by, the present process.

The noble metal component of the cataloxidant of the present invention comprises, in the general case, one or more noble metals having catalytic activity for the amination of the aromatic compound or heterocyclic analog of interest. The noble metal component preferably generally comprises Pd, Pt, Rh, Ir, Ru and/or Os. In some embodiments, the noble metal component preferably comprises Pd, Rh, Ir and/or Ru. Moreover, as discussed below, each of the preferred noble metals may be specifically preferred for particular reactions and/or for particular reaction conditions. The noble metal component can consist essentially of one of the noble metals, or alternatively, can comprise two or more noble metals (e.g., as an alloy of two or more noble metals). When the noble metal component comprises a combination of noble metals, at least one of the noble metals can have catalytic activity for the amination reaction, the other noble metal(s) employed in combination therewith can also be catalytically active or can be inert (e.g., Au, Ag), the inert noble metal simply acting to increase the dispersion or physical separation of the noble metal particles present. Hence, the noble metal component can comprise, for example, two or more of the noble metals Au, Ag, Pd, Pt, Rh, Ir and/or Ru, or in some preferred embodiments, two or more of the noble metals Au, Pd, Rh, Ir and/or Ru. In some cases in which the noble metal components comprise two or more noble metals, more than about 50% of the noble metal component can consist essentially of only one of the noble metals. In other such cases, at least about 55%, at least about 60%, at least about 75%, or at least about 90% of the noble metal component can consist essentially of one of the noble metals. While the foregoing general preferences have been recited in terms of particular groupings of noble metals, it is to be understood that such preferences may include individually-recited members of such groups as well as any and all possible subsets of such groups, depending on the particular reaction for which the cataloxidant is being applied and on the particular reaction conditions employed.

The reducible metal oxide component of the cataloxidant of the present invention comprises, in the general case, a metal oxide that is reduced to a lower oxidation state when exposed to hydrogen at a temperature of about 200° C. or greater, and preferably at a temperature ranging from about 200° C. to about 50° C. As discussed in greater detail below, certain reducible metal oxides have been discovered as being advantageous for use with a noble metal to form a composition suitable for use as a cataloxidant for the amination of aromatic compounds such as aniline. Specifically, the reducible metal oxide component preferably comprises an oxide of one or more of the following metals: Ni, Mn, V, Ce, Th, Pr, Te, Re, Co, Fe, Cu and/or Bi. The reducible metal oxide component more preferably comprises an oxide of one or more of Ni, Mn, Ce and/or Co, even more preferably comprises an oxide of nickel or an oxide of manganese, and most preferably comprises an oxide of nickel (e.g., NiO). The reducible metal oxide component can consist essentially of an oxide of one of the aforementioned metals, such as for example, an oxide of Ni or an oxide of Mn. In some cases, the reducible metal oxide component can, alternatively, comprise reducible oxides of two or more metals. In such cases, at least one of the reducible metal oxides is preferably a metal selected from Ni, Mn, V, Ce, Tb, Pr, Te, Re, Co, Fe, Cu and/or Bi. Two of the two or more reducible metal oxides can also be selected from the immediately-preceding lists of preferred metal oxides. In some preferred embodiments, the reducible metal oxide component of the cataloxidant comprises an oxide of Ni and an oxide of Mn, and in some cases, the reducible metal oxide component can consist essentially of an oxide of Ni and an oxide of Mn. While the foregoing general preferences have been recited in terms of particular groupings of reducible metal oxides, it is to be understood that such preferences may include individually-recited members of such groups as well as any and all possible subsets of such groups, depending on the particular reaction for which the cataloxidant is being applied and on the particular reaction conditions employed.

According to the present invention, certain noble metal/reducible metal oxide catalysts have been found to be particularly effective for the direct amination of aromatic hydrocarbons and heterocyclic analogs thereof. In a first generally preferred embodiment, the cataloxidant of the invention comprises a noble metal selected from Pd, Rh, Ir and/or Ru and a reducible metal oxide. In a second generally preferred embodiment, the cataloxidant of the invention comprises a noble metal and a reducible oxide of a metal selected from Ni, Mn, V, Ce, Th, Pr, Te, Re, Co, Fe, Cu and/or Bi. In a third generally preferred embodiment, the preferred noble metals and preferred reducible metal oxides are employed in combination (including all various permutations and combinations thereof), such that the cataloxidant comprises one or more noble metals selected from Pd, Pt, Rh, Ir, Ru and/or Os, and one or more reducible oxides of a metal selected from Ni, Mn, V, Ce, Th, Pr, Te, Re, Co, Fe, Cu and/or Bi.

The particular noble metal/reducible metal oxide catalysts included within the immediately aforementioned generally preferred embodiments are distinguished from the noble metal/reducible metal oxide catalysts known in the art for the amination reactions of interest, particularly from those disclosed in Canadian patent No. 553,988 to Thomas et al. As noted above, Thomas et al. report that benzene, aniline and gaseous oxygen can be reacted at 1000° C. in the presence of a catalyst comprising Pt in individual combination with oxides of Cr, Mo, W or Nb. In contrast, the preferred cataloxidants of the present invention employ a different noble metal component and/or a different reducible metal oxide component. In the first generally preferred embodiment, for example, Pd, Rh, Ir and/or Ru are employed in the noble metal component rather than Pt. Significantly, it has been discovered that Pd, Rh, Ir and Ru are each advantageous over Pt with respect to regenerability of the cataloxidant. It has been discovered that catalysts consisting essentially of platinum and oxides of, independently, Cr, Mo, W or Nb, are not suitably regenerable under the oxidizing conditions that would be required for commercial regeneration. Without being bound by theory, the platinum catalyst particles tend to agglomerate and fuse under such oxidative regeneration conditions, resulting in a reduction of catalyst activity, and a corresponding reduction in desired product (e.g., aniline) yield. However, cataloxidants comprising Pd, Rh, Ir and/or Ru as the noble metal in combination with a reducible metal oxide can be satisfactorily regenerated. In the second generally preferred embodiment, the reducible metal oxide component comprises an oxide of a metal other than Cr, Mo, W and Nb—preferably an oxide one or more of the following metals: Ni, Mn, V, Ce, Th, Pr, Te, Re, Co, Fe, Cu and/or Bi. Significantly, when employed in combination with a noble metal, these reducible metal oxides form a cataloxidant that provides for better conversion of the aromatic compound (e.g., benzene) and better selectivity for the desired product (e.g., aniline) than the reducible metal oxides disclosed in Thomas et al. Without being bound by theory, the reducible metal oxides of the invention can form a complex with the ammonia or other aminating agent, with the strength of complex being appropriate to achieve substantial aniline selectivity for the temperature ranges of interest. In the third generally preferred embodiment, the cataloxidant is advantageous over the prior art noble metal/reducible metal oxide cataloxidants with respect to both performance and regenerability.

The relative amount of the noble metal component and the reducible metal oxide component in the cataloxidant is not narrowly critical, and can vary with the particular reaction being effected, with the form of the cataloxidant (e.g., support material, surface area), with the reaction conditions (e.g., temperature, pressure, ratio of reactants, ratio of reactants:catalyst), and/or with regenerability requirements. In general, however, the catalyst preferably comprises an amount of noble metal component ranging from about 0.01% to about 10%, more preferably ranging from about 0.05% to about 5%, in some cases even more preferably ranging from about 0.1% to about 5%, or still more preferably ranging from about 0.15% to about 3%, in each case the percentages being by weight relative to the total weight of the catalyst.

The catalyst preferably comprises a reducible metal oxide component in an amount ranging from about 5% to about 99.99%, and more preferably ranging from about 5% to about 75%, in each case by weight relative to the total weight of the catalyst. The reducible metal oxide component even more preferably range, particularly where the catalyst is a supported catalyst, from about 5% to about 50%, still more preferably from about 5% to about 30%, or from about 5% to about 20%, in each case by weight relative to the total weight of the catalyst. In those cases where the catalyst is unsupported, bulk catalysts, with small fractions of binders (such as, for example, silica or alumina, used to impart mechanical strength to the catalyst), the reducible metal oxide component preferably ranges from about 30% to about 90% and more preferably from about 40% to about 80%, in each case by weight relative to the total weight of the catalyst.

With regard to the unsupported catalysts, it is to be noted that these may include, among others, bulk nickel, cobalt or copper catalysts (which are commercially available). Generally speaking, these catalysts differ from supported catalyst in that they are prepared by means of precipitation, rather than impregnation. Accordingly, unlike the latter, in which metal loading is dependent upon pore volume, essentially any amount of metal may be incorporated into the unsupported catalysts. Unsupported catalysts preferably have surface areas ranging from about 30 $m^2/g$ to about 150 $m^2/g$, with surface areas ranging from about 50 $m^2/g$ to about 100 $m^2/g$ being even more preferred. Regenerability of the catalyst can, for at least some reducible metal oxides (e.g., NiO) and for at least the supported catalysts, be favored with catalyst compositions ranging from about 5% to about 50% by weight relative to total weight of the catalyst. The above-recited ranges for the noble metal component and for the reducible metal oxide component can be combined in any of the various combinations and permutations. Other, more specific ranges for preferred catalyst compositions are discussed below. Expressed in terms of molar ratios, the relative molar amount of noble metal component to reducible metal oxide component (i.e., the "NM:RMO") can, independently of the aforementioned weight percentages, range from about 1:25,000 to about 1:1, preferably from about 1:5,000 to about 1:2, and in some cases from about 1:1000 to about 1:3 or from about 1:100 to about 1:4. As discussed below, the reducible metal oxide component of the cataloxidant can be supplied to the reactor as a metal-oxide precursor (e.g., as a metal or lower-oxidation state oxide) and then be oxidized (e.g., calcined)

to form the reducible metal oxides. In such cases, the molar ratio of the noble metal component to the reducible metal-oxide precursor (i.e., the "NM:RMOP") can, independent of the aforementioned weight percentages and independent of the aforementioned NM:RMO ratios, range from about 1:25,000 to about 1: 1, preferably from about 1:5,000 to about 1:2, and in some cases from about 1:1000 to about 1:3 or from about 1:100 to about 1:4.

In this regard it is to be noted that, regardless of the way in which the metal oxides are formed, preferably when used in the dehydrogenation reaction most of the metal atoms (i.e., about 50%, 70%, 90% or more) will be present in an oxidized state, preferably in the form of the following oxidation states: $Ni^{+2}$; $V^{+5}$; $Fe^{+3}$; $Co^{+2}$ or $Co^{+3}$ (or some combination thereof); $Cu^{+2}$; $Mn^{+2}$, $Mn^{+3}$ or $Mn^{+4}$ (or some combination thereof); $Ce^{+4}$; $Bi^{+3}$; $Pr^{+4}$; $Tb^{+3}$ or $Th^{+4}$ (or some combination thereof); $Te^{+4}$ or $Te^{+6}$ (or some combination thereof); and, $Re^{+4}$, $Re^{+6}$ or $Re^{+7}$ (or some combination thereof).

The catatoxidant of the invention can further comprise a second metal oxide component, in addition to the reducible metal oxide component. The second metal oxide component is considered to be a dopant and, as such, is alternatively referred to herein as a dopant oxide component. The second (dopant) metal oxide component can comprise an oxide of a metal selected from the alkali metals (e.g., Li, Na, K and Cs), the alkaline earth metals (e.g., Mg, Ca, St, Ba), the rare earth metals (e.g., La, Ce, Pr, Nd, Pm, Sm, Eu, Gd, Th, Dy, Ho, Er, Tm and Yb), and certain other specific selected metals, such other selected metals consisting exclusively of Ga, Al, Y, Co, Mo, Cr, Mn, Zn, In, Fe, Bi, Sb, Cu, Ag and/or V. The second metal oxide component preferably comprises an oxide of Ga, Al, Y, Co, Cr and/or Mn. Manganese oxide is a generally preferred second (dopant) metal oxide. The second metal oxide component can consist essentially of one of the aforementioned metal oxides, or alternatively, can comprise two or more of the aforementioned metal oxides in combination. Hence, in another (fourth) generally preferred embodiment of the invention, the catalyst of the present invention comprises a noble metal, a (first) reducible metal oxide, and a (second) dopant metal oxide that is different from the first metal oxide. The second metal oxide component can also be employed as a further component of the previously discussed first, second and third generally preferred embodiments. Without being bound by theory (including, without limiting the equivalents of a dopant oxide component where such component is specifically required in the claims) the dopant metal oxide component appears to improve and/or maintain the dispersion of noble metal and/or reducible metal oxide on the support or carrier, particularly after regeneration. The dopant metal oxide component can also improve electron or oxygen ion conductivity of the catalyst material and, as such, can lead to higher solid oxidant efficiencies. Hence, the dopant oxide component can be important for some catatoxidants of the invention with respect to regenerability thereof. Moreover, some dopant metal oxides, such as oxides of alkali metals or oxides of alkaline earth metals, can increase the basicity of the cataloxidant and, as such, help reduce ammonia adsorption to the catalyst and ultimately reduce ammonia decomposition. In addition, the alkali and alkaline oxide dopants also help to "disrobe" aniline from the catalyst surface.

The relative amount of the dopant oxide component can range from about 0.05% to about 30%, more preferably from about 0.05% to about 20%, and even more preferably from about 0.1% to about 10%, in each case by weight relative to total weight of the catalyst. In some embodiments, the amount of dopant oxide component can preferably range from about 0.1% to about 5% and, in some cases, from about 0.5% to about 5%, from about 1% to about 5%, or from about 2% to about 5%, in each case by weight relative to total weight of the catalyst. The above-recited weight-based ranges for the dopant oxide component can be combined in any combination and permutation with the previously recited ranges for the noble metal component and for the reducible metal oxide component. Expressed in terms of molar ratios, the relative molar amount of noble metal component to second (dopant) oxide component (i.e., the "NM:DMO") can, independently of the aforementioned weight percentages, range from about 1:1000 to about 250:1, preferably from about 1:200 to about 10:1, and in some cases from about 1:100 to about 5:1. As discussed below, the dopant metal oxide component of the catatoxidant can be supplied to the reactor as a metal-oxide precursor (e.g., as a metal or lower-oxidation state oxide) and then be oxidized (e.g., calcined) to form the dopant metal oxide. In such cases, the molar ratio of the noble metal component to the dopant metal-oxide precursor (i.e., the "NM:DMOP") can, independent of the aforementioned weight percentages and independent of the aforementioned NM:DMO ratios, range from about 1:2000 to about 250:1, preferably from about 1:400 to about 10:1, and in some cases from about 1:200 to out 5:1.

Some of the metal oxides disclosed as suitable for inclusion in the reducible metal oxide component of the catalyst (i.e., Mn, V, Ce, Th, Pr, Co and Bi) are also suitable for inclusion in the dopant oxide component of the catalyst. Without being bound by theory, such commonly-included oxides (e.g., manganese oxides) can have both oxidizing and phase-stabilizing/oxygen-ion conductivity enhancing functions. When such a particular metal oxide common to each of such components is employed in a catalyst, however, its characterization as to whether that particular metal oxide is serving as a reducible metal oxide or as a dopant oxide is not to be considered as limiting to the scope of the invention as claimed, or equivalents thereof. It is recognized, nonetheless, that such characterization may be necessary for evaluating the catalyst with regard to claims that require particular relative amounts of reducible metal oxide components and/or of second (dopant) oxide components. In such cases, for purposes of evaluating the relative amounts of components in a catalyst composition (and without being limited as to the function of such an included metal oxide), a common metal oxide (e.g., Mn) can be considered to be a part of the reducible metal oxide component if it is present in the catalyst in a proportion of 5% or greater by weight relative to the total weight of the catalyst. Such a common metal oxide can be considered to be a part of the second (dopant) metal oxide component if it is present in the catalyst in a proportion of less than 5% by weight relative to the total weight of the catalyst.

The catatoxidants of the present invention are employed in commercial applications as solid materials, typically with gaseous and/or liquid reactants. As such, the catatoxidants of the present invention are heterogeneous catalysts. However, the particular physical form of the catalysts (including the degree of crystallinity or the particular crystalline structure) may vary substantially and is not generally of critical significance. Moreover, the catatoxidants disclosed and claimed herein can be employed as supported or unsupported catalysts.

The catalysts of the present invention are preferably supported. The particular support material and/or form is not, however, generally critical and selection of support material and/or form can be effected for a particular cataloxidant according to approaches known in the art. The supports can include any suitable inert and stable support material. The support can comprise, for example, zirconium dioxide, titanium dioxide, alumina, tantalum oxide, niobium oxide, silica, diatomaceous earth and zeolites among other materials. Zirconium dioxide (e.g., Norton Chemical Products Corp.) and titanium dioxide (e.g., Norton Chemical Products Corp.; Degussa) are preferred supports for some embodiments. The supports are, in general, preferably porous, having a porosity, pore structure, pore size distribution, pore volume and surface area suitable to provide substantial dispersion of the noble metal component and/or the metal oxide component. Improving the dispersion of noble metal component and/or metal oxide component can favorably affect the regenerability of the cataloxidant. In the general case, typical support surface areas can range from about 1 $m^2/g$ to about 300 $m^2/g$, and more typically from about 10 $m^2/g$ to about 150 $m^2/g$, with a surface area of about 50 $m^2/g$ being appropriate in some applications. Additionally, the pore volume of these supports typically ranges from about 0.2 cc/g to about 1 cc/g, and more typically from about 0.3 cc/g to about 0.7 cc/g. The mechanical stability of the supports should preferably be sufficient to retain structural integrity thereof after repeated cycles of catalyst regeneration. The shape and size of the support material are not critical, and can include the many variations known in the art, including, for example, monoliths, cylinders, tablets, pellets, granules, corrugated sheets, shaped-extrudates, etc. The particular shape and/or particle size can vary, for example, depending upon the reactor and/or process configuration to be employed.

In this regard it is to be noted that, generally speaking, once the support has been "loaded" with the typical amount of noble metal, metal oxide, etc. (i.e., once the noble metal, metal oxide, etc. have been adsorbed onto and/or absorbed into the support), the pore volume may decrease by about 2% to about 30%, while the surface area may also decrease by about 2% to about 30%.

The supports can be modified and/or pretreated with various agents to facilitate catalyst preparation, to improve mechanical properties of the support and/or to improve the performance characteristics and/or regenerability of the catalyst. The support can, for example, be modified with respect to acidity/basicity. For the amination reaction with ammonia, the supports are preferably neutral or slightly basic (ie., non-acidic) to reduce the preference for ammonia adsorption. Hence, an acidic support material (e.g. titanium dioxide, alumina, silica) can be impregnated with a neutralizing amount of an alkali metal oxide or an alkaline earth metal oxide, such as oxides of potassium, lithium, sodium, rubidium, magnesium, calcium, barium, cesium or strontium. For benzene amination with ammonia, therefore, preferred support materials include the relatively neutral zirconium dioxide, as well as alkali-oxide-doped or alkaline-earth-oxide-doped (e.g., potassium-impregnated) titanium dioxide. As noted above, such alkali metal oxides or alkaline-earth metal oxides can be considered to be a dopant oxide component of the cataloxidant. As such, and as discussed in greater detail below, such dopant oxides can be integrated with the other cataloxidant components, particularly in terms of catalyst preparation. Alternatively, such dopant oxides can be prepared as a modified support onto which the other catalyst components are subsequently added. It may be preferable for some catalysts and for some reactions to modify the support to form the oxide-doped support prior to preparation of the catalyst thereon, because different calcination conditions can be employed independent of the catalyst components and/or precursors thereof. Such an approach can, in some cases, result in a preferred crystalline structure for the support than would otherwise be achieved if the doping alkali or alkaline earth metal oxide were prepared as part of the general catalyst preparation steps outlined below. An oxide-doped support can be prepared, for example, by impregnating the support with an alkali metal or an alkaline earth metal in an amount ranging from about 0.1% to about 10%, from about 0.5% to about 7.5%, or from about 1% to about 5% by weight, relative to total weight of the support, and then calcining in oxidizing conditions at temperature of about 550° C. or higher.

The support will, in any case, typically comprise at least about 50%, and can comprise at least about 60% of the resulting catalyst, in each case by weight relative to total weight of the supported catalyst. In preferred supported catalysts of the invention, the catalyst comprises the support in an amount ranging from about 70% to about 95%, and preferably from about 80% to about 90%, in each case by weight relative to total weight of the supported catalyst. The supports can be supplied to and integrated with the cataloxidant in any of a number of different ways, including for example as a separate component (e.g., as with wet-impregnation approaches for catalyst preparation) and/or as an integrated structure (e.g., as with sol-gel approaches for catalyst preparation).

Other additives and agents, such as binders and/or forming agents, can also be included with the catalysts.

In some specifically preferred embodiments of the invention, the cataloxidants of the present invention can comprise a noble metal component in an amount ranging from about 0.05% to 5% (preferably from about 0.1% to about 5%, and more preferably from about 0.5% to about 2%), a reducible metal oxide in an amount ranging from about 5% to about 50% (preferably from about 5% to about 30%, and more preferably from about 10% to about 20%), and a support, with percentages in each case being by weight relative to the total weight of the catalyst. If the catalyst further comprises a second (dopant) oxide component, a specifically preferred cataloxidant of the invention can comprise a noble metal component in an amount ranging from about 0.05% to 5% (preferably from about 0.1% to about 5%, and more preferably from about 0.5% to about 2%), a reducible metal oxide in an amount ranging from about 5% to about 50% (preferably from about 5% to about 30%, and more preferably from about 10% to about 20%), a second (dopant) oxide component in an amount ranging from about 0.1% to about 5% (preferably from about 0.5% to about 5%, and more preferably from about 1% to about 2%), and a support, with percentages in each case being by weight relative to total weight of the catalyst.

The various noble metals and metal oxides of the cataloxidant are described herein by reference to their elemental symbol, as set forth in the Periodic Table of the Elements. Hence, Pd refers to palladium, Pt refers to platinum, Rh refers to rhodium, Ir refers to iridium, Ru refers to ruthenium, Os refers to osmium, Au refers to gold, Ag refers to silver, Ni refers to nickel, Mn refers to manganese, V refers to vanadium, Ce refers to cerium, Th refers to terbium, Pr refers to praseodymium, Te refers to tellurium, Re refers to rhenium, Co refers to cobalt, Bi refers to bismuth, Cr refers to chromium, Mo refers to molybdenum, W refers to tungsten, Nb refers to niobium, Ga refers to gallium, Al refers to aluminum, Y refers to yttrium, Zn refers to zinc, In refers to indium, Fe refers to iron, Sb refers to antimony, Ti refers to titanium, Zr refers to zirconium, Li refers to lithium, Na refers to sodium, K refers to potassium, Cs refers to cesium, Mg refers to magnesium, Ca refers to calcium, Sr refers to strontium, Ba refers to barium, La refers to lanthanum, Nd refers to neodymium, Pm refers to promethium, Sm refers to samarium, Eu refers to europium, Gd refers to gadolinium, Dy refers to dysprosium, Ho refers to holmium, Er refers to erbium, Tm refers to thulium and Yb refers to ytterbium.

The noble metal component of the cataloxidant can comprise noble metals in their fully reduced (ground) state, but may also include noble metals in their partially or fully oxidized state. As discussed below, oxide forms of the noble metals (e.g., oxides of Rh) are reduced during catalyst pretreatment protocols and/or are reduced in situ by the aminating agent. The metal oxide components can comprise any of the various oxides associated with a particular metal; that is, the particular metal may be in a partially or fully oxidized state. The particular oxidation state of a particular metal oxide will vary depending on the conditions to which the metal/metal oxide is exposed and thermodynamic considerations. The various oxidation states, the particular molecular structure associated therewith, and the thermodynamic stability thereof at various conditions is well known in the art. It is contemplated, moreover, that the metal oxides can be supplied to the catalyst composition (and to the reactor) as metals in their fully-reduced states (e.g., ground states), or in a lower-oxidation state than the desired oxidation state, and then oxidized as a pretreatment step.

The catalysts can be prepared by suitable methods presently known or later developed in the art. Exemplary preferred methods for preparing the cataloxidants include impregnation approaches, co-precipitation approaches, sol-gel approaches, lyophilization (freeze-drying) approaches, spray-drying approaches, and/or slurrying/solvent evaporation approaches.

In a wet-impregnation approach, for example, the noble metal I reducible metal oxide catalysts are typically prepared from precursor solutions or dispersions and then treated, either external to the reaction zone of the reactor before the reaction and/or in situ in the reaction zone of the reactor during the amination reaction. A noble metal precursor solution can comprise, for example, the noble metal of interest and/or oxides or salts thereof. The reducible metal-oxide precursor solution can comprise the metal oxide in the desired oxidation state, an oxide of the metal in a relatively lower or higher oxidation state, and/or salts thereof. In a preferred approach, the noble-metal precursor solution and metal-oxide precursor solution are solutions of metal salts in water, and preferably in halide-free (e.g., chloride-free) water. For supported cataloxidants, a support material (e.g.. $ZrO_2$) can be characterized (e.g., with respect to pore volume) and/or pretreated (e.g., calcined at moderate temperatures, such as from about 80° C. to about 250° C., and preferably at about 110° C., to remove adsorbed gases or water) prior to use in cataloxidant preparation. The precursor solutions are preferably combined in the appropriate desired ratios, with the total volume of the combined solution being equal to the measured pore volume. The support material can then be impregnated with the combined precursor solutions. In an alternative approach, the various metal precursor solutions can be applied to the support material individually and sequentially. Several impregnation steps may be required, particularly for larger precursor solution volumes. The impregnated supports are typically dried slowly (e.g., at temperatures ranging from about 80° C. to about 110° C. for a few hours) and then oxidatively calcined (e.g., in air or oxygen at a temperature of about 300° C. to about 600° C. for a few hours) to form a reducible metal oxide in a higher oxidized state. To the extent that the noble metals included in the cataloxidant composition are likewise oxidized (e.g., Rh, and to a lesser degree, Ir, Ru and/or Pd), these oxidized noble metals can be selectively reduced in a further pretreatment step and/or in situ during an early part of the amination reaction. For example, the cataloxidants can be heated to a temperature of about 150° C. to about 200° C. in an atmosphere comprising hydrogen, to selectively reduce the noble metal (without substantially reducing the reducible metal oxide). In addition to the drying, calcination and optional selective noble metal reduction steps, it may likewise be desirable to thermally activate the cataloxidants, particularly for cataloxidants that have been stored for some period of time prior to use. Specifically, the cataloxidants can be heated in an inert atmosphere (e.g., nitrogen) to remove contaminants therefrom. The approaches outlined herein for catalyst preparation are to be considered exemplary and non-limiting.

Where the metal oxides component of the invention are prepared from metal oxide precursors, it may be necessary to convert the known precursor weight to the weight of the oxide actually in the catalyst. According to one approach for calculating the relative amounts of metal oxide components (ie., reducible metal oxides or dopant metal oxides) in a catalyst composition prepared from definitive amounts of metal-oxide precursors (e.g., nitrate salts of the corresponding metal) followed by oxidative calcination to the oxide, it is assumed that the most likely dominant thermodynamically-stable oxidation state(s) of the oxide is (are) formed. For example, oxidation of Ni metal is assumed, for purposes herein, to form an oxide consisting substantially of NiO. Oxidation of Mn metal is assumed, for purposes herein, to form an equimolar mixture of manganese oxides—specifically, $Mn^2O_3$ and $MnO_2$ on a 50% 50% molar basis.

Aromatic Hydrocarbons and Heterocyclic Analogs Thereof

The cataloxidants of the invention can be employed to effect the conversion of an aromatic hydrocarbon or a heterocyclic analog thereof to its corresponding arylamine or heteroarylamine. As used herein, the term "aromatic hydrocarbon" refers to an unsaturated cyclic hydrocarbon comprising one or more rings and having exclusively aromatic C—H bonds (rather than aliphatic C—H bonds). The aromatic hydrocarbons of the invention comprise, in preferred embodiments, one or more 5-carbon or 6-carbon rings. As used herein, a "heterocyclic analog" of an aromatic hydrocarbon refers to such unsaturated cyclic hydrocarbons in which one or more of the ring-carbon atoms have been replaced with a heteroatom selected from the group consisting of N, O and S. The aromatic hydrocarbons and heterocyclic analogs thereof are collectively referred to herein, alternatively, as the "aromatic reactants" of the invention.

The aromatic hydrocarbon and/or the heterocyclic analog thereof can be unsubstituted or substituted. A substituted aromatic hydrocarbon or a substituted heterocyclic analog thereof is a compound in which one or more of the hydrogen atoms bonded to a carbon atom or to a heteroatom of the ring is replaced by another group, such as, without limitation, alkyl, alkenyl, alkynyl, substituted alkyl, substituted alkenyl, substituted alkynyl, heteroalkyl, heteroalkenyl, heteroalkynyl, substituted heteroalkyl, substituted heteroalkenyl, substituted heteroalkynyl, cycloalkyl, cycloalkenyl, substituted cycloalkyl, substituted cycloalkenyl, halogen, hydroxy, alkoxy, aryloxy, amino, amide, thio and phosphino. For general purposes herein, unless a specific "substituted" or "unsubstituted" adjective is employed in connection with the structural nomenclature for a particular chemical compound or moiety, such structural nomenclature should be considered to be generic to either the substituted or unsubstituted form of the compound or moiety. Preferred substituents for the aromatic hydrocarbon or heterocyclic analog thereof are those moieties selected from the group consisting of $C_{1-6}$ alkyls, $C_{1-6}$ alkenyls, $C_{1-6}$ alkynyls, $C_{3-8}$ cycloalkyls, $C_{3-8}$ cycloalkenyls, alkoxy, aryloxy, amino and amido, where the designation "$C_{1-6}$" alkyls, alkenyls or alkynyls refers to one or more the respective groups having from one to six carbon atoms in the main chain, and the designation "$C_{3-8}$" cycloalkyls or cycloalkenyls refers to one or more the respective ring structures having from three to eight carbon atoms. The number of substituents groups on a substituted aromatic hydrocarbon or heterocyclic analog thereof is not critical, and will generally depend on the particular aromatic hydrocarbon I heterocyclic analog and/or on the reactivity of the substituents. Preferably, however, the aromatic hydrocarbon or heterocyclic analog thereof has at least one hydrogen atom bonded to a carbon or to a heteroatom of the aromatic or heterocyclic analog ring structure. Hence, a six-member ring preferably has five or less substituent groups, and a five-member ring preferably has four or less substituent groups. In some embodiments, the number of substituent groups on a six-member ring can be four or less, or even three or less. The number of substituent groups on a five-member ring can be three or less or even two or less.

In preferred embodiments, the aromatic hydrocarbon and/or heterocyclic analog thereof can be represented by compounds having the formula:

$$(A)-(B)_n.$$

As used in this formula, A is, independently, aryl or heteroaryl. In preferred embodiments, A can be selected from the group consisting of phenyl, diphenyl, benzyl, dibenzyl, napthyl, anthracene (i.e., anthra), pyridyl and quinoline. The subscript "n" is an integer generally ranging from 0 to 5, especially in connection with six-membered aryl or heteroaryl groups. The value of "n" can also range from 0 to 4, especially in connection with five-membered aryl or heteroaryl groups. The value of "n" more preferably ranges, in the general case, from 0 to 3, from 0 to 2, or from 0 to 1. As used in this formula, "B" is independently selected from the group consisting of hydrogen, alkyl, alkenyl, alkynyl, substituted alkyl, substituted alkenyl, substituted alkynyl, heteroalkyl, substituted heteroalkyl, cycloalkyl, cycloalkenyl, substituted cycloalkyl, substituted cycloalkenyl, halogen, hydroxy, alkoxy, aryloxy, carbonyl, amino, amido, thio and phosphino. In preferred embodiments, B can be independently selected from the group consisting of hydrogen, $C_{1-6}$ alkyl, $C_{1-6}$ alkenyl, $C_{1-6}$ alkynyl, $C_{3-8}$ cycloalkyl, $C_{3-8}$ cycloalkenyl, alkoxy, aryloxy, amino and amido.

As used herein, the phrases "having the formula" or "characterized by the formula" are intended to be open-ended, non-limiting and used in the same way that "comprising" is commonly used. The term "independently selected" is used herein to indicate that the "B" groups can, where n is 2 or greater, be identical or different (e.g., where n=3, the B groups could be designated as $B^1$, $B^2$ and $B^3$, and these may all be, in one case, substituted alkyls or alternatively in another exemplary case, $B^1$ and $B^2$ may be a substituted alkyl and $B^3$ may be an aryl, etc.). A particularly recited "A" group or "B" group will generally have the structure that is recognized in the art as corresponding to groups having that name. For the purposes of illustration, representative B groups as enumerated above are defined herein. These definitions are intended to supplement and illustrate, not preclude or replace the definitions known to those of skill in the art.

The term "alkyl" is used herein to refer to a branched or unbranched, saturated acyclic hydrocarbon radical. Exemplary alkyl radicals include, for example, methyl, ethyl, n-propyl, i-propyl, n-butyl, t-butyl, i-butyl (or 2-methylpropyl), etc. In particular embodiments, alkyls have between 1 and 50 carbon atoms, between 1 and 20 carbon atoms, between 1 and 6 carbon atoms or between 1 and 3 carbon atoms.

The term alkenyl is used herein to refer to a branched or unbranched acyclic hydrocarbon radical having at least one carbon-carbon double bond. Exemplary alkenyl radicals include, for example, 2-propenyl (or allyl), vinyl, etc. In particular embodiments, alkenyls have between 1 and 50 carbon atoms, between about 1 and 20 carbon atoms, between about 1 and 6 carbon atoms, or between about 1 and 3 carbon atoms. In addition, this term embraces radicals having both "cis" and "trans" orientations, or alternatively, "E" and "Z" orientations.

The term alkynyl is used herein to refer to a branched or unbranched acyclic hydrocarbon radical having at least one carbon-carbon triple bond. In particular embodiments, alkynyls have between 1 and 50 carbon atoms, between about 1 and 20 carbon atoms, between about 1 and 6 carbon atoms, or between about 1 and 3 carbon atoms.

"Substituted alkyl," "substituted alkenyl" and "substituted alkynyl" refer to the alkyl, alkenyl and alkynyl radicals, respectively, as just described in which one or more hydrogen atoms to any carbon of these radicals is replaced by another group such as a heteroatom, halogen, aryl, substituted aryl, cycloalkyl, cycloalkenyl, substituted cycloalkyl, substituted cycloalkenyl and combinations thereof Exemplary substituted alkyls include, for example, benzyl, trifluoromethyl and the like.

The term "heteroalkyl," "heteroalkenyl" and "heteroalkynyl" refer to the alkyl, alkenyl and alkynyl radicals, respectively, described above in which one or more of the carbon chain atoms of these radicals is replaced by a heteroatom selected from the group consisting of N, O and S. The bond between another carbon atom and the heteroatom may be saturated or, in some cases, unsaturated.

The term "cycloalkyl" is used herein to refer to a saturated cyclic non-aromatic hydrocarbon radical having a single ring or multiple condensed rings. Exemplary cycloalkyl radicals include, for example, cyclopentyl, cyclohexyl, cyclooctanyl, bicyclooctyl, etc. In particular embodiments, cycloalkyls have between 3 and 50 carbon atoms, between 3 and 20 carbon atoms, between 3 and 8 carbon atoms, or between 3 and 6 carbon atoms.

The term "cycloalkenyl" is used herein to refer to a partially unsaturated (i.e., having at least one carbon-carbon double bond), cyclic non-aromatic hydrocarbon radical having a single ring or multiple condensed rings. Exemplary cycloalkenyl radicals include, for example, cyclopentenyl, cyclohexenyl, cyclooctenyl, etc. In particular embodiments, cycloalkenyls have between 3 and 50 carbon atoms, between 3 and 20 carbon atoms, between 3 and 8 carbon atoms, or between 3 and 6 carbon atoms.

"Substituted cycloalkyl" and "substituted cycloalkenyl" refer to cycloalkyl and cycloalkenyl radicals, respectively, as just described wherein one or more hydrogen atoms to any carbon of these radicals is replaced by another group such as a halogen, alkyl, alkenyl, alkynyl, substituted alkyl, substituted alkenyl, substituted alkynyl, aryl, substituted aryl, cycloalkyl, cycloalkenyl, substituted cycloalkyl, substituted cycloalkenyl, heterocyclo, substituted heterocyclo, heteroaryl, substituted heteroaryl, alkoxy, aryloxy, boryl, phosphino, amino, silyl, thio, seleno and combinations thereof. Exemplary substituted cycloalkyl and cycloalkenyl radicals include, for example, 4-dimethylaminocyclohexyl, 4,5-dibromocyclohept-4-enyl, and the like.

The term "aryl" is used herein to refer to an aromatic substituent which may be a single aromatic ring or multiple aromatic rings which are raised together, linked covalently, or linked to a common group such as a methylene or ethylene moiety. The common linking group may also be a carbonyl as in benzophenone or oxygen as in diphenylether or nitrogen in diphenylamine. The aromatic ring(s) may include phenyl, naphthyl, diphenyl, diphenylether, diphenylamine and benzophenone among others. In particular embodiments, aryls have between 1 and 50 carbon atoms, between 1 and 20 carbon atoms, between 1 and 8 carbon atoms, or between 1 and 6 carbon atoms.

"Substituted aryl" refers to aryl as just described in which one or more hydrogen atom to any carbon is replaced by one or more functional groups such as alkyl, alkenyl, alkynyl, substituted alkyl, substituted alkenyl, substituted alkynyl, cycloalkyl, cycloalkenyl, substituted cycloalkyl, substituted cylcoalkenyl, heterocyclo, substituted heterocyclo, halogen, alkylhalos (e.g., $CF_3$), hydroxy, amino, phosphino, alkoxy, amino, thio and both saturated and unsaturated cyclic hydrocarbons which are fused to the aromatic ring(s), linked covalently or linked to a common group such as a methylene or ethylene moiety. The linking group may also be a carbonyl such as in cyclohexyl phenyl ketone.

The term "heterocyclo" is used herein to refer to saturated, partially unsaturated and unsaturated cyclic radicals (including, for example, cycloalkyl and cycloalkenyl radicals as described), wherein one or more or all carbon atoms of the radical are replaced by a heteroatom such as nitrogen, oxygen or sulfur. Additionally, the term "heteroaryl" as used herein refers to a specific example of a class of unsaturated cyclic radicals wherein one or more carbon atoms of an aromatic ring or rings are replaced by a heteroatom(s) such as nitrogen, oxygen or sulfur. Heteroaryl refers to structures that may be a single aromatic ring, multiple aromatic ring(s), or one or more aromatic rings coupled to one or more nonaromatic ring(s). In structures having multiple rings, the rings can be fused together, linked covalently, or linked to a common group such as a methylene or ethylene moiety. The common linking group may also be a carbonyl as in phenyl pyridyl ketone. As used herein, rings such as thiophene, pyridine, isoxazole, phthalimide, pyrazole, indole, furan, etc. or benzo-fused analogues of these rings are defined by the term "heteroaryl." Other exemplary heterocyclo radicals include, for example, piperazinyl, morpholinyl, tetrahydropyranyl, tetrahydrofuranyl, piperidinyl, pyrrolidinyl, oxazolinyl, and the like.

"Substituted heterocyclo" and "substituted heteroaryl" refer to heterocyclo and/or heteroaryl radicals as just described wherein one or more hydrogen atom to any atom of the radical is replaced by another group such as a halogen, alkyl, substituted alkyl, aryl, substituted aryl, heteroaryl, substituted heteroaryl, alkoxy, aryloxy, boryl, phosphino, amino, silyl, thio, seleno and combinations thereof. Exemplary substituted heteroaryl radicals include, for example, 4-N,N-dimethylaminopyridine. Other exemplary substituted heterocyclo radicals include, for example, N-methylpiperazinyl, 3-dimethylaminomorpholine, and the like.

The term "alkoxy" is used herein to refer to the —$OZ^1$ radical, where $Z^1$ is selected from the group consisting of alkyl, substituted alkyl, cycloalkyl, substituted cycloalkyl, heterocycloalkyl, substituted heterocycloalkyl, silyl groups and combinations thereof as described herein. Exemplary alkoxy radicals include, for example, methoxy, ethoxy, benzyloxy, t-butoxy, etc. A related term is "aryloxy" where $Z^1$ is selected from the group consisting of aryl, substituted aryl, heteroaryl, substituted heteroaryl, and combinations thereof. Examples of suitable aryloxy radicals include phenoxy, substituted phenoxy, 2-pyridinoxy, 8-quinalinoxy and the like.

As used herein the term "silyl" refers to the —$SiZ^1Z^2Z^3$ radical, where each of $Z^1$, $Z^2$, and $Z^3$ is independently selected from the group consisting of alkyl, substituted alkyl, cycloalkyl, heterocycloalkyl, heterocyclic, aryl, substituted aryl, heteroaryl, substituted heteroaryl, alkoxy, aryloxy, amino, silyl and combinations thereof.

As used herein the term "boryl" refers to the —$BZ^1Z^2$ group, where each of $Z^1$ and $Z^2$ is independently selected from the group consisting of alkyl, substituted alkyl, cycloalkyl, heterocycloalkyl, heterocyclic, aryl, substituted aryl, heteroaryl, substituted heteroaryl, alkoxy, aryloxy, amino, silyl and combinations thereof.

As used herein, the term "phosphino" refers to the group —$PZ^1Z^2$, where each of $Z^1$ and $Z^2$ is independently selected from the group consisting of hydrogen, substituted or unsubstituted alkyl, cycloalkyl, heterocycloalkyl, heterocyclic, aryl, heteroaryl, silyl, alkoxy, aryloxy, amino and combinations thereof.

The term "amino" is used herein to refer to the group —$NZ^1Z^2$, where each of $Z^1$ and $Z^2$ is independently selected from the group consisting of hydrogen, alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, silyl and combinations thereof.

The term "thio" is used herein to refer to the group—$SZ^1$, where $Z^1$ is selected from the group consisting of hydrogen; alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, silyl and combinations thereof.

The term "seleno" is used herein to refer to the group —$SeZ^1$, where $Z^1$ is selected from the group consisting of hydrogen; alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, silyl and combinations thereof.

The term "saturated" refers to lack of double and triple bonds between atoms of a radical group such as ethyl, cyclohexyl, pyrrolidinyl, and the like.

The term "unsaturated" refers to the presence one or more double and triple bonds between atoms of a radical group such as vinyl, acetylenyl, oxazolinyl, cyclohexenyl, acetyl and the like.

In preferred applications of the invention, the cataloxidants of the invention are employed for amination of an aromatic hydrocarbon selected from, independently, benzene, napthalene, anthracene, toluene, xylene, phenol and aniline, or for amination of heterocyclic analogs selected from, independently, pyridine and quinoline. Other specific exemplary aromatic hydrocarbons and/or heterocyclic analogs thereof for which the cataloxidants of the invention will find applications are disclosed, for example, in U.S. Pat. No. 3,919,155 to Squire (see Col. 5 at lines 15–62). Mixtures of two or more of the aforementioned aromatic hydrocarbons and/or the aforementioned heterocyclic analogs thereof can also be aminated in the presence of the cataloxidants of the invention. The cataloxidants of the invention are more preferably used for amination of benzene, toluene, aniline and/or a mixture of two or more of the same. In a particularly preferred embodiment, benzene is catalytically aminated in the presence of the cataloxidants to form aniline.

Aminating Agents

The aromatic reactants (ie., the aromatic hydrocarbons or heterocyclic analogs thereof) are reacted with an aminating agent in the presence of the cataloxidants to form the corresponding aryl amine or heteroarylamine. The aminating agents employed in the reaction are not critical, and can generally include a compound or salt comprising or capable of leaving a —$NH_2$ moiety. Ammonia is a preferred aminating agent. Ammonium salts, such as ammonium carbonate or ammonium carbamate can also be employed. Substituted amines, such as alkylamines (e.g., methylamine, and other primary alkylamines), hydroxyamines and alkoxyamines can also be suitably used as aminating agents. Hydrazine can also be an aminating agent. The aminating agents can also be characterized as including compounds (e.g., urea) that decompose to form ammonia in situ in the reaction zone under the reaction conditions therein.

Amination Reaction

The aromatic reactant (e.g., benzene) is reacted with the aminating agent in the presence of one of the above-described cataloxidants to form an arylamine or heteroarylamine reaction product (e.g., aniline). Briefly, the aromatic reactant and the aminating agent are supplied to a reaction zone of a reactor, and are allowed to interact with each other on a molecular level in the reaction zone. Without being bound by theory, the aromatic reactant and/or the aminating agent contact the catalyst under reaction conditions suitable to effect the amination reaction of interest.

The reactor can be a batch reactor or a flow reactor. The particular type of reactor is, however, not critical, and can include a variety of reactor types and configurations known in the art of heterogeneous catalysis. Typical reactors include, for example, pressure-vessel batch reactors, autoclaves, fixed-bed plug-flow reactors, fluidized-bed reactors, continuous-stirred tank reactors, bubble-reactors, etc., each of which should be operable at and capable of providing the conditions (e.g., temperature, pressure, residence time) that favor the reaction of interest. The reactor configuration can be a single reactor, series of single reactors and/or two or more parallel reactors. The reaction-process configuration can include batch reactions, semi-continuous reactions and/or continuous reactions. Particular reactor designs, reactor configurations and reaction-process configurations can vary depending on the amination reaction of interest, the phase-state of the aromatic reactant and/or the aminating agent, the required contact times, as well as the particular nature of the cataloxidant. In preferred embodiments, the amination reaction is effected in a high-pressure batch reactor, a continuous-flow fixed-bed reactor, or a fluidized-bed reactor.

The reactor can be a batch reactor or a flow reactor. The particular type of reactor is, however, not critical, and can include a variety of reactor types and configurations known in the art of heterogeneous catalysis. Typical reactors include, for example, pressure-vessel batch reactors, autoclaves, fixed-bed plug-flow reactors, fluidized-bed reactors, continuous-stirred tank reactors, bubble-reactors, etc., each of which should be operable at and capable of providing the conditions (e.g., temperature, pressure, residence time) that favor the reaction of interest. The reactor configuration can be a single reactor, a series of single reactors and/or two or more parallel reactors. The reaction-process configuration can include batch reactions, semi-continuous reactions and/or continuous reactions. Particular reactor designs, reactor configurations and reaction-process configurations can vary depending on the amination reaction of interest, the phase-state of the aromatic reactant and/or the aminating agent, the required contact times, as well as the particular nature of the cataloxidant. In preferred embodiments, the amination reaction is effected in a high-pressure batch reactor, a continuous-flow fixed-bed reactor, or a fluidized-bed reactor.

Figure 3B:
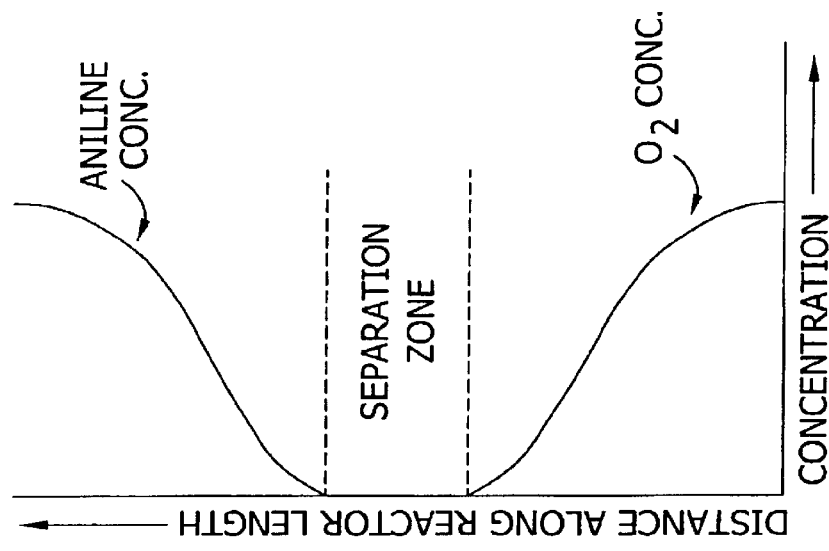
FIG. 3A is a schematic representation of one potential embodiment of a two-zone, redox fluidized-bed application of the present process, while 3B is a graph generally, depicting the consumption of oxygen and the formation of aniline over the length of the fluidized-bed reactor.
Figure 3A:
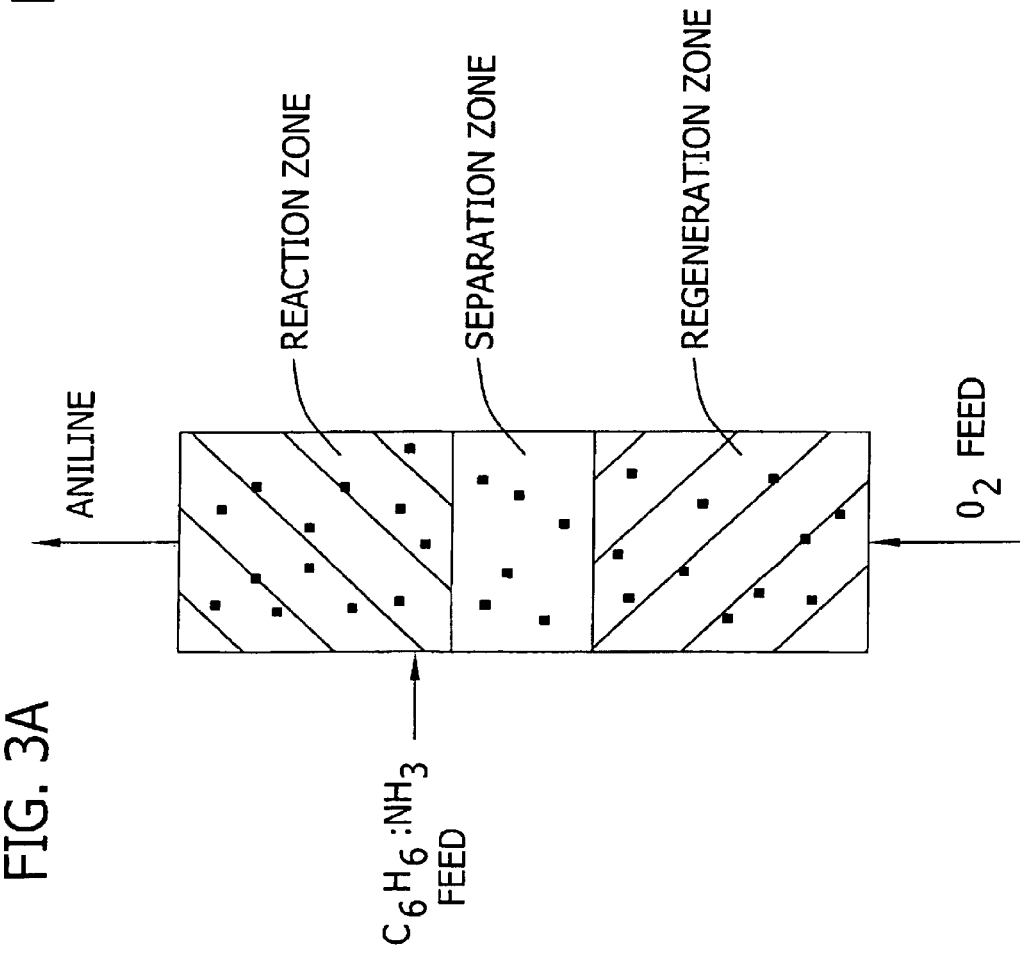

With regard to the fluidized-bed reactor, is it to be noted that in some embodiments the present process is preferentially carried out in a two-zone, redox fluidized-bed reactor or, alternatively, in a pulsed fluidized-bed reactor. The two-zone, redox fluidized-bed reactor concept has previously been proposed for different reaction systems by, for example, J. Soler et al. (oxidative dehydrogenation of hydrocarbons; *Catalyst Letters,* 50, pp. 25–30 (1998); *Ind. Eng. Chem. Res.,* 38, pp. 90–97 (1999)), R. Ramos et al. (oxidation of hydrocarbons; *J of Catalysis,* 163, pp. 218–221 (1996)), and P. Montgomery (production of stilbene and styrene; U.S. Pat. No. 3,965,206). Referring now to FIG. 3, generally speaking, the two-zone reactor is employed as follows: reactant gases (i.e., the aromatic hydrocarbon or heterocyclic analog thereof, and the aminating agent, such as benzene and ammonia, respectively) and an oxygen-containing gas are continuously fed or introduced into a fluidized-bed gas/solid contact zone comprising a fluidized particulate catalyst suspended in a process gas stream flowing through the contact zone. The castalyst is active for promoting the amination of the aromatic heterocycle, or analog thereof, to the corresponding amine (for example, benzene to aniline), and is subject to reduction in a redox reaction with hydrogen gas produced as a by-product of the reaction between the given reactant and the aminating agent, and is further subject to reoxidation by redox reaction with molecular oxygen. The process gas stream comprises the gases introduced into the contact zone as well as the reaction products produced therein.

It is to be noted that the point of introduction of oxygen into the fluidized-bed contact zone is spaced upstream from the point of introduction of benzene into the contact zone, with respect to the direction of the process gas flow through the contact zone. It is to be further noted that the velocity of the gas flow, the particle size and the configuration of the suspended catalyst and the geometric configuration of the gas/liquid contact zone are such that the process gas flows through the contact zone substantially in plug flow (i.e., the process gas flows through the contact zone without substantial axial back-mixing), while the suspended catalyst is substantially back-mixed therein.

Figure 4:
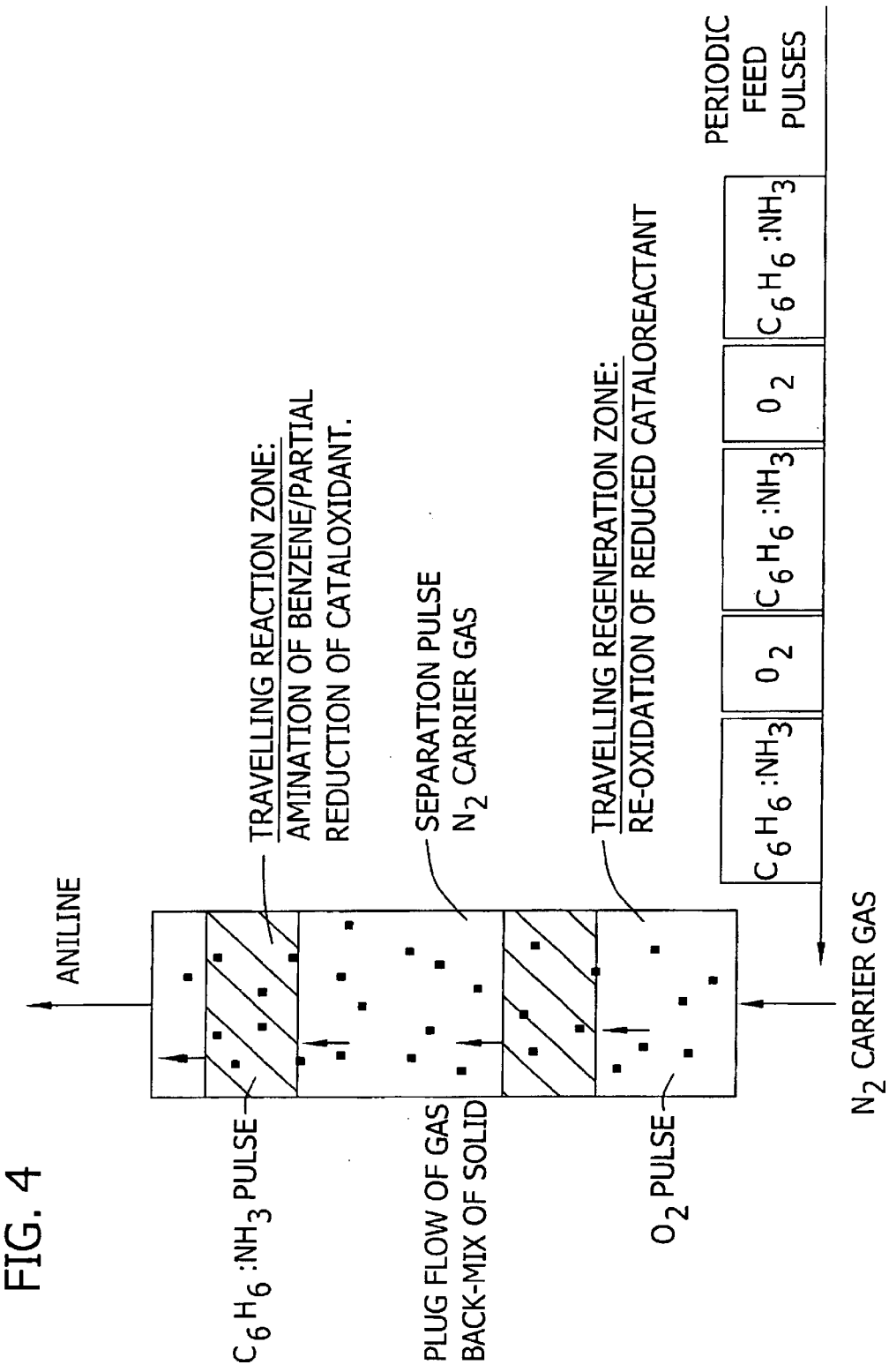
FIG. 4 is a schematic representation of one potential embodiment of a pulse-feed, fluidized-bed application of the present process.

Without being held to a particular theory, it is believed that the reactant hydrocarbon is oxidatively aminated by the cataloxidant downstream of the point of introduction of oxygen into the reaction zone, and thereof this reaction occurs in the substantial absence of the gaseous oxygen feed; that is, the oxygen content is less than about 1000 ppma relative to the concentration of the aromatic hydrocarbon (i.e., benzene) or heterocyclic analog thereof, and is preferably less than about 500 ppm, 250 ppm, 100 ppm or less. Likewise, the spent cataloxidant (i.e., the reduced cataloxidant) is reoxidized by molecular oxygen in the substantial absence of the gaseous reactant feed. These two reactions may be carried out continuously because of the plug flow behavior of the gas feeds and the back-mixing behavior of the cataloxidant solids in the fluidized-bed. The pulsed feed fluidized-bed reactor takes advantage of the plug flow manner by which gases proceed through the cataloxidant bed, as well. More specifically, referring now to FIG. 4, in this approach a gaseous aromatic hydrocarbon, or an analog thereof, a gaseous aminating agent and oxygen (or an oxygen-containing gas) are introduced into a process gas stream that flows through a fluidized bed gas/solid contact zone which comprises a fluidized particulate catalyst suspended in the process gas stream. The catalyst, as previously noted, is active for promoting the amination of the aromatic hydrocarbon or the analog thereof to the corresponding amine (for example, benzene to aniline), is subject to reduction in a redox reaction with hydrogen gas produced as a by-product of the reaction between the aromatic hydrocarbon and the aminating agent, and is subject to reoxidation redox reaction with molecular oxygen. The process gas stream comprises the gases introduced into the contact zone as well as the reaction products produced therein.

The introduction of oxygen into the gas/solid contact zone and the process gas stream is temporally alternated with the introduction of the aromatic hydrocarbon or analog thereof and the aminating agent into the process gas stream so that molecular oxygen gas is substantially absent from said process gas in any region of the contact zone containing an excess of the aminating agent and/or the aromatic hydrocarbon with respect to oxygen (i.e, the oxygen content is less than about 1000 ppma relative to the concentration of the aromatic hydrocarbon (i.e., benzene) or heterocyclic analog thereof, and is preferably less than about 500 ppm, 250 ppm, 100 ppm or less, while the aromatic hydrocarbon/analog thereof and the aminating agent are substantially absent from said process gas in any region of the gas/solid contact zone containing an excess of molecular oxygen gas with respect to these.

It is to be noted that, as described above, the velocity of gas flow, the particle size and configuration of the suspended catalyst and the geometric configuration of the gas/liquid contact zone are such that the process gas flows through the contact zone substantially in plug flow (i.e., the process gas flows through the contact zone without substantial axial back-mixing), while the suspended catalyst is substantially back-mixed therein. It is to be further noted that process parameters, such as gas velocities, concentrations, and pulse duration may be optimized to ensure "breakthrough" of the oxygen gas or reactants at the reactor outlet does not occur, which could contaminate the product stream; that is, such parameters are controlled to ensure the reactant gases and the oxygen gas are consumed in the bed.

The above-referenced reactors are preferred, at least in part, because they essentially enable the cataloxidants to constantly remain in a partially reduced state, which is favorable for consistently obtaining high selectivity in the reaction. In addition, such continuous processes are believed to enable higher space time yields ("STY") to be obtained, as well as enable the use of lower operational pressures. Finally, such processes allow for other cataloxidant compositions to be employed such as, for example, a combination of nickle/nickel oxide only (i.e., a noble metal is not required).

With respect to the operating conditions necessary to carry-out the present process utilizing the above-described fluidized-bed embodiments, it is to be noted that the carrier gas is introduced into the gas/solid contact zone at a rate sufficient to establish fluidization of the particulate catalyst without substantial entrainment of the catalyst out of the contact zone. Under such conditions, the catalyst bed is highly back-mixed due to rapid recirculation of catalyst particles within the bed under the influence of the turbulent substantially plug flow of the gas. Once the temperature profile, nature of the catalyst, catalyst geometry, catalyst particle size distribution, and operating pressure have been chosen, the total gas flow rate effective for proper fluidization may be determined by one of ordinary skill in the art based on conventional fluid bed reactor design principles. The difference between oxygen flow rate and total flow rate determines the rate at which carrier gas should be introduced into the lower end of the gas/solid contact zone. Carrier gas exiting the upper end of the gas/liquid contact zone may be recirculated to the inlet of the contact zone after separation of reaction product, reaction by-products and unreacted benzene and ammonia. By cooling the reaction product gas exiting the amination zone, water, aniline, benzene and organic by-products may be condensed and separated from the gas phase. Two condensate phases are obtained comprising benzene and aniline in the organic phase, and ammonium hydroxide and aniline in the aqueous phase.

Ammonia remaining in the gas phase may be separated from the carrier gas by further condensation under pressure and refrigeration, or by passing the gas phase through an ammonia scrubber. Water, or a slightly acidic aqueous medium may serve as the scrubbing medium. The carrier gas exiting the ammonia scrubber may then be recirculated to the inlet of the oxidation zone, together with any makeup carrier gas that may be required. Any excess of carrier gas may be vented from the system, thereby purging any non-condensable impurities not removed in the ammonia scrubber.

The carrier gas is preferably an inert gas, such as nitrogen. Where air is used as the source of oxygen, carrier gas for steady state operation may be entirely supplied by the nitrogen in the air. Nitrogen from another source may be required for startup.

Ammonia-rich liquor exiting the scrubber may be transferred to an ammonia stripper in which ammonia is removed from the rich liquor for recycle to the amination zone of the fluid bed reactor. For example, steam or vacuum stripping may be employed. In vacuum operation, a side stream of carrier gas may be used to assist in stripping ammonia from the aqueous phase.

The organic phase of the condensate is distilled for recovery of benzene which is recycled, yielding a bottom stream comprising product aniline. Additional aniline may be recovered by stripping the aqueous condensate. Stripping the aqueous condensate also recovers ammonia which can be recycled to the amination zone together with recovered benzene and ammonia stripped from the scrubber liquor.

The catalyst can be supplied or loaded to a reaction zone of a reactor in a reaction-ready, pretreated form (e.g, after preparation and any necessary pre-reaction treatments external to the reaction cavity), or alternatively, the catalyst can be supplied to the reaction zone in a precursor form, with final catalyst preparation steps being carried out in situ in the reaction zone. For example, where the noble metal component of the catalyst is prepared from noble metal salts, catalyst pretreatment steps can include calcination to form a noble metal oxide, and/or reduction of a noble metal oxide (e.g., in the presence of hydrogen gas) to the noble metal, as discussed above. As another example, where the reducible metal oxide component of the catalyst is present as a catalyst precursor in a lower oxidation state, catalyst pretreatment steps can include oxidative calcination to form the metal oxide in a higher oxidation state. In any case, the catalyst is typically, but not necessarily, loaded in the reactor prior to supplying reactants thereto. The catalyst or catalyst precursor is typically a solid material while the reaction is being effected.

The overall amount of the cataloxidant loaded into the reaction zone of the reactor to effect the amination reaction of interest can vary with the particular reaction being effected, with the type of reactor, the reaction conditions, the form of the catalyst, the scale of the process (including, for example, the amounts of reactants supplied to the reaction zone of the reactor), and the catalyst loading scheme (e.g., one-time loading, versus intermittent reloading, etc.). In general, the catalyst loading should be sufficient to provide at least a catalytically effective amount of a noble metal. The catalytically effective amount of noble metal can vary with the particular reaction, the reaction conditions, the regeneration requirements and the form of the catalyst (e.g. supported or unsupported, porosity, surface area, preparation methods, etc.). The catalytically effective amount can be determined by optimization approaches known in the art. For example, a series of aniline synthesis reactions with varying amounts of cataloxidants (and varying amounts of the noble metal component thereof) can be conducted under lab or pilot scale reaction conditions and evaluated with respect to catalyst performance. In some cases, lower noble metal loadings can result in an increased likelihood of noble metal fouling, whereas higher noble metal loadings can result in an increased tendency for ammonia decomposition. The catalyst loading should, moreover, be generally sufficient to provide at least a stoichiometric amount of a reducible metal oxide, relative to the amount of hydrogen produced. However, it is to be noted that the stoichiometric amount of the reducible metal oxide will vary with the particular reaction, the amount of aromatic hydrocarbon or heterocyclic analog being converted, and with the particular reducible metal oxide. For example, in the conversion of benzene to aniline using NiO as a reducible metal oxide, one mole of hydrogen is produced for each mole of benzene converted, and can react with the NiO on a one to one mole basis to form $H_2O$, thereby requiring NiO in a molar amount equal to the molar amount of benzene converted. An amount of the reducible metal oxide in excess of the stoichiometric amount is preferred, including for example, a 50% molar excess, a 100% molar excess or more, relative to the stoichiometric required amount. The molar excess can be, in some cases, range from about a 5 times excess to about a 20 times excess, or from about a 5 times excess to about a 100 times excess, or from about a 5 times excess to about a 1000 times excess, in each case relative to the stoichiometric required amount.

A useful parameter for characterizing the catalyst loading for a batch reaction is the weight ratio of the total amount of all reactants to the total amount of catalyst, referred to herein as the "R/C ratio." The R/C ratio preferably ranges, in general for preferred applications in which benzene is converted to aniline, from about 0.1:1 to about 50:1, more preferably from about 0.1:1 to about 30:1, even more preferably from about 0.1:1 to about 20:1 and still more preferably from about 0.5:1 to about 10:1, in each case by weight. Particularly preferred R/C ratios for particular catalysts and particular reactions are discussed below. For a flow-reactor, the catalyst loading can be characterized in terms of a liquid hourly space velocity (LHSV). The LHSV preferably ranges from about 0.01 per hour to about 10 per hour, while in some instances it may range from about 0.05 per hour to about 5 per hour, or from about 0.1 per hour to about 3 per hour.

In this regard it is to be noted that productivity for batch and continuous processes will vary, for example, ranging from about 10 to about 1000 g aniline/hour/kg catalyst, depending upon the particular mode by with the process is carried out. More specifically, productivity for a batch process typically ranges from about 10 to less than about 100 g aniline/hour/kg catalyst (i.e., about 25, 50, 75, etc. g aniline/hour/kg catalyst), while productivity for a continuous process typically ranges from more than about 100 g aniline/hour/kg catalyst up to about 1000 g aniline/hour/kg catalyst (i.e, about 250, 500, 750, etc. g aniline/hour/kg catalyst).

The catalyst is typically exposed to (e.g., flushed with) an inert gas prior to admitting the reactants to the reaction zone of the reactor. Nitrogen is a suitable inert gas. Such flushing reduces the amount of gaseous oxygen in the reactor, thereby limiting the potential reaction between oxygen and ammonia (or other aminating agent).

The aromatic reactant and the aminating agent can, independently, be supplied to the reaction zone of the reactor as a gas or as a liquid. Preferences as to the phase of the aromatic reactant and/or the aminating agent will generally depend on the particular amination reaction being effected and/or on the particular reactor configuration. In preferred applications, such as the preparation of aniline from benzene, benzene and ammonia are preferably both present in the reaction zone as gaseous reactants. More specifically, typically benzene is supplied to the reaction vessel as a liquid, which then evaporates during heat-up to form a gas, while ammonia is present in the reaction vessel in the supercritical phase (i.e., present at a temperature and pressure which are both in excess of the respective critical temperature and pressure for ammonia).

The reactants can be supplied to the reaction zone together (e.g., as a pre-mixed reactant stream), or separately and, if separately, either concurrently or sequentially. The aromatic reactants and/or the aminating agent are preferably supplied to the reaction zone as a higher-grade, substantially pure feedstocks, but may alternatively, for certain reactions and/or for certain cataloxidants, be supplied as major components of lower-grade feedstocks.

The relative amount of aromatic reactant and aminating agent supplied to the reaction zone will vary, depending on the particular amination reaction and the reaction conditions. In general, at least stoichiometric amounts of these reactants are provided to the reaction zone. Typically, however, an amount in excess of the stoichiometric amount of one of the reactants relative to the other can be supplied to provide for more favorable kinetics, higher aromatic-reactant conversion, and/or to provide for improved product selectivity. In preferred applications, such as wherein gaseous benzene and gaseous ammonia are reacted to form aniline, the molar ratio of ammonia to benzene (the "$NH_3:C_6H_6$ ratio") can preferably range from about 0.1:1 to about 100:1, more preferably from about 0.5:1 to about 100:1, and even more preferably from about 1:1 to about 100:1.

In some embodiments, the $NH_3:C_6H_6$ ratio can range from about 1:1 to about 50:1, from about 1:1 to about 30:1, from about 1:1 to about 10:1, or from about 1:2 to about 1:8. In general, higher $NH_3:C_6H_6$ ratios favor improved selectivity for aniline, but can adversely affect the kinetics of benzene activation. Conversely, lower $NH_3:C_6H_6$ ratios favor improved benzene activation kinetics, but can adversely affect the aniline selectivity.

In this regard it is to be noted that while the above-noted ranges are expressed in terms of the ratio of ammonia to benzene, these ranges are generally applicable to the ratio of aminating agent to aromatic reactant.

Other co-reactants, co-catalysts or additional agents (e.g., scavenging agents) may also be supplied to the reaction zone of the reactor, with particulars thereof depending on the amination reaction of interest. For the direct amination of benzene, for example, gaseous oxygen or an oxygen-containing gas (e.g, air) can be supplied to the reaction zone of the reactor as a co-reactant. The relative amount of gaseous oxygen supplied to the reaction zone is not generally critical, and can vary depending on the relative amounts of noble metal components and reducible metal oxide components, and on the amount of catalyst loaded. The molar ratio of gaseous oxygen to benzene ("$O_2:C_6H_6$ ratio") can, for example, range from about 0.05:1 to about 1:1 and preferably from about 0.1:1 to about 1:1. It may also be advantageous, in some embodiments, to effect the benzene amination reaction without supplying oxygen or an oxygen-containing gas to the reaction zone; that is, in some embodiments the reaction may be carried out in the essential absence of an oxygen co-reactant and/or oxygen co-feed.

The reaction conditions, especially temperature, pressure and residence time are controlled to effect the desired amination reaction, and preferably, in a manner that optimizes aromatic reactant conversion, arylamine or heteroarylamine selectivity, and/or regenerability. For catalytic aniline preparation, for example, benzene is preferably aminated at a temperature, pressure and/or residence time controlled to, and with a cataloxidant selected to effect a benzene conversion of at least about 5%, 7%, 10% or more, with at least about 90%, 95% or more selectivity for aniline based on weight and relative to benzene. Generally speaking, the reaction temperature may be any temperature within the range bound on the lower end by the temperature needed to dehydrogenate benzene and on the higher end by the temperature at which coking begins; that is, generally the reaction temperature may be any temperature high enough to activate benzene for dehydrogenation but low enough to avoid coking. While this range may vary with the particular noble metal employed for the reaction, typically the reaction temperatures for benzene amination preferably range from about 200° C. to about 600° C., or from about 200° C. to about 500° C. and, in some embodiments, can range from about 250° C. to about 450° C., or from about 300° C. to about 400° C., the higher temperatures within each range being more preferred in order to increase the % conversion and the space time yield ("STY").

Reaction pressures for the amination reaction generally, and benzene amination in particular, preferably range from about 1 bar to about 900 bar, more preferably from about 1 bar to about 500 bar, and even more preferably from about 1 bar to about 300 bar. In some embodiments, the pressure in the reaction zone can range about 50 bar to about 300 bar, from about 100 bar to about 300 bar, or from about 150 bar to about 300 bar. However, it is to be noted that the particular reaction pressure employed is at least in part a function of the type of reactor in which the reaction is carried out. For example, for some applications utilizing a batch-type reactor, the pressure is typically greater about 100 bar, while for some application in which a continuous flow-type reactor is utilized, the pressure is typically less than about 100 bar (i.e., ranging from about 1 to about 50 bar).

The residence time, alternatively referred to herein as the contact time, is not generally critical, and can be optimized for a particular reaction system (i.e., for a particular cataloxidant, R/C ratio, $NH_3:C_6H_6$ ratio, temperature, pressure, etc.) with respect to conversion, selectivity and/or regenerability according to approaches known in the art. Typical residence times for benzene amination in batch reactors can range from about 15 minutes to about 8 hours, and preferably from about 30 minutes to about 4 hours, depending on the temperature. In general, shorter residence times can be achieved with higher reaction temperatures. For benzene amination in a batch reactor, a residence time of about 4 hours at about 300° C., or of about 15 minutes at about 400° C., or of about 1 hour at 350° C. can be satisfactory. For benzene amination in continuous-flow reactors, the residence times can range from about 0.25 seconds to about 20 minutes, and preferably from about 0.5 seconds to about 10 minutes. The aforementioned ranges are generally preferred, but should be considered non-limiting. Shorter contact times can be achieved, for example, by changing the reaction conditions, and particularly, the reaction temperature.

In this regard it is to be noted that, without being held to a particular theory, it is generally believed that the difference in reaction times between a batch reactor and a continuous flow reactor is at least in part due to the thermodynamic equilibrium of the reaction, or lack thereof. More specifically, in a batch reactor, the kinetics of the metal oxide reduction (e.g., NiO to Ni) are slow and conversion is low due to the thermodynamic equilibrium that is typically reached in this reaction. However, in a continuous flow reactor, the instantaneous ratio of catalyst to substrate is typically far greater than in batch, especially where the reaction is essentially gas phase, and therefore an equilibrium for this reaction is essentially never reached, so the overall amination reaction proceeds much faster and higher conversions are obtained.

The most preferred particular temperatures and the most preferred pressures can vary outside of the above-described generally preferred ranges and/or within the generally preferred ranges, depending on the particular catalyst being employed for the benzene amination reaction, as exemplified below. As discussed by Becker et al., varying and sometimes competing thermodynamics and/or kinetics concerns are implicated by varying the reaction temperature and pressure, as well as by the presence or absence of gaseous oxygen as a co-reactant. See Becker et al., *Amination of Benzene in the Presence of Ammonia Using a Group VIII Metal Supported on a Carrier as a Catalyst,* Cat. Let. 54, 124–128 (1998). In general, higher temperatures are desirable with respect to improved kinetics and improved thermodynamics for benzene conversion to aniline. However, higher temperatures also can implicate thermodynamic and kinetic concerns for side reactions and/or other reactions, such as decomposition of ammonia.

The reaction is preferably effected with appropriately selected heat transfer equipment and temperature-control systems in place. The reaction may be run, for example, isothermally or adiabatically, depending on the particular amination reaction, among other factors. For the direct amination of benzene, the reaction is preferably effected isothermally with appropriate heat-exchange equipment in thermal communication with the reaction zone of the reactor.

The product arylamine or heteroarylamine (e.g., aniline) can be isolated from other products and/or from excess reactants following the amination reaction. If the reaction is effected in a pressure-vessel batch reactor, for example, the reactor can be cooled to room temperature or lower, excess aminating agent (e.g., ammonia) can be vented, and a liquid phase can be separated from the cataloxidant. The product can then be isolated from the liquid phase. If the reaction is effected in a continuous flow reactor (e.g., a fixed-bed flow reactor), the gaseous product stream can be separated into its various product/excess reactant components, or alternatively, can be condensed, and the product can be isolated therefrom. For example, in certain instances (such as when no azeotropic mixtures are formed), product isolation may be achieved using a simple series of distillation columns. In such instances, upon exiting the continuous flow reactor, the gaseous product mixture can be passed through an initial condenser, where unreacted benzene, the product aniline, as well as any reaction byproducts (such as water, toluene, diphenyl), are condensed and collected. Non-condensibles present in the gaseous product stream, such as excess ammonia and, if present, unreacted hydrogen, can either be vented (for example to a flare) or recycled back to the reactor. The organic phase of the resulting condensed mixture may then proceed through a series of distillation columns, where various reactants, products and byproducts can be isolated and collected. In a first column, for example, benzene is distilled, the distilled benzene then being recycled directly to the reactor or collected for later use. The remaining mixture (i.e., the first "pot liquor") proceeds to a second distillation column, where typically a small amount of toluene is distilled and collected. The remaining mixture (i.e., the second "pot liquor") then proceeds to a third column where the product aniline is isolated from any diphenyl present and collected. Due to the highly selective nature of the present process, relatively small columns can be employed for the latter two separations because little, if any, of the byproducts toluene and diphenyl are formed.

For the benzene amination reaction, the conversion of benzene is preferably at least about 5% at the temperature and pressure ranges described above, and more preferably at least about 6% at such ranges. Even higher conversions are desirable and may be achieved through optimization protocols known in the art and/or later developed. Hence, the conversion of benzene can be at least about 7%, at least about 8%, 10% or higher. Still higher conversions can be achieved in continuous-flow systems. As used herein, the "conversion" of benzene or other aromatic reactant can be calculated according to the following equation:

$$\% \text{ conversion} = \frac{[(\text{amount of benzene})_{initial} - (\text{amount of benzene})_{final}] \times 100}{(\text{amount of benzene})_{initial}}$$

The amount of benzene, as used in the immediately-preceding equation can be expressed on a molar or a weight basis, and used consistently in the equation. The selectivity of the catalyst for aniline for the benzene amination reaction is preferably at least about 90%, preferably at least about 93%, more preferably at least about 95%, even more preferably at least about 97% and most preferably about 98%, in each case, based on weight and relative to benzene. The selectivity for aniline, based on weight and relative to benzene, can be calculated according to the following equation:

$$\% \text{ selectivity} = \frac{(\text{weight of aniline produced}) \times 100}{[(\text{weight of benzene})_{initial} - (\text{weight of benzene})_{final}]}$$

The conversion and selectivity values, as used herein, refer to the overall (i.e., effectively time and location integrated) conversion and selectivity values associated with the reaction. Values of differential conversions and/or selectivity (e.g., associated with local regions of the reaction zone and/or with shorter time periods) may vary from the overall values. Moreover, while the values of conversions and selectivity as referred to herein are intended to be based on total and complete mass-balance calculations, a rough approximation thereof (e.g., within about 2% to about 3% accuracy) can be based on gas chromatography-based values for benzene and/or aniline, or alternatively, based on other suitable analytical approaches in which the ignored factors amount to less than about 5% deviation from the result obtained with a comprehensive and rigorous mass balance. In any case, the overall aniline yield for the reaction is preferably at least about 4.5%, more preferably at least about 4.75%, and even more preferably at least about 5%, based on weight and relative to benzene. Higher yields are desirable and expected based on optimization of the cataloxidants and/or the reaction systems or conditions described herein.

For many of the amination reactions to which the present invention is directed, where the aromatic reactant conversion is less than 100%, and/or where a stoichiometric excess of the aminating agent is employed, it may be desirable to separate unreacted aromatic reactants and/or aminating agents from the desired product and optionally, also from each other, and in any case, to recycle such reactants to a reactant feed. In addition to such recycling approaches, it may also be desirable to charge the reactor during the course of the amination reaction, continuously or intermittently with fresh reactants, with fresh cataloxidant, and/or with fresh inerts or diluents (e.g., for pressure control). As described in greater detail below, the cataloxidant involved in the amination reaction can be wholly or partially regenerated.

For many of the amination reactions of the present invention, it will also be desirable to regenerate the catalyst (or at least a portion thereof), and particularly, the reducible metal oxide component of the catalyst, after the catalyst has been used to effect the amination reaction of interest for some period of time (such period also being referred to herein as an "initial period" or as an "initial reaction period"). In a typical application for the amination reaction, for example, and with reference to FIG. 1, the cataloxidant is contacted with an aromatic reactant such as benzene and/or with an aminating agent such as ammonia in a reaction zone of a reactor to form aniline for at least some initial period of time, with an initial benzene conversion being achieved and with a particular selectivity for aniline during this period of time. The catalyst performance (e.g., conversion and/or selectivity) can be monitored during such an initial period for an indication that the catalyst is becoming less effective with respect to such performance criteria. The relative amount of the reducible metal oxide that is in the reduced form (having a lower oxidation state) after the initial period is not critical. It is generally preferred, however, for purposes of reoxidation, that not all of the reducible metal oxide be in the lower oxidation state. For example, catalyst efficiencies of about 5% to about 50%, or from about 10% to about 30% are acceptable, with such "catalyst efficiency" referring to the relative amount of the reducible metal oxide component in the relatively reduced (i.e., relatively lower oxidation) state, based on weight, relative to the weight of the metal oxide component.

At least a portion of the catalyst contacted during the initial period can be regenerated, either within the reaction zone of the reactor or external thereto, by exposing the catalyst to oxidizing conditions, whereby the reduced form of the reducible metal oxide is reoxidized. Suitable oxidizing conditions typically include, for example, exposing the catalyst to oxygen gas or to an oxygen-containing gas (e.g. air) at a temperature ranging from about 200° C. to about 800° C., preferably from about 400° C. to about 600° C., and most preferably at about 475° C. for a period of time ranging from about 10 minutes to about 10 hours and preferably from about 30 minutes to about 5 hours. Optionally, the cataloxidant can be flushed, for example with inert gas, prior to the oxidative regeneration (e.g., to remove residual organics and/or ammonia before feeding oxygen and/or for heating and/or cooling purposes). The catalyst is, in preferred embodiments, regenerated without exposing the catalyst to reducing conditions. To the extent any noble-metal oxides are formed during the regeneration-oxidation step, such noble-metal oxides will be selectively reduced in situ at the start of the next amination reaction in the cycle.

In many cases (e.g., with a batch reactor, or with a continuous reactor having a fixed-bed or a fluidized bed), all of the catalyst in the reaction zone can be regenerated at the same time without removing the catalyst from the reaction zone of the reactor by changing the conditions in the reactor from the (initial) reaction conditions to the regeneration (oxidizing) conditions. In some cases (e.g., with a continuous, fluidized bed reactor), a portion of the catalyst can be continuously or intermittently withdrawn from the reaction zone, regenerated external thereto, and then reloaded into the reaction zone, without interrupting the continuous reaction occurring in the reaction zone.

Figure 2A:
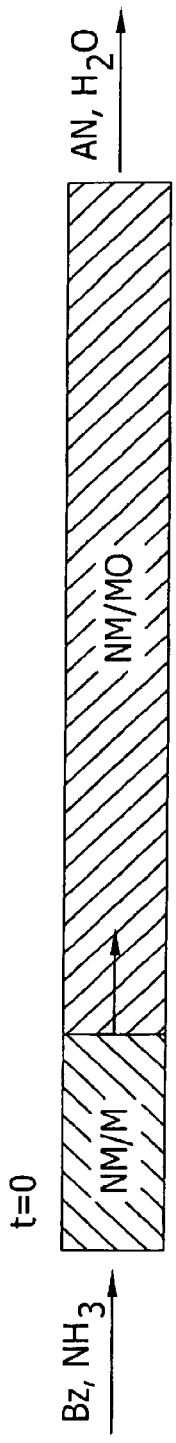
FIG. 2A through FIG. 2D are schematic representations of a continuous-flow, fixed-bed, tubular plug flow reactor comprising a noble metal/reducible metal oxide (NM/MO) catalyst. For aniline (AN) preparation, benzene (Bz) and ammonia ($NH_3$) are supplied to the reactor. The metal oxide is reduced in situ to a lower oxidation state, with the relative amount of the metal oxide in such a lower oxidation state varying at times t=0 (FIG. 2A), t=τ/2 (FIG. 2B) and t=τ (FIG. 2C). The reducible metal oxide can be regenerated by oxidizing with gaseous oxygen or an oxygen-containing gas (FIG. 2D).
Figure 2B:
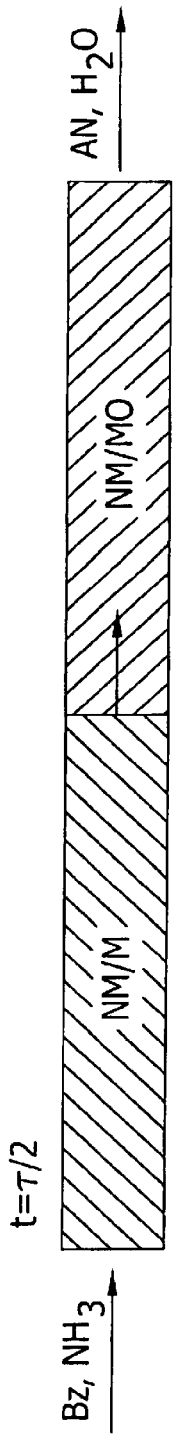
Figure 2C:
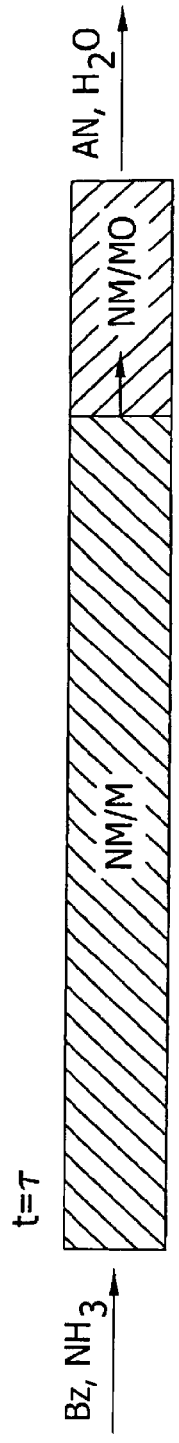
Figure 2D:
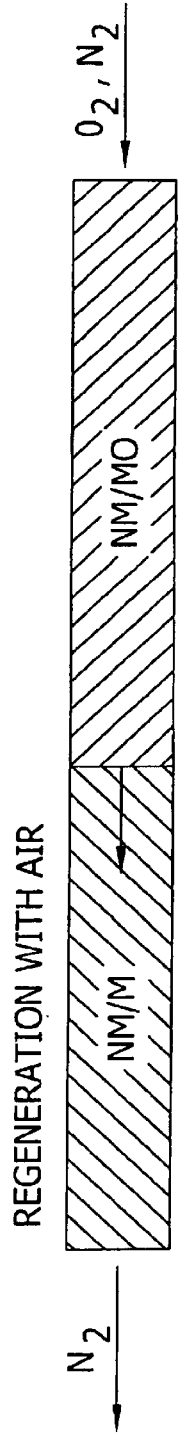

For the preferred benzene amination reaction, regeneration of the catalyst can be effected, for example, as follows. With reference to FIGS. 2A through 2C, benzene (Bz) and the aminating agent (e.g., $NH_3$ as shown in FIGS. 2A through 2C) are reacted over a noble metal (NM)/reducible metal oxide (MO) cataloxidant to form aniline (AN) during an initial reaction period, $\tau$. At a time, $t=0$, most, if not all, of reducible metal oxide component of the catalyst is present in the oxidized state (MO) (FIG. 2A). As the amination reaction progresses, reducible metal oxide(s) of the cataloxidant oxidize hydrogen gas produced in the aniline reaction, and the metal oxides are themselves reduced to the reduced state of the metal (M)—and are therefore present as reduced metal oxides. (FIG. 2B). After the initial reaction period, at a time, $t=\tau$, some or all of the reducible metal oxide (MO) component is in the reduced state (M) (FIG. 2C). The extent of metal-oxide reduction may be partial or complete, depending on the concentration of such oxides in the cataloxidant composition, the particular cataloxidant employed, and the duration of the reaction. An initial benzene conversion is achieved during the initial reaction period, preferably at least about 5% conversion with at least 90% selectivity for aniline based on weight and relative to benzene. The aniline selectivity is preferably even higher, as described above. In any case, with reference to FIG. 2D, at least a portion of the catalyst used to effect the reaction during the initial period is regenerated by exposing the catalyst to oxidizing conditions, as described, and preferably in oxygen gas or air at temperatures ranging from about 400° C. to about 500° C., whereby the reduced metal oxides are reoxidized to the corresponding reducible metal oxide form.

Advantageously, the catalyst can be regenerated without exposing the catalyst to reducing conditions (c.f., Du Pont's Ni/NiO catalyst, which requires both reduction and oxidation steps for regeneration). In preferred embodiments, the regeneration is effected to the entire catalyst bed at once, with the catalyst remaining in the reaction zone of the reactor as described above for the general case. The cycle of the amination reaction followed by regeneration (e.g., FIG. 2A through FIG. 2D) is then reiteratively effected at least four times for at least a portion of the catalyst to form an at least five-time-regenerated catalyst (a "5x-regenerated catalyst"). In preferred embodiments, such reiterative cycle is repeated at least nine times to form an at least ten-time-regenerated catalyst (a "10x-regenerated catalyst"). In either case, the 5x-regenerated catalyst, and preferably the 10x-regenerated catalyst retains commercially attractive performance criteria. Specifically, upon reaction during the next subsequent amination reaction cycle (i.e., the $6^{th}$ amination reaction over the 5x-regenerated catalyst, or the $11^{th}$ amination reaction over the 10x-regenerated catalyst), achievable benzene conversion is typically at least about 50% of the initial benzene conversion value, with conversions of at least about 75%, 85%, 90%, 95% and even about 100% of the initial conversion value being achievable in some instances, with at least about 90% selectivity for aniline (based on weight and relative to benzene) also being achieved.

While cataloxidant regenerability has been described herein with reference to FIGS. 2A through 2D in connection with a continuous-flow, fixed-bed, tubular plug-flow reactor, such description should be considered illustrative and non-limiting. Other reaction systems, including back-mixed systems such as fluidized bed and/or pressure-vessel batch reactors, will be more spatially homogeneous with respect to catalyst reduction and/or reoxidation.

Preferred Cataloxidants/Reaction Conditions for Aniline Preparation

As noted, preferred embodiments of the present invention are directed to the conversion of benzene to aniline using cataloxidants having noble metal components comprising, independently, Pd, Rh, Ru or Ir, and having a reducible metal oxide component comprising nickel oxide or, alternatively, cobalt oxide. Manganese oxide is, in some cases, included in the catalyst composition as an additional reducible metal oxide or as a dopant metal oxide.

In particularly preferred embodiments of the invention, the cataloxidant composition comprises a noble metal component consisting essentially of Rh or, alternatively, .consisting essentially of Ir. In other preferred embodiments of the invention, the cataloxidant composition comprises a noble metal component consisting essentially of Pd, or alternatively, consisting essentially of Ru. The noble metal component can comprise from about 0.05% to about 5% by weight relative to total weight of the catalyst. In any of the aforementioned cases, the reducible metal oxide component of the cataloxidant comprises or, in some cases, consists essentially of, nickel oxide or cobalt oxide, with the amount of metal oxide ranging from about 5% to about 30% by weight relative to the total weight of the catalyst. Manganese oxide can also be included in some of the aforementioned cataloxidant compositions, either as an additional reducible metal oxide or as a second dopant in an amount ranging from about 0.5% to about 20% by weight relative to total weight of the catalyst.

The cataloxidant compositions can further comprise a support in each of the aforementioned cases. The support is preferably zirconium dioxide or titanium dioxide, and preferably has a surface area of at least about 20 $m^2/g$ or higher, with a surface area of 50 $m^2/g$ being suitable in many cases, and a pore volume of at least about 0.2 cc/g, with 0.25 cc/g, 0.3 cc/g and 0.35 cc/g being suitable in many cases. Additionally, when $TiO_2$ is the support, it is also preferred that it be modified by impregnation with, for example, potassium, typically about 0.5% by weight. Preferred cataloxidant compositions are further discussed below individually for each preferred noble metal.

In this regard it is to be noted that, in those instances where the cataloxidant does not comprises a support, the noble metal component comprises about 0.5% to about 5% by weight relative to the total weight of the cataloxidant. The reducible metal oxide component comprises, or in some cases consists essentially of, nickle oxide or cobalt oxide, with the amount of the metal oxide ranging from about 30% to about 90%, and preferably from about 40% to about 80%, by weight relative to the total weight of the catalyst. The cataloxidant in such instances additionally comprises a binder and, optionally, a dopant (as previously described).

Catalyst compositions comprising the preferred components (or appropriate precursors thereof) are loaded into a batch or continuous reactor. The catalyst loading for a batch reactor, characterized with respect to the weight ratio of reactants to catalyst (R/C ratio) supplied to the reaction zone, ranges from about 0.1:1 to about 20:1, and in some cases from about 0.5:1 to about 10:1. If necessary, cataloxidant precursors can be oxidized with oxygen or an oxygen-containing gas, as described. The catalyst can also be flushed with an inert gas such as nitrogen. Benzene and ammonia are then supplied as gasses to the reaction zone, with the molar ratio of ammonia to benzene ranging from about 0.5:1 to about 100:1. Any noble metal oxides are selectively reduced with ammonia during heat up of the reaction system. Benzene and ammonia are reacted therein in the presence of the cataloxidants and at a temperature ranging from about 200° C. to about 500° C., and at a pressure ranging from about 1 bar to about 500 bar during the reaction. The residence time, is preferably about 1 hour for batch reactions, and preferably about 1 minute for continuous-flow reactions. Deviations and specific preferences, if any and where applicable, are discussed below in connection with the individual noble metal.

Rhodium Cataloxidants

Preferred rhodium-based supported cataloxidants of the invention for batch operation comprise, or alternatively, consist essentially of, Rh in an amount ranging from about 0.05% to about 2% by weight relative to total weight of the catalyst, nickel oxide in an amount ranging from about 10% to about 20% by weight relative to total weight of the catalyst, and manganese oxide in an amount ranging from about 0.5% to about 2% by weight relative to the total weight of the catalyst. Alternatively, nickel oxide and/or manganese oxide may be replaced with, for example, cobalt oxide; that is, the cataloxidant comprises or consists essentially of Rh (0.05% to about 2% by weight) and cobalt oxide (in an amount ranging from about 10% to about 20% by weight).

Particularly preferred rhodium-based supported cataloxidants comprise, or alternatively, consist essentially of: (i) about 0.5%, 0.75% and 1.25% Rh by weight relative to total weight of the catalyst, about 15% nickel oxide by weight relative to total weight of the catalyst, about 1.5% manganese oxide by weight relative to total weight of the catalyst, and a zirconium oxide or titanium oxide support; or, (ii) about 0.5% Rh by weight, about 15% cobalt oxide by weight, and a zirconium oxide or titanium oxide support (preferably impregnated with potassium). (See, e.g., Example 1).

Aniline is prepared in a batch reactor with the preferred rhodium-based cataloxidant compositions by reacting benzene and ammonia with a R/C ratio of about 1:1, a $NH_3:C_6H_6$ ratio of about 3:1 or about 6:1, a temperature ranging from about 300° C. to about 360° C., a pressure ranging from about 200 bar to about 350 bar, and a residence (reaction) time of about 1 hour. A benzene conversion of about 5%, about 6%, about 10% or more is achieved, with greater than about 95% (i.e., about 98%) selectivity for aniline based on weight and relative to benzene. The rhodium-based cataloxidant can be oxidatively regenerated as described, and the benzene amination can be effected again with favorable performance characteristics (e.g., benzene conversion of about 5%, 10% or more and with about 98% selectivity for aniline, based on weight and relative to benzene after 5 reaction/regeneration cycles).

Rhodium-based cataloxidant reactions are particularly preferred at temperatures ranging from about 200° C. up to about 370° C., and most preferably at temperatures ranging from about 250° C. to about 350° C. Above about 350° C., ammonia decomposition becomes a more substantial concern with the rhodium-based cataloxidant. As noted below, however, the ammonia decomposition at such higher temperatures was mitigated with iridium-based cataloxidants. Based on preliminary scale-up studies, it appears that the absolute amount of rhodium-based cataloxidant can be reduced for larger-scale reactions relative to the loadings for smaller-scale reactions.

Hence, the rhodium-based cataloxidants appear to be particularly promising for commercial amination reactions.

Iridium Cataloxidants

Preferred iridium-based supported cataloxidants of the invention for batch operation comprise, or alternatively, consist essentially of Ir in an amount ranging from about 0.05% to about 2% by weight relative to total weight of the catalyst, nickel oxide in an amount ranging from about 10% to about 20% by weight relative to total weight of the catalyst, and manganese oxide in an amount ranging from about 0.5% to about 2% by weight relative to the total weight of the catalyst.

Particularly preferred iridium-based cataloxidants comprise, or alternatively, consist essentially of about 0.5% to about 1.25% Ir by weight relative to total weight of the catalyst, about 15% nickel oxide by weight relative to total weight of the catalyst, about 2% manganese oxide by weight relative to total weight of the catalyst, and a zirconium oxide support or a titanium oxide support (preferably impregnated with potassium). (See, e.g., Example 2).

Aniline is prepared with the preferred iridium-based cataloxidant compositions by reacting benzene and ammonia with a R/C ratio of about 1:1, a $NH_3:C_6H_6$ ratio of about 3:1, a temperature ranging from about 300° C. to about 500° C., a pressure ranging from about 200 bar to about 350 bar, and a residence (reaction) time of about 1 hour. A benzene conversion is about 5% is achieved with about 98% selectivity for aniline base on weight and relative to benzene. The iridium-based cataloxidant can be oxidatively regenerated as described, and the benzene amination can be effected again with favorable performance characteristics (e.g., benzene conversion of about 5% with about 98% selectivity for aniline based on weight and relative to benzene after 5 reaction/regeneration cycles).

Iridium-based cataloxidant reactions are particularly preferred at relatively higher temperatures, including temperatures ranging from about 325° C. up to about 400° C., and especially at temperatures ranging from about 340° C. to about 400° C. Ammonia decomposition at such higher temperatures is mitigated with the iridium-based cataloxidants relative to the rhodium-based cataloxidants.

Hence, the iridium-based cataloxidants also appear to be particularly promising for commercial amination reactions.

Palladium Cataloxidants

Preferred palladium-based supported cataloxidants of the invention for batch operation comprise, or alternatively, consist essentially of, Pd in an amount ranging from about 0.5% to about 4% by weight relative to total weight of the catalyst, nickel oxide in an amount ranging from about 20% to about 30% by weight relative to total weight of the catalyst, and manganese oxide in an amount ranging from about 10% to about 20% by weight relative to total weight of the catalyst.

Particularly preferred palladium-based cataloxidants comprise, or alternatively, consist essentially of, Pd in an amount ranging from about 1% to about 3% by weight relative to total weight of the catalyst, nickel oxide in an amount ranging from about 25% to about 30% weight relative to total weight of the catalyst, manganese oxide in an amount ranging from about 12% to about 18% by weight relative to total weight of the catalyst, and a zirconium oxide or titanium oxide support. (Example 3).

Aniline is prepared with the preferred palladium-based cataloxidant compositions by reacting benzene and ammonia substantially as described for the generally preferred case above. Benzene conversion is about 5.6% to about 6.3%, with about 94% selectivity for aniline based on weight and relative to benzene. The other major reaction product was diphenylamine (about 6% based on weight and relative to benzene). Palladium-based cataloxidant reactions are particularly preferred at relatively moderate temperatures, including temperatures ranging from about 300° C. up to about 350° C., and especially at temperatures ranging from about 310° C. to about 330° C.

Ruthenium Cataloxidants

Preferred ruthenium-based supported cataloxidants of the invention for batch operation comprise, or alternatively, consist essentially of Ru in an amount ranging from about 0.05% to about 5% by weight relative to total weight of the catalyst, and nickel oxide in an amount ranging from about 20% to about 30% by weight relative to total weight of the catalyst.

Particularly preferred ruthenium-based cataloxidants of the invention comprise, or alternatively, consist essentially of Ru in an amount ranging from about 0.5% to about 4% by weight relative to total weight of the catalyst, from about 25% to about 30% nickel oxide by weight relative to total weight of the catalyst, optionally from about 5% to about 10% manganese oxide, and a zirconium oxide or titanium oxide support. (Example 4).

Aniline is prepared with the preferred ruthenium-based cataloxidant compositions by reacting benzene and ammonia substantially as described for the generally preferred case above. Benzene conversion is about 3% with about 98% selectivity for aniline. Ruthenium-based cataloxidant reactions are particularly preferred at relatively moderate temperatures, including temperatures ranging from about 300° C. up to about 350° C., and especially at temperatures ranging from about 310° C. to about 330° C.

Platinum Cataloxidants

Preferred platinum-based supported cataloxidants of the invention for batch operation comprise, or alternatively, consist essentially of Pt in an amount ranging from about 0.05% to about 5% by weight relative to total weight of the catalyst, and nickel oxide in an amount ranging from about 20% to about 30% by weight relative to total weight of the catalyst.

Particularly preferred platinum-based cataloxidants of the invention comprise, or alternatively, consist essentially of Pt in an amount ranging from about 0.5% to about 2% by weight relative to total weight of the catalyst, from about 25% to about 30% nickel oxide by weight relative to total weight of the catalyst, optionally from about 15% to about 20% manganese oxide, and a zirconium oxide or titanium oxide support. (Example 5).

Aniline is prepared with the preferred platinum-based cataloxidant compositions by reacting benzene and ammonia substantially as described for the generally preferred case above. A benzene conversion is about 3% is achieved with about 98% selectivity for aniline based on weight and relative to benzene.

The following examples illustrate the principles and advantages of the invention.

EXAMPLES

Example 1

Preparation of Aniline with Rhodium-Based Cataloxidants

This example demonstrates the synthesis of a Rh/Ni-oxide/Mn-oxide/$ZrO_2$ catalyst (Example 1A), a Rh/Ni-oxide/$ZrO_2$ catalyst (Example 1B), a Rh/Ni-oxide/Mn-oxide/$KTiO_2$ catalyst (Example 1C), and a Rh/Co-oxide/$ZrO_2$ catalyst (Example 1D), as well as the use thereof for the direct amination of benzene to aniline. Effective regeneration of some of these rhodium-based catalyst is demonstrated below (See Example 6A through 6C).

Example 1A

Rh/Ni-oxide/Mn-oxide/$ZrO_2$

A Rh/Ni-oxide/Mn-oxide/$ZrO_2$ catalyst was prepared as follows. A zirconia support (1/8 inch pellets, surface area 54.1 $m^2/g$, pore volume 0.3 cc/g, Norton Chemical Process Products Corp., Product No. XT 16075) was pre-calcined at 110° C. for 1 hour. The zirconia support (30 g) was impregnated with an aqueous precursor solution comprising nickel nitrate, manganese nitrate and rhodium nitrate. The precursor solution was formed by combining $Ni(NO_3)_2.6H_2O$ (22.3 g), $Mn(NO_3)_2.x\ H_2O$(1.466 g), rhodium (III) nitrate solution (1.064 ml, 10% wt/wt Rh), and distilled water (I ml), and slowly warming to facilitate dissolution. When a clear solution was obtained, the pellets were impregnated with the solution in two steps with an intermediate drying step (100° C., 2–3 h), resulting in complete absorption of the precursor solution by the pellets. The impregnated pellets were then dried at 110° C. for 6 hours. The temperature of the oven was then raised to 450° C. in an interval of 4 hours, and the impregnated support material was calcined at this temperature for 4 hours. The catalyst yield was 34.67 g.

Direct amination of benzene in the presence of the Rh/Ni-oxide/Mn-oxide/$ZrO_2$ catalyst was then effected in a batch reactor. The 34.67 g catalyst (see above) was loaded into a dried and cleaned Parr bomb cylinder (94 ml volume). Liquid benzene (19.9 ml) was added. The Parr bomb was sealed with a head-piece equipped with a pressure indicator, safety valve and a manually operated valve for venting/loading with gases. The Parr bomb was then cooled by thermally equilibrating with liquid nitrogen. Ammonia gas (14.8 L) was condensed into the Parr bomb, with flow and total volume fed to the Parr bomb controlled by a mass-flow-controller (MFC). The reactant to catalyst ratio (R/C ratio) was about 1, and the ammonia to benzene ratio was about 3:1. The Parr bomb was mounted on a mechanical rocker. Electrical mantel-piece heaters (for the bottom, cylinder piece) and electrical ribbon-heaters (for the head piece) were connected. The device was thermally insulated with fiberglass mat. The Parr bomb was heated to 300° C., and benzene and ammonia were reacted over the catalyst at 300° C. and 300 bar for 4 hours. After the 4 hours reaction time was completed, the heaters were turned off and the Parr bomb was cooled to ambient temperature and then further cooled using dry ice. The cooled Parr bomb was vented to remove unreacted ammonia and other gases. The vented Parr bomb was then warmed to room temperature and opened, and the catalyst was separated from the solution by filtration over a ceramic frit. The catalyst on the frit was washed with ether (50 ml). The etheric filtrate solution was analyzed by gas chromatography (GC). The benzene conversion was determined to be 6.3% with about 100% aniline selectivity (based on weight and relative to benzene, as determined by calibrated GC analysis; 5.5% conversion prior to calibration)—i.e., no detectable amounts of byproducts were observed with GC.

Example 1B

Rh/Ni-oxide/ZrO$_2$

Stock solutions used for catalyst preparation were prepared as follows. A Ni(NO$_3$)$_2$ solution was prepared by dissolving Ni(NO$_3$)$_2$.6H$_2$O (97.3130 g) into water to make 500 ml solution (hereinafter referred to as the "Ni(NO$_3$)$_2$ Solution A"). A rhodium (III) solution was prepared by dissolving Rh(CH$_3$COCH=C(O)CH$_3$)$_3$ (4.0100 g) into acetic acid to make 200 m solution (hereinafter referred to as the "Rh(III) Solution").

A Rh/Ni-oxide/ZrO$_2$ catalyst was prepared as follows. Zr(OC$_3$H$_7$)$_4$/HOC$_3$H$_7$ (70 wt %, 8.300 ml) was mixed with 5.0 ml distilled water at room temperature while stirring. After hydrolysis, the sample was dried at 110° C. for 5 hours to form a support material. The Ni(NO$_3$)$_2$ Solution A (15.0 ml) was combined with the support material, and the mixture was stirred, and then dried at 110° C. for 5 hours. Acetic acid (10 ml) and the Rh(III) Solution (1.800ml) were then added. The sample was dried at 110° C. for 5 hours, and then calcined in air at 450° C. for 4 hours.

Direct amination of benzene in the presence of the Rh/Ni-oxide/ZrO$_2$ catalyst was then effected in a batch reactor. The reactor had two chambers defined along their common boundary by a piece of quartz paper. Aminating-agent precursors, (NH$_4$)$_2$CO$_3$ (0.2000 g) and CaO (1.4000 g) were loaded into a first chamber, and used to generate ammonia in situ under the reaction conditions described below. The catalyst (1.0000 g) and liquid benzene (1.000 ml) were loaded into the other chamber of the reactor. After the reactants were loaded, the reactor was sealed tight with a common gasket and a reactor head, and then heated from 22° C. to 350° C. over a period of 1 hour. Benzene was directly aminated with ammonia formed in situ from the aminating-agent precursors at 350° C., at about 200 bar, for 4 hours. After reaction, the reactor was cooled to room temperature, further cooled in a dry ice bath, and then opened for venting. The reactor contents were separated from the catalyst and analyzed by gas chromatography (GC). A benzene conversion of 4.7% was achieved with about 100% aniline selectivity based on weight and relative to benzene (as determined by GC).

Example 1C

Rh/Ni-oxide/Mn-oxide/KTiO$_2$

A Rh/Ni-oxide/Mn-oxide/KTiO$_2$ catalyst was prepared as follows. A titanium dioxide support (150 g; Degussa, P 25 S, surface area 45 m$^2$/g, pore volume 0.25cc/g) was initially calcined at 200° C. for 2 hours. It was then impregnated with an aqueous solution of KNO$_3$ (0.5% K solution; 1.939 g KNO$_3$ in 75 mls H$_2$O). The impregnated carrier was dried at 110° C. for 20 hours and then the oven temperature was increased to 550° C. over an interval of 8 hours. The carrier was then calcined for 4 hours at this temperature.

A portion of the resulting KTiO$_2$ carrier (50 g) was then impregnated with a first aqueous precursor solution comprising nickel nitrate, manganese nitrate and rhodium nitrate as follows. The first precursor solution was formed by combining Ni(NO$_3$)$_2$.6H$_2$O (37.16 g; 15% Ni), Mn(NO$_3$)$_2$.xH$_2$O (2.44 g), and a 10% (wt/wt) rhodium (III) nitrate solution (3.75 g; 1% Rh; Strem), the resulting solution being heated to about 70° C. to about 80° C. (with about 1 to 2 ml of H$_2$O being added initially as heating began). Once the contents of the first precursor solution were dissolved, the solution was maintained at about 60° C. to about 70° C. (to prevent Ni(NO$_3$)$_2$ from precipitating over the carrier surface), while about 50 g of the KTiO$_2$ carrier was added. In this preparation, the carrier absorbed essentially all of the first precursor solution.

Two additional portions of the KTiO$_2$ carrier (50 g each) were impregnated in a similar manner with a second and third aqueous precursor solution, respectively, both of which also comprised nickel nitrate, manganese nitrate and rhodium nitrate. More specifically, these precursor solutions were formed as described above, with the exception that they contained 5.0 g and 6.25 g, respectively, of the 10% (wt/wt) rhodium (III) nitrate solution.

Once each of the impregnated, potassium-doped carriers were prepared, they were dried at about 110° C. for approximately 20 hours. The oven temperature was then gradually increased to about 450° C. over a 12 hour interval, at which temperature they were calcined at 450° C. for 4 hours. The resulting catalysts each comprised 15% Ni, 1.5% Mn, 0.5% K, based on the total weight of the catalyst. Additionally, these catalysts contained 0.75%, 1.0% and 1.25% Rh, respectively, again based on the total weight of the catalyst.

Direct amination of benzene in the presence of third Rh/Ni-oxide/Mn-oxide/KTiO$_2$ catalyst (i.e., the catalyst containing 1.25% Rh) was then effected in a batch reactor, generally as described above (see, e.g., Example 1A). More specifically, initially benzene was directly aminated with ammonia (ammonia to benzene ratio of about 3), with this catalyst (reactant to catalyst ratio of about 1), at 300° C. for 2 hours at a pressure of 300 bar. The catalyst was recovered as previously described (see, e.g., Example 1A). The etheric filtrate solution was analyzed by GC. Benzene conversion was determined to be 10.4%, with nearly about 100% aniline selectivity (based on weight and relative to benzene).

Example 1D

Rh/Co-oxide/ZrO$_2$

A Rh/Co-oxide/ZrO$_2$ catalyst was prepared as follows. Cobalt nitrate (13.4 g, 99.999% cobalt nitrate) was dissolved in about 10 ml of H$_2$O. A portion of this solution (0.258 ml) was combined with 0.021 ml of an aqueous nitrate solution containing 10% (wt) rhodium. Zirconia pellets (Norton, XZ 16075, surface area 51 m$^2$/g, pore volume 0.3 cc/g), which had previously been dried at 250° C., were then impregnated with the resulting solution by treating the pellets with 0.155 ml portion of the solution, and then heating the impregnated pellets at 120° C. until they were dry. This process was repeated until all of the solution was consumed, at which point the impregnated pellets were dried for an additional 4 hours at 120° C. followed by calcining at 380° C. for 4 hours. After being cooled to about 25° C., the impregnated pellets (comprising about 0.5% Rh and about 14% Co by weight relative to the total weight of the cataloxidant) were lightly crushed using a mortar and pestle to produce a fine white powder.

Direct amination of benzene in the presence of the Rh/Co-oxide/ZrO$_2$ catalyst was then effected in a small batch reactor, similar to the process described in Example 1A. More specifically, to a scaled-down Parr bomb cylinder was added 0.065 g of the powdered catalyst. The reactor was cooled to 0° C. to add 0.106 ml of benzene, and then further cooled to −50° C. to add 0.070 mg of ammonia (ammonia to benzene ratio of about 4; reactant to catalyst ratio of about 1). The reactor was sealed and then the mixture was heated to about 300° C. to about 350° C. for about 2 hours at a reaction pressure of about 300 to about 400 bar. The reactor was cooled to −30° C., opened, and then slowly warmed to 10° C. to removed excess ammonia. Ether (0.3 ml) was added to dilute and/or dissolve the reaction products and then, after separation of the catalyst (see, e.g., Example 1A), the solution was analyzed by GC. A benzene conversion of 1.2% was achieved with an aniline selectivity of 89% (based on weight and relative to benzene).

Example 2

Preparation of Aniline with Iridium-Based Cataloxidants

This example demonstrates the synthesis of a Ir/Ni-oxide/Mn-oxide/ZrO$_2$ catalyst (Example 2A), a Ir/Ni-oxide/ZrO$_2$ catalyst (Example 2B) and a Ir/Ni-oxide/Mn-oxide/KTiO$_2$ catalyst (Example 2C), as well as the use thereof for the direct amination of benzene to aniline.

Example 2A

Ir/Ni-oxide/Mn-oxide/ZrO$_2$

A Ir/Ni-oxide/Mn-oxide/ZrO$_2$ catalyst was prepared in duplicate as follows from the following stock solutions: 2M Ni(NO$_3$)$_2$.6H$_2$O; 1M Mn(NO,)$_2$.6H$_2$O; Iridium(III) acetylacetonate (0.19 g in 12 ml of acetone).

A ZrO$_2$ carrier (15.0 g, surface area=52 m$^2$/g, pore volume 0.3 cc/g, Norton) was calcined in air at 250° C. for 2 h. A Ni—Mn solution was prepared by adding 4.09 ml of the 1 M Mn(NO$_3$)2 .6H$_2$O solution to 19.15 ml of the 2M Ni(NO$_3$)$_2$ solution. The pre-calcined Zro$_2$ support was immersed in the Ni—Mn solution (5 ml) and was then dried at 110° C. The dried, Ni—Mn impregnated carrier was subsequently immersed in 4 ml of the above-described Ir solution, and then dried at 110° C. Alternate immersion in the remaining amounts of the aforementioned Ni—Mn and Ir solutions, with intermittent drying, was continued until both solutions were consumed. Finally, both samples were calcined in air at 110° C. for 2 h and then additionally at 475° C. for 4 h.

Direct amination of benzene in the presence of the Ir/Ni-oxide/Mn-oxide/ZrO$_2$ catalyst was then effected in a Parr bomb batch reactor. Benzene (16.7 ml) was reacted with ammonia (NH$_3$:C$_6$H$_6$= 3:1) over the catalyst (R/C ratio=0.65) at 340° C., 300 bar, for 2 h in the Parr bomb. Benzene conversion was 5.7% with about 100% aniline selectivity (based on weight and relative to benzene, as determined by calibrated GC analysis; 5.0% conversion prior to calibration).

Example 2B

Ir/Ni-oxide/ZrO$_2$

Stock solutions used for catalyst preparation were prepared as follows. A Ni(NO$_3$)$_2$ Solution A was prepared as described in Example 1B. An iridium(III) solution was prepared by dissolving Ir(CH$_3$COCH—C(O)CH$_3$)$_3$ (1.2733 g) into acetic acid to make 100 ml solution (hereinafter referred to as the "Ir(III) Solution").

A Ir/Ni-oxide/ZrO$_2$ catalyst was prepared as follows. Zr(OC$_3$H$_7$)$_4$/HOC$_3$H$_7$ (70 wt %, 8.300 ml) was mixed with 5.0 ml distilled water at room temperature while stirring. After hydrolysis, the sample was dried at 110° C. for 5 hours to form a support material. The Ni(NO$_3$)$_2$ Solution A (15.0 ml) and the Ir(III) Solution (2.400 ml) were combined with the support material, and the mixture was stirred, dried at 110° C. for 10 hours, and then calcined in air at 450° C. for 4 hours.

Direct amination of benzene in the presence of the Ir/Ni-oxide/ZrO$_2$-catalyst was then effected as described in connection with Example 1B. A benzene conversion of 3.1% was achieved with about 100% aniline selectivity based on weight and relative to benzene (as determined by GC).

Example 2C

Ir/Ni-oxide/Mn-oxide/KTiO$_2$

A Ir/Ni-oxide/Mn-oxide/KTiO$_2$ catalyst was prepared as follows. A titanium dioxide support (150 g; Degussa, P 25 S, surface area 45 m$^2$/g, pore volume 0.25 cc/g) was initially calcined at 200° C. for about 2 hours. It was then impregnated with an aqueous solution of KNO$_3$ (0.5% K solution; 1.939 g KNO$_3$ in 75 mls H$_2$O). The impregnated carrier was dried at 110° C. for 20 hours and then the oven temperature was increased to 550° C. over an interval of 8 hours. The carrier was then calcined for 4 hours at this temperature.

A portion of the resulting KTiO$_2$ carrier (10 g) was pre-calcined at 200° C. for about 2 hours in an air oven. A solution of Ni-oxide/Mn-oxide (4.7 ml), prepared by dissolving 7.4 g of Ni(NO$_3$)$_2$ and 0.5 g of Mn(NO$_3$)$_2$.xH$_2$O in 15 ml of H$_2$O, was then added to the pre-calcined carrier and the resulting mixture was heated at 110° C. in air until dry. Once dried, about 4.7 ml of an iridium acetylacetonate solution (i.e., Ir-acac; prepared by combining 0.51 g of Ir-acac with 24 ml of acetone) was added to the carrier, and then it was dried again at 110° C. This sequential procedure was continued until all both of the solutions were consumed; that is, the carrier was repeated treated with one solution, dried, and then treated with the other until both the Ni-oxide/Mn-oxide and the Ir-acac solution were gone. However, when the final drying step was performed, the carrier was dried at 110° C. for 10 hours, and then the temperature was gradually increased to 450° C. over a 15 hour interval, at which temperature the carrier was calcined for 4 hours. The dried, impregnated carrier was then analyzed and found to comprise 2% Ir, 15% Ni, 1.5% Mn and 0.5% K, based on the total weight of the catalyst.

Direct amination of benzene in the presence of the Ir/Ni-oxide/Mn-oxide/KTiO$_2$ catalyst was then effected in a batch reactor, generally as described above (see, e.g., Example 2A). More specifically, initially benzene was directly aminated with ammonia (ammonia to benzene ratio of about 3; reactant to catalyst ratio of about 2.5), at 325° C. for 2 hours at a pressure of 300 bar. The catalyst was recovered as previously described (sec, e.g., Example 1A). The etheric filtrate solution was analyzed by GC. Benzene conversion was determined to be about 3.6%, with greater than about 95% aniline selectivity (based on weight and related to benzene).

Example 3

Preparation of Aniline with Palladium-Based Cataloxidants

This example demonstrates the synthesis of a number of Pd-based catalysts and the use thereof for the direct amination of benzene to aniline. The investigated catalysts include, specifically, a Pd/Ni-oxide/Mn-oxide/ZrO$_2$ catalyst (Example 3A), a Pd/Ni-oxide/Mn-oxide/La-oxide/ZrO$_2$ catalyst (Example 3B), a Pd/Ni-oxide/ZrO$_2$ catalyst (Example 3C), a Pd/Ni-oxide/La-oxide/ZrO$_2$ catalyst (Example 3D), a Pd/Ni-oxide catalyst (Example 3E), a Pd/Ni-oxide/Ce-oxide catalyst (Example 3F), a PdNi-oxide/Pr-oxide catalyst (Example 3G), a Pd/Ni-oxide/V-oxide catalyst (Example 3H), and a Pd/Ni-oxide/Mn-oxide catalyst (Example 3I). The catalysts are demonstrated to be effective as supported catalysts (Examples 3A through 3D) and/or as unsupported catalysts (Examples 3E through 3I).

Stock solutions used for catalyst preparation were prepared as follows. A Ni(NO$_3$)$_2$ Solution A was prepared as described in Example 1B. A palladium(II) solution was prepared by dissolving Pd(CH$_3$COCH=C(O)CH$_3$)$_2$ (2.86296 g) into acetic acid to make 200 ml solution (hereinafter referred to as the "Pd(II) Solution"). A Mn(NO$_3$)$_2$ solution was prepared by dissolving Mn (NO$_3$)$_2$.xH$_2$O (Aldrich, catalog No.28864-0) (94.0866 g) into distilled water to make 500 ml solution (hereinafter referred to as the "Mn(O$_3$)2 Solution B"). A La(NO$_3$)$_3$ solution was prepared by dissolving La(NO$_3$)$_3$.6H$_2$O (13.2901 g) in distilled water to make a 50 ml solution (hereinafter referred to as the "La(NO$_3$)$_3$ Solution"). A Ce(NO$_3$)$_3$ solution was prepared by dissolving Ce(NO$_3$)$_3$.6H$_2$O (6.3081 g) in distilled water to make a 50 ml solution (hereinafter referred to as the "Ce(NO$_3$)$_3$ Solution"). A Pr(NO$_3$)$_3$ solution was prepared by dissolving Pr(NO$_3$)$_3$.6H$_2$O (6.3880 g) in distilled water to make a 50 ml solution (hereinafter referred to as the "Pr(NO$_3$)$_3$ Solution"). A V$_2$O$_5$ solution was prepared by mixing V$_2$O$_5$ (10.0000 g) with oxalic acid dihydrate, adding 50 ml deionized water into the mixture, heating and stirring in water bath (about 80° C.) until a clear solution was formed. The clear solution was transferred to a 100 ml flask and, after cooling, deionized water was added to make a 100 ml solution (hereinafter referred to as the "V$_2$O$_5$ Solution").

Example 3A

Pd/Ni-oxide/Mn-oxide/ZrO$_2$

A Pd/Ni-oxide/Mn-oxide/ZrO$_2$ catalyst was prepared as follows. Zr(OC$_3$H$_7$)$_4$/HOC$_3$H$_7$ (70 wt %, 8.300 ml, Aldrich Cat. No. 33,397-2) was mixed with 4.0 ml distilled water at room temperature while stirring. After hydrolysis, the sample was dried at 110° C. for 5 hours to form a support material. The Ni(NO$_3$)$_2$ Solution A (15.0 ml) and the Mn(NO$_3$)$_2$ Solution B (7.200 ml) were combined with the support material, and the mixture was stirred and dried at 110° C. for 10 hours. After drying, the Pd(II) Solution (12.00 ml) was added to the Ni- and Mn-impregnated support, and the support was then dried at 110° C. for 5 hours, and then calcined in air at 480° C. for 4 hours.

Direct amination of benzene in the presence of the Pd/Ni-oxide/Mn-oxide/ZrO$_2$ catalyst was then effected as described in connection with Example 1B. A benzene conversion of 5.6% was achieved with about 94% aniline selectivity, and with about 6% diphenylamine selectivity, in each case based on weight and relative to benzene (as determined by GC).

Example 3B

PdNi-oxide/Mn-oxide/La-oxide/ZrO$_2$

A Pd/Ni-oxide/Mn-oxide/La-oxide/ZrO$_2$ catalyst was prepared as follows. Zr(OC$_3$H$_7$)HOC$_3$H$_7$ (70 wt %, 6.43 ml, Aldrich Cat. No. 33,397-2) was mixed with 4.0 ml distilled water at room temperature while stirring. After hydrolysis, the sample was dried at 110° C. for 5 hours to form a support material. The Ni(NO$_3$)$_2$ Solution A (15.0 ml), the Mn(NO$_3$)$_2$ Solution B (7.200 ml), and the La(NO$_3$)$_3$ Solution (1.500 ml) were combined with the support material, and the mixture was stirred and dried at 110° C. for 10 hours. After drying, the Pd(II) Solution (12.00 ml) was added to the Ni-, Mn-, and La-impregnated support, and the support was then dried at 110° C. for 5 hours, and then calcined in air at 480° C. for 4 hours.

Direct amination of benzene in the presence of the Pd/Ni-oxide/Mn-oxide/La-oxide/ZrO$_2$ catalyst was then effected as described in Example 1B. A benzene conversion of 4.8% was achieved with about 100% aniline selectivity based on weight and relative to benzene (as determined by GC).

Example 3C

Pd/Ni-oxide/ZrO$_2$

A Pd/Ni-oxide/ZrO$_2$ catalyst was prepared as follows. Zr(OC$_3$H$_7$)$_4$/HOC$_3$H$_7$ (70 wt %, 8.3 ml, Aldrich Cat. No. 33,397-2) was mixed with 5.0 ml distilled water at room temperature while stirring. After hydrolysis, the sample was dried at 110° C. for 5 hours to form a support material. The Ni(NO$_3$)$_2$ Solution A (15.0 ml) was combined with the support material, and the mixture was stirred and dried at 110° C. for 5 hours. After drying, the Pd(II) Solution (12.00 ml) was added to the Ni-impregnated support, and the support was then dried at 110° C. for 5 hours, and then calcined in air at 450° C. for 4 hours.

Direct amination of benzene in the presence of the Pd/Ni-oxide/ZrO$_2$ catalyst was then effected as described in Example 1B. A benzene conversion of 4.6% was achieved with about 100% aniline selectivity based on weight and relative to benzene (as determined by GC).

Example 3D

Pd/Ni-oxide/La-oxide/ZrO$_2$

A Pd/Ni-oxide/La-oxide/ZrO$_2$ catalyst was prepared as follows. Zr(OC$_3$H$_7$)$_4$/HOC$_3$H$_7$ (70 wt %, 6.43 ml, Aldrich Cat. No. 33,397-2) was mixed with 4.0 ml distilled water at room temperature while stirring. After hydrolysis, the sample was dried at 110° C. for 5 hours to form a support material. The Ni(NO$_3$)$_2$ Solution A (15.0 ml) and the La(NO$_3$)$_3$ Solution (0.900 ml) were combined with the support material, and the mixture was stirred and dried at 110° C. for 5 hours. After drying, the Pd(II) Solution (12.00 ml) was added to the Ni- and La-impregnated support, and the support was then dried at 110° C. for 5 hours, and then calcined in air at 450° C. for 4 hours.

Direct amination of benzene in the presence of the Pd/Ni-oxide/La-oxide/ZrO$_2$ catalyst was then effected as described in Example 1B. A benzene conversion of 4.8% was achieved with about 100% aniline selectivity based on weight and relative to benzene (as determined by GC).

Example 3E

Pd/Ni-oxide

A Pd/Ni-oxide catalyst was prepared as follows. The Ni(NO$_3$)$_2$ Solution A (60.0 ml) was mixed with poly(acrylic acid) (6.000 g, average M.W. 2000), dissolved in water, dried at 110° C. for 8 hours and then calcined in air at 400° C. for 4 hours to form a powdered Ni-oxide sample. The Pd(II) Solution (12.00 ml) was added to the Ni-oxide powder sample, and the Pd-impregnated sample was dried at for 4 hours, and then calcined in air at 400° C. for 4 hours.

Direct amination of benzene in the presence of the Pd/Ni-oxide catalyst was then effected as described in Example 1B, except that the reaction temperature was 360° C. (rather than 350° C.). A benzene conversion of 3.1% was achieved with about 100% aniline selectivity based on weight and relative to benzene (as determined by GC).

Example 3F

Pd/Ni-oxide/Ce-oxide

A Pd/Ni-oxide/Ce-oxide catalyst was prepared as follows. The Ni(NO$_3$)$_2$ Solution A (36.0 ml), the Ce(NO$_3$)$_3$ Solution (24.0 ml) and poly (acrylic acid) (6.000 g, average M.W. 2000) were dissolved in water. The aqueous solution was freeze-dried, and then calcined in air at 400° C. for 4 hours. The Pd(II) Solution (12.00 ml) was added to the freeze-dried sample, and the Pd-impregnated sample was dried at 110° C. for 4 hours, and then calcined in air at 450° C. for 4 hours.

Direct amination of benzene in the presence of the Pd/Ni-oxide/Ce-oxide catalyst was then effected as described in Example 1B, except that the reaction temperature was 360° C. (rather than 350° C.). A benzene conversion of 3.3% was achieved with about 100% aniline selectivity based on weight and relative to benzene (as determined by GC).

Example 3G

Pd/Ni-oxide/Pr-oxide

A Pd/Ni-oxide/Pr-oxide catalyst was prepared as follows. The Ni(NO$_3$)$_2$ Solution A (36.0 ml), the Pr(NO$_3$)$_3$ Solution (24.0 ml) and poly (acrylic acid) (6.000 g, average M.W. 2000) were dissolved in water. The aqueous solution was freeze-dried, and then calcined in air at 400° C. for 4 hours. The Pd(II) Solution (12.00 ml) was added to the freeze-dried sample, and the Pd-impregnated sample was dried at 110° C. for 4 hours, and then calcined in air at 450° C. for 4 hours.

Direct amination of benzene in the presence of the Pd/Ni-oxide/Pr-oxide catalyst was then effected as described in Example 1B, except that the reaction temperature was 360° C. (rather than 350° C.). A benzene conversion of 4.0% was achieved with about 100% aniline selectivity based on weight and relative to benzene (as determined by GC).

Example 3H

Pd/Ni-oxide/V-oxide

A Pd/Ni-oxide/V-oxide catalyst was prepared as follows. The Ni(NO$_2$)$_2$ Solution A (72.0 ml), the V$_2$O$_5$ Solution (24.0 ml) and poly (acrylic acid) (6.000 g, average M.W. 2000) were dissolved in water. The aqueous solution was freeze-dried, and then calcined in air at 400° C. for 4 hours. The Pd(II) Solution (12.00 ml) was added to the freeze-dried sample, and the Pd-impregnated sample was dried at 110° C. for 4 hours, and then calcined in air at 450° C. for 4 hours.

Direct amination of benzene in the presence of the Pd/Ni-oxide/V-oxide catalyst was then effected as described in Example 1B, except that the reaction temperature was 360° C. (rather than 350° C.). A benzene conversion of 3.8% was achieved with about 100% aniline selectivity based on weight and relative to benzene (as determined by GC).

Example 3I

Pd/Ni-oxide/Mn-oxide

A Pd/Ni-oxide/Mn-oxide catalyst was prepared as follows. The Ni(NO$_3$)$_2$ Solution A (36.0 ml), the Mn(NO$_3$)$_2$ Solution B (24.0 ml) and poly (acrylic acid) (6.000 g, average M.W. 2000) were dissolved in water. The aqueous solution was freeze-dried, and then calcined in air at 400° C. for 4 hours. The Pd(II) Solution (12.00 ml) was added to the freeze-dried sample, and the Pd-impregnated sample was dried at 110° C. for 4 hours, and then calcined in air at 480° C. for 4 hours.

Direct amination of benzene in the presence of the Pd/Ni-oxide/Mn-oxide catalyst was then effected as described in Example 1B, except that the reaction temperature was 360° C. (rather than 350° C.). A benzene conversion of 4.3% was achieved with about 94% aniline selectivity, and with about 6% diphenylamine selectivity, in each case based on weight and relative to benzene (as determined by GC).

Example 4

Preparation of Aniline with Ruthenium-Based Cataloxidants

This example demonstrates the synthesis of a Ru/Ni-oxide/Mn-oxide/ZrO$_2$ catalyst (Example 4A) and of a Ru/Ni-oxide/ZrO$_2$ catalyst (Example 4B), as well as the use thereof for the direct amination of benzene to aniline.

Stock solutions used for catalyst preparation were prepared as follows. A Ni(NO$_3$)$_2$ Solution A was prepared as described in Example 1B. A Mn(NO$_3$)$_2$ Solution B was prepared as described in Example 3. A ruthenium solution was prepared by dissolving Ru(NO)(NO$_3$)$_3$.xH$_2$O (Ru 31.96 wt %, 3.1280 g) into water to make 100 ml solution (hereinafter referred to as the "Ru Solution").

Example 4A

Ru/Ni-oxide/Mn-oxide/ZrO$_2$

A Ru/Ni-oxide/Mn-oxide/ZrO$_2$ catalyst was prepared as follows. Zr(OC$_3$H$_7$)$_4$/HOC$_3$H$_7$ (70 wt %, 7.53 ml, Aldrich Cat. No. 33,397-2) was mixed with 5.0 ml distilled water at room temperature while stirring. After hydrolysis, the sample was dried at 110° C. for 5 hours to form a support material. The Ni(NO$_3$)$_2$ Solution A (15.0 ml), the Mn(NO$_3$)$_2$ Solution B (2.400 ml), and the Ru Solution (6.000 ml) were combined with the support material, the mixture was stirred and dried at 110° C. for 10 hours, and then calcined in air at 480° C. for 4 hours.

Direct amination of benzene in the presence of the Ru/Ni-oxide/Mn-oxide/ZrO$_2$ catalyst was then effected as described in connection with Example 1B, except that the reaction temperature was 340° C. (rather than 350° C.). A benzene conversion of 2.7% was achieved with about 100% aniline selectivity based on weight and relative to benzene (as determined by GC).

Example 4B

Ru/Ni-oxide/ZrO$_2$

A Ru/Ni-oxide/ZrO$_2$ catalyst was prepared as follows. Zr(OC$_3$H$_7$)$_4$/HOC$_3$H$_7$ (70 wt %, 8.300 ml, Aldrich Cat. No. 33,397-2) was mixed with 5.0 ml distilled water at room temperature while stirring. After hydrolysis, the sample was dried at 110° C. for 5 hours to form a support material. The Ni(NO$_3$)$_2$ Solution A (1 5.0 ml) and the Ru Solution (1.800 ml) were combined with the support material, the mixture was stirred and dried at 110° C. for 10 hours, and then calcined in air at 450° C. for 4 hours.

Direct amination of benzene in the presence of the Ru/Ni-oxide/Mn-oxide/ZrO$_2$ catalyst was then effected as described in connection with Example 1B, except that the reaction temperature was 360° C. (rather than 350° C.). A benzene conversion of 2.5% was achieved with about 100% aniline selectivity based on weight and relative to benzene (as determined by GC).

Example 5

Preparation of Aniline with Platinum-Based Cataloxidants

This example demonstrates the synthesis of a Pt/Ni-oxide/ Mn-oxide/ZrO$_2$ catalyst (Example 5A) and of a Pt/Ni-oxide/ ZrO$_2$ catalyst (Example 5B), as well as the use thereof for the direct amination of benzene to aniline.

Stock solutions used for catalyst preparation were prepared as follows. A Ni(NO$_3$)$_2$ Solution A was prepared as described in Example 1B. A Mn(NO$_3$)$_2$ Solution B was prepared as described in Example 3. A platinum solution was prepared by dissolving Pt(CH$_3$COCH=C(O)CH$_3$)$_2$ (1.0081 g) into acetic acid to make a 100 ml solution (hereinafter referred to as the "Pt Solution").

Example 5A

Pt/Ni-oxide/Mn-oxide/ZrO$_2$

A Pt/Ni-oxide/Mn-oxide/ZrO$_2$ catalyst was prepared as follows. Zr(OC$_3$H$_7$)$_4$/HOC$_3$H$_7$ (70 wt %, 6.87 ml, Aldrich Cat. No. 33,397-2) was mixed with 5.0 ml distilled water at room temperature while stirring. After hydrolysis, the sample was dried at 110° C. for 5 hours to form a support material. The Ni(NO$_3$)$_2$ Solution A (15.0 ml), and the Mn(NO$_3$)$_2$ Solution B (6.000 ml) were combined with the support material, the mixture was stirred and dried at 110° C. for 5 hours, and then calcined in air at 450 C for 4 hours. The Pt Solution (3.000 ml) and acetic acid (12.0 ml) were added to the Ni- and Mn-impregnated sample, the sample was dried at 110° C. for 5 hours, and then calcined at 450° C. for 4 hours.

Direct amination of benzene in the presence of the Pt/Ni-oxide/Mn-oxide/ZrO$_2$ catalyst was then effected as described in connection with Example 1B, except that the reaction temperature was 360° C. (rather than 350° C.). A benzene conversion of 3.0% was achieved with about 100% aniline selectivity based on weight and relative to benzene (as determined by GC).

Example 5B

Pt/Ni-oxide/ZrO$_2$

A Pt/Ni-oxide/ZrO$_2$ catalyst was prepared as follows. Zr(OC$_3$H$_7$)$_4$/HOC$_3$H$_7$ (70 wt %, 8.300 ml, Aldrich Cat. No. 33,397-2) was mixed with 5.0 ml distilled water at room temperature while stirring. After hydrolysis, the sample was dried at 110OC for 5 hours to form a support material. The Ni(NO$_3$)$_2$ Solution A (15.0 ml was combined with the support material, the mixture was stirred and dried at 110° C. for 5 hours, and then calcined in air at 450° C. for 4 hours. The Pt Solution (3.000 ml) and acetic acid (12.0 ml) were added to the Ni- and Mn-impregnated sample, the sample was dried at 110° C. for 5 hours, and then calcined in air at 450° C. for 4 hours.

Direct amination of benzene in the presence of the Pt/Ni-oxide/ZrO$_2$ catalyst was then effected as described in connection with Example 1B, except that the reaction temperature was 360° C. (rather than 350° C.). A benzene conversion of 3.0% was achieved with about 100% aniline selectivity based on weight and relative to benzene (as determined by GC).

Example 6

Regenerable Noble Metal/Metal Oxide Catalysts for Aniline Preparation

This example demonstrates the effective regenerability of three Rh/Ni-oxide/Mn-oxide/ZrO$_2$ (6A–6C), one Rh/Ni-oxide/Mn-oxide/KTiO$_2$ (6D), one Rh/Co-oxideZrO$_2$ (6E), one Ir/Ni-oxide/Mn-oxide/KTiO$_2$ (6F), and two Ir/Ni-oxide/ Mn-oxide/ZrO$_2$ catalysts (6G). These examples illustrate, among other things, the effects of varying amounts of rhodium or iridium in the catalyst, the presence of Co as a reducible metal oxide, as well as the impact of different carriers.

Example 6A

Rh/Ni-oxide/Mn-Oxide/ZrO$_2$(3x-, 8x-Regenerated)

Catalyst comprising Rh (about 0.5%), Ni-oxide (about 15% Ni, assuming all of the Ni-oxide is in the Ni$^{+2}$ oxidation state) and Mn-oxide (about 1.5% Mn, assuming ½ of the Mn-oxide is in the Mn$^{+3}$ oxidation state and ½ of the Mn-oxide is in the Mn$^{+4}$ oxidation state) on ZrO$_2$ supports, with all percentages being by weight, relative to the weight of the support, were evaluated for regenerability as follows.

In one set of experiments, the Rh/Ni-oxide/Mn-oxide/ ZrO$_2$ catalyst of Example 1A was prepared, used in a first cycle of benzene amination and then recovered as described therein. The recovered catalyst was dried at 110° C. for 1 hour, and then regenerated by reoxidation in air in a calcination oven at 475° C. for 4 h. The one-time (1x) regenerated catalyst was subsequently reevaluated in the Parr bomb under the same conditions as outlined above, except that temperature was 325° C. (rather than 300° C.) and the reaction time was 2 hours (rather than 4 hours). Benzene conversion for the second amination reaction with the catalyst was determined to be 6.8% with about 100% selectivity for aniline (based on weight and relative to benzene, as determined by calibrated GC analysis; 5.9% conversion prior to calibration). The catalyst was regenerated a second and third time, in two additional regeneration experiments, and in each case the 2x- and 3x-regenerated catalyst was employed to effect the direct amination of benzene under the same conditions as in the 1x-regenerated case. A stable benzene conversion of about 5.3% was achieved in the two additional regeneration experiments, with about 100% selectivity to aniline (based on weight and relative to benzene, as determined by calibrated GC analysis; 4.6% conversion prior to calibration).

In a separate, independent set of experiments, a Rh/Ni-oxide/Mn-oxide/ZrO$_2$ catalyst was prepared, reacted and evaluated as described in Example 1A. The catalyst was recovered as described in Example 1A, dried at 110° C. for 1 hour, and then regenerated by reoxidation in air in a calcination oven at 475° C. for 4 h. The cycle of amination reactions and regeneration was repeated eight times. For each cycle, the amination reaction conditions were the same as that described in Example 1A, except for some variations in reaction temperature and reaction time as noted in Table 1, below. Likewise, the regeneration conditions were as described above, except for some variation in reoxidation (calcination) time as noted in Table 1, below.

As shown in Table 1, benzene conversion ranged from about 6.2% to about 5.5% (as determined by calibrated GC analysis; 5.4% and 4.8% conversion, respectively, prior to calibration) for the first eight reactions (i.e., for the original catalyst and the 1x-regenerated through 7x-regenerated catalysts), and from about 5.4% to about 4.1% when the ninth reaction (i.e., with the 8x-regenerated catalyst) is included. Moreover, good conversion was achieved with reaction times of 1 hour or less at a temperature of 350° C. In each case, the selectivity for aniline was about 100% selectivity based on weight and relative to benzene, as determined by GC.

TABLE 1

Regeneration of Rh/Ni-oxide/Mn-Oxide/ZrO$_2$ Catalyst

| Catalyst Cycle | Reaction Temperature | Reaction Time | Benzene Conversion calib./uncalib. | Regeneration Time |
|---|---|---|---|---|
| original catalyst | 300° C. | 4 hr | 5.7%/5.0% | 4 hr |
| 1X | 325° C. | 2 hr | 6.2%/5.4% | 4 hr |
| 2X | 340° C. | 2 hr | 5.6%/4.9% | 4 hr |
| 3X | 350° C. | 1 hr | 6.2%/5.4% | 4 hr |
| 4X | 350° C. | 1 hr | 6.1%/5.3% | 2 hr |
| 5X | 350° C. | 1 hr | 5.8%/5.1% | 1 hr |
| 6X | 350° C. | 45 min | 5.7%/5.0% | 1 hr |
| 7X | 350° C. | 30 min | 5.5%/4.8% | 2 hr |
| 8X | 350° C. | 30 min | 4.1%/4.1% | — |

Example 6B

Rh/Ni-oxide/Mn-Oxide/ZrO$_2$(10x-Regenerated)

Catalyst comprising Rh (about 3%), Ni-oxide (about 10% Ni, assuming all of the Ni-oxide is in the Ni$^{+2}$ oxidation state) and Mn-oxide (about 3% Mn, assuming ½ of the Mn-oxide is in the Mn$^{+3}$ oxidation state and ½ of the Mn-oxide is in the Mn$^{+4}$ oxidation state) on ZrO$_2$ supports, with all percentages being by weight, relative to the weight of the support, were evaluated. for regenerability as follows.

The Rh/Ni-oxide/Mn-oxide/ZrO$_2$ catalyst was prepared substantially as described in Example 1A, except that the amount of the support, and the relative amounts of the nickel nitrate, the manganese nitrate and the Rh(III) nitrate solution used to prepare the precursor solution were adjusted. Specifically, the catalyst composition was prepared as described from a zirconia support (22 g), and from a precursor solution formed from the combination of Ni(NO$_3$)$_2$.6H$_2$O (10.9 g), Mn(NO$_3$)$_2$.x H$_2$O (2.149 g), and rhodium(III) nitrate solution (4.68 ml, 10% wt/wt Rh).

Benzene was directly aminated with ammonia in an initial reaction, the catalyst was regenerated, and then the cycle of amination reactions and regeneration was repeated eleven times. In each reaction cycle, benzene was aminated over the catalyst with reaction conditions the same as that described in Example 1A (300° C., 4 hours, 300 bar, R/C ratio=0.83), except for some variation in the ammonia:benzene ratio, as noted in Table 2, below. In each regeneration cycle, the catalyst was recovered as described in Example 1A, dried at 110° C. for 1 hour, and then regenerated by reoxidation in air in a calcination oven at 475° C. for 4 h.

As shown in Table 2, benzene conversion ranged from about 3.3% to about 2.9% (as determined by calibrated GC analysis; 2.9% and 2.5% conversion, respectively, prior to calibration) for the first six reactions (i.e., for the original catalyst and the 1x-regenerated through 5x-regenerated catalysts). Benzene conversion ranged from about 3.7% to about 1.3% for the 6x-regenerated through the 11x-regenerated catalyst. In each case, the selectivity for aniline was about 100% selectivity based on weight and relative to benzene, as determined by GC.

TABLE 2

Regeneration of Rh/Ni-oxide/Mn-Oxide/ZrO$_2$ Catalyst

| Catalyst Cycle | Ammonia to Benzene Ratio | Benzene Conversion calib./uncalib. |
|---|---|---|
| original catalyst | 3:1 | 3.2%/2.8% |
| 1X | 3:1 | 3.3%/2.9% |
| 2X | 3:1 | 2.1%/1.8% |
| 3X | 3:1 | 2.9%/2.5% |
| 4X | 3:1 | 3.0%/2.6% |
| 5X | 3:1 | 3.0%/2.6% |
| 6X | 3:1 | 1.5%/1.3% |
| 7X | 6:1 | 4.2%/3.7% |
| 8X | 1:1 | 2.4%/2.1% |
| 9X | 10:1 | 3.3%/2.9% |
| 10X | 3:1 | 2.8%/2.4% |
| 11X | 4:1 | 2.8%/2.4% |

Example 6C

Rh/Ni-oxide/Mn-Oxide/ZrO$_2$(7x-Regenerated)

A catalyst comprising Rh (about 1%), Ni-oxide (about 15% Ni, assuming all of the Ni-oxide is in the Ni$^{+2}$ oxidation state) and Mn-oxide (about 1.5% Mn, assuming ½ of the Mn-oxide is in the Mn$^{+3}$ oxidation state and ½ of the Mn-oxide is in the Mn$^{+4}$ oxidation state) on ZrO$_2$ supports, with all percentages being by weight, relative to the weight of the support, was evaluated for regenerability as follows.

The Rh/Ni-oxide/Mn-oxide/ZrO$_2$ catalyst was prepared substantially as described in Example 1A, except that the relative amounts of the nickel nitrate, the manganese nitrate and the Rh(III) nitrate solution used to prepare the precursor solution were adjusted. Specifically, the catalyst composition was prepared as described from a zirconia support (30 g), and from a precursor solution formed from the combination of Ni(NO$_3$)$_2$.6H$_2$O (22.3 g), Mn(NO$_3$)$_2$.x H$_2$O (1.466 g), and rhodium(III) nitrate solution (2.128 ml, 10% wt/wt Rh).

Benzene was directly aminated with ammonia in an initial reaction, the catalyst was regenerated, and then the cycle of amination reactions and regeneration was repeated eleven times. In each reaction cycle, benzene was aminated over the catalyst with reaction conditions the same as that described in Example 1A (300° C., 4 hours, 300 bar, R/C ratio=0.83), except for the amination reactions with the 6x-regenerated catalyst (300° C., 2hours) and with the 7x-regenerated catalyst (325° C., 2 hours). In each regeneration cycle, the catalyst was recovered as described in Example 1A, dried at 110° C. for 1 hour, and then regenerated by reoxidation in air in a calcination oven at 475° C. for 4 h.

As shown in Table 3, benzene conversion ranged from about 6.1% to about 4.6% (as determined by calibrated GC analysis; 5.3% and 4.0% conversion, respectively, prior GC to calibration) for the eight reactions (i.e., for the original catalyst and the 1x-regenerated through 7x-regenerated catalysts). The only conversion data less than 5.5% (4.8% prior to GC calibration) was that of the 6x-regenerated catalyst, which corresponds to a shorter reaction time (2 hours). The data from the 7x-regenerated catalyst demonstrates that this shorter reaction time can be acceptable if the temperature is raised (e.g., to 325° C.). In each case, the selectivity for aniline was about 100% selectivity based on weight and relative to benzene, as determined by GC.

TABLE 3

Regeneration of Rh/Ni-oxide/Mn-Oxide/ZrO₂ Catalyst

| Catalyst Cycle | Benzene Conversion calib./uncalib. |
| --- | --- |
| original catalyst | 5.8%/5.1% |
| 1X | 5.7%/5.0% |
| 2X | 6.1%/5.3% |
| 3X | 5.7%/5.0% |
| 4X | 6.0%/5.2% |
| 5X | 5.5%/4.8% |
| 6X | 4.6%/4.0% |
| 7X | 5.5%/4.8% |

Example 6D

Rh/Ni-oxide /Mn-oxide/KTiO₂(5×-Regenerated)

A catalyst comprising Rh (about 1.25%), Ni-oxide (about 15% Ni, assuming all of the Ni-oxide is in the $Ni^{+2}$ oxidation state), Mn-oxide (about 1.5% Mn, assuming ½ of the Mn-oxide is in the $Mn^{+3}$ oxidation state and ½ of the Mn-oxide is in the $Mn^{+4}$ oxidation state) on a KTiO₂ carrier or support, with all percentages being by weight, relative to the weight of the support, was evaluated for regenerability as follows.

The catalyst was prepared and initially utilized for the direct amination of benzene as described in Example 1C. After isolation, the catalyst was dried at 110° C. for 1 hour, and then regenerated by reoxidation in air in a calcination oven at 475° C. for about 1 hours. The one-time (1×) regenerated catalyst was subsequently reevaluated two times under similar reaction conditions. The catalyst was then isolated, regenerated and reevaluated 3 additional times using similar reaction conditions, the exception being that the ammonia to benzene ratio was increased to 6. The reactions conditions and results are summarized in Table 4, below.

TABLE 4

Regenerability of Rh/Ni-oxide/Mn-oxide/KTiO₂ Catalyst

| Catalyst Cycle | Pressure (bar) | Reaction Temp./Time | NH₃:C₆H₆ Ratio | Conversion (%) |
| --- | --- | --- | --- | --- |
| initial catalyst | 300 | 325° C./2 hr. | 6 | 10.4 |
| 1X | 300 | 325° C./2 hr. | 6 | 10.0 |
| 2X | 300 | 325° C./2 hr. | 6 | 10.2 |
| 3X | 300 | 325° C./2 hr. | 6 | 10.2 |
| 4X | 300 | 325° C./2 hr. | 6 | 10.3 |
| 5X | 300 | 325° C./2 hr. | 6 | 10.1 |

As the results from Table 4 indicate, use of the present catalyst enables benzene conversions in excess of 10% to consistently be obtained. Additionally, in each case, the aniline selectivity was greater than 95%.

Example 6E

Rh/Co-oxide/ZrO₂(2×-Regenerated)

A catalyst comprising Rh (about 0.5%) and Co-oxide (about 14% Co, assuming all of the Co-oxide is in the $Co^{+3}$ or $Co^{+4}$ oxidation state), on a ZrO₂ carrier or support, with all percentages being by weight, relative to the weight of the support, was evaluated for regenerability as follows.

The catalyst was prepared and initially utilized for the direct amination of benzene as described in Example 1D. The catalyst was isolated and regenerated as described in Example 1A; more specifically, the catalyst was isolated and then reoxidized by heating in air to 475° C. for 4 hours. The one-time (1×) regenerated catalyst was subsequently reevaluated under similar reaction conditions. The catalyst was then isolated, regenerated and reevaluated a third time using similar reaction conditions, the exception being that the catalyst was reoxidized by heating to 500° C. for 4 hours. The results are summarized in Table 5, below.

TABLE 5

Regeneration of Rh/Co-oxide/ZrO₂ Catalyst

| Catalyst Cycle | Conversion (%) | Selectivity (%) | Cat. Regeneration |
| --- | --- | --- | --- |
| initial catalyst | 1.2 | 89 | 475° C./4 hrs. |
| 1X | 1.3 | 86 | 500° C./4 hrs. |
| 2X | 1.3 | 99 | — |

As the results indicate, the Rh/Co-oxide/ZrO₂ catalyst affords greater selectivity when regenerated at 500° C. Additional experimentation (not reported here), was conducted which supported this conclusion.

Example 6F

Ir/Ni-oxide/Mn-oxide/KTiO₂(1×-Regenerated)

A catalyst comprising Ir (about 2%), Ni-oxide (about 15% Ni, assuming all of the Ni-oxide is in the $Ni^{+2}$ oxidation state), Mn-oxide (about 1.5% Mn, assuming ½ of the Mn-oxide is in the $Mn^{+3}$ oxidation state and ½ of the Mn-oxide is in the $Mn^{+4}$ oxidation state) on a KTiO₂ carrier or support, with all percentages being by weight, relative to the weight of the support, was evaluated for regenerability as follows.

The catalyst was prepared and initially utilized for the direct amination of benzene as described in Example 2C (reactant to catalyst ratio about 2.5). After isolation, the catalyst was dried at 110° C. for 1 hour, and then regenerated by reoxidation in air in a calcination oven at 475° C. for about 1 to about 4 hours. The one-time (1×) regenerated catalyst was subsequently reevaluated at 350° C. at a pressure of about 300 bar for 1 hour. The reaction conditions and results are summarized in Table 7, below.

TABLE 7

Regenerability of Ir/Ni-oxide/Mn-oxide/KTiO₂ Catalyst

| Catalyst Cycle | Pressure (bar) | Reaction Temp/Time | NH₃:C₆H₆ Ratio | Conversion (%) | Selectivity (%) |
| --- | --- | --- | --- | --- | --- |
| initial catalyst | 300 | 325° C./2 hr | 3 | 3.5 | >95% |
| 1X | 300 | 350° C./1 hr | 3 | 5.4 | >95% |

As the results in the table indicate, the conversion is dependent on the reaction temperature, the selectivity increasing when the reaction temperature increased from 235° C. to 350° C. In contrast, the selectivity for aniline remained essentially unaffected by the change in reaction temperature.

Example 6G

Ir/Ni-oxide/Mn-Oxide/ZrO₂(10×-Regenerated)

A catalyst comprising Ir (about 0.5%), Ni-oxide (about 18% Ni, assuming all of the Ni-oxide is in the $Ni^{+2}$ oxidation state), and Mn-oxide (about 1.5% Mn, assuming ½ of the Mn-oxide is in the $Mn^{+4}$ oxidation state) on a $ZrO_2$ support, with all percentages being by weight, relative to the weight of the support, prepared, reacted and evaluated similar to the procedure described in Example 2A. More specifically, the catalyst was initially reacted in accordance with Example 2A, but using a temperature of 300° C. and a reaction time of 4 hours. The catalyst was recovered as described in Example 1A, dried at 110° C. for 1 hour, and then regenerated by reoxidation in air in a calcination oven, typically at 475° C. for 4 hours. The cycle of amination reactions and regenerations was repeated 10 times, the precise conditions for each provided in Table 8, below.

TABLE 8

Regeneration of Ir/Ni-oxide/Mn-Oxide/$ZrO_2$ Catalyst

| Catalyst Cycle | Reaction Temperature | Reaction Time | Benzene Conversion | Regeneration |
|---|---|---|---|---|
| original catalyst | 300° C. | 4 hr | 3.1% | 475° C./4 hr |
| 1X | 325° C. | 2 hr | 4.1% | 475° C./4 hr |
| 2X | 340° C. | 2 hr | 5.2% | 475° C./4 hr |
| 3X | 350° C. | 1 hr | 3.8% | 475° C./4 hr |
| 4X | 350° C. | 2 hr | 5.3% | 475° C./4 hr |
| 5X | 340° C. | 3 hr | 5.3% | 475° C./4 hr |
| 6X | 350° C. | 2 hr | 5.3% | 475° C./4 hr |
| 7X | 350° C. | 2 hr | 5.2% | 475° C./4 hr |
| 8X | 350° C. | 2 hr | 5.3% | 475° C./4 hr |
| 9X | 350° C. | 2 hr | 4.9% | 475° C./1 hr |
| 10X | 350° C. | 2 hr | 4.9% | — |

As shown in Table 8, benzene conversion ranged from about 5.3% to about 3.1% over the entire reaction sequence, the latter being due to the lower reaction temperature employed in the initial reaction. Additionally, in each case, the selectivity for aniline was about 100%, based on weight and relative to benzene, as determined by GC analysis.

In a second experiment, a catalyst comprising Ir (about 0.5%), Ni-oxide (about 18% Ni, assuming all of the Ni-oxide is in the $Ni^{+2}$ oxidation state) and Mn-oxide (about 1.5% Mn, assuming ½ of the Mn-oxide is in the $Mn^{+4}$ oxidation state) on a $ZrO_2$ support, with all percentages being by weight, relative to the weight of the support, prepared, reacted and evaluated similar to the procedure described in Example 2A. More specifically, the catalyst was initially reacted in accordance with Example 2A, but using a temperature of 325° C. and a reaction time of 2 hours. The catalyst was recovered as described in Example 1A, dried at 110° C. for 1 hour, and then regenerated by reoxidation in air in a calcination oven, typically at 475° C. for 4 hours. The cycle of amination reactions and regenerations was repeated 10 times, the precise conditions for each provided in Table 9, below.

TABLE 9

Regeneration of Ir/Ni-oxide/Mn-Oxide/$ZrO_2$ Catalyst

| Catalyst Cycle | Reaction Temp. | Reaction Time | Benzene Conv. | $NH_3/C_6H_6$ Ratio | Re-ox. Conditions |
|---|---|---|---|---|---|
| initial catalyst | 325° C. | 2 hr. | 4.9% | 3.0 | 475° C./4 hr |
| 1X | 350° C. | 2 hr. | 5.6% | 3.0 | 475° C./4 hr |
| 2X | 350° C. | 2 hr. | 5.9% | 3.0 | 475° C./4 hr |
| 3X | 350° C. | 2 hr. | 6.3% | 3.0 | 475° C./2 hr |
| 4X | 350° C. | 2 hr. | 6.5% | 3.0 | 475° C./2 hr |
| 5X | 350° C. | 2 hr. | 6.2% | 3.0 | 475° C./2 hr |
| 6X | 350° C. | 2 hr. | 6.5% | 3.0 | 475° C./1 hr |
| 7X | 350° C. | 2 hr. | 6.3% | 3.0 | 475° C./2 hr |
| 8X | 350° C. | 2 hr. | 7.5% | 6.0 | 475° C./2 hr. |

TABLE 9-continued

Regeneration of Ir/Ni-oxide/Mn-Oxide/$ZrO_2$ Catalyst

| Catalyst Cycle | Reaction Temp. | Reaction Time | Benzene Conv. | $NH_3/C_6H_6$ Ratio | Re-ox. Conditions |
|---|---|---|---|---|---|
| 9X | 350° C. | 2 hr. | 7.8% | 9.0 | 475° C./2 hr. |
| 10X | 350° C. | 2 hr. | 7.0% | 4.5 | — |

As shown in Table 9, benzene conversion ranged from about 7.8% to about 4.9% over the entire reaction sequence, the latter being due to the lower reaction temperature employed in the initial reaction. Additionally, in each case, the selectivity for aniline was about 10.0%, based on weight and relative to benzene, as determined by GC analysis.

Example 7

Pressure Effects on Conversion/Selectivity using Rh-based Catalyst

A catalyst comprising Rh (about 0.5%), Ni-oxide (about 15% Ni, assuming all of the Ni-oxide is in the $Ni^{+2}$ oxidation state) and Mn-oxide (about 1.5% Mn, assuming ½ of the Mn-oxide is in the $Mn^{+4}$ oxidation state) on a $ZrO_2$ support, with all percentages being by weight and relative to the weight of the support, was evaluated for its performance upon recycle using different reaction pressures, in order to study the effects of pressure change on reaction conversion and selectivity.

The Rh/Ni-oxide/Mn-oxide/$ZrO_2$ catalysts were prepared substantially as described in Example 1 A. Benzene was directly aminated with ammonia in accordance with Example 1A (at a reaction pressure of 300 bar), and then recovered as described therein. The recovered catalyst was dried at 110° C. for 1 hour, and then regenerated by reoxidation in air in a calcination oven at 475° C. for 4 hours. The one-time (1x) regenerated catalyst was subsequently reevaluated in the Parr bomb under the same reaction conditions, except that the reaction pressure was changed (as further detailed in Table 10, below). This procedure was repeated until the catalyst had been regenerated and reevaluated 6 times, a total of 7 reactions being performed.

As shown in Table 10, for each of the seven experiment the pressure ranged from a low of 50 bar to a high of 300 bar. Benzene conversion ranged from 6.2% (at 300 bar) to 1.8% (at 50 bar), as determined by GC analysis, the conversion consistently decreasing as the pressure decreased. However, as the last experiment indicates (i.e., 6x), when the pressure was returned to 300 bar, the conversion improved significantly, actually exceeding the results of the initial experiment. Additionally, it can be seen that the selectivity for aniline remains near 100% at reaction pressures of about 200 bar or greater. However, as the reaction pressure falls below about 200 bar, the aniline selectivity decreases significantly, accompanied by a corresponding increase in the formation of toluene and/or diphenyl.

TABLE 10

Pressure Dependence Study using Rh/Ni-oxide/Mn-oxide/$ZrO_2$ Catalyst

| Catalyst Cycle | Pressure (bar) | Conversion (%) | Selectivity (%) | | |
|---|---|---|---|---|---|
| | | | Toluene | Aniline | Diphenyl |
| original | 300 | 5.7 | — | >98 | — |
| 1X | 250 | 4.6 | — | 98 | 2 |

TABLE 10-continued

Pressure Dependence Study using Rh/Ni-oxide/Mn-oxide/ZrO$_2$ Catalyst

| Catalyst Cycle | Pressure (bar) | Conversion (%) | Selectivity (%) | | |
|---|---|---|---|---|---|
| | | | Toluene | Aniline | Diphenyl |
| 2X | 200 | 2.8 | 1 | 96 | 3 |
| 3X | 150 | 2.0 | 13 | 74 | 13 |
| 4X | 100 | 3.0 | 45 | 45 | 10 |
| 5X | 50 | 1.8 | 80 | 3 | 17 |
| 6X | 300 | 6.2 | — | >98 | — |

In this regard it is to be noted that, in batch operation, ammonia partial pressures are preferably at least about 150 bar, and more preferably at least about 200 bar, in order to drive the reaction, avoid coking and production of toluene and/or diphenyl. However, in continuous operation, where the instantaneous ratio of catalyst to substrate is much higher than in batch mode, effective amination can be achieved at much lower total pressures (i.e., about 1 to about 50 bar).

Example 8

Effects of Reactant Ratio on Conversion/Selectivity using Rh-based and Ir-based Catalysts Catalysts comprising (i) Rh (about 0.5%), Ni-oxide (about 15% Ni, assuming all of the Ni-oxide is in the Ni$^{+2}$ oxidation state) and Mn-oxide (about 1.5% Mn, assuming ½ of the Mn-oxide is in the Mn$^{+4}$ oxidation state), and (ii) comprising Ir (about 0.5%), Ni-oxide (about 15% Ni, assuming all of the Ni-oxide is in the Ni$^{+2}$ oxidation state) and Mn-oxide (about 1.5% Mn, assuming ½ of the Mn-oxide is in the Mn$^{+4}$ oxidation state), both on a ZrO$_2$ support, with all percentages being by weight and relative to the weight of the support, were prepared and evaluated for their performance upon recycle using different reactant ratios, in order to investigate the effects of reactant ratio, and more specifically the ratio of ammonia to benzene, on reaction conversion and selectivity.

For the Ir/Ni-oxide/Mn-oxide/ZrO$_2$ catalyst, which was prepared substantially as described in Example 2A, the impact of varying reactant ratios was studied during the above-described regeneration studies (see Example 6G). More specifically, initially benzene was directly aminated with ammonia in accordance with Example 2A, and then recovered as described therein. The recovered catalyst was dried at 110° C. for 1 hour, and then regenerated by reoxidation in air in a calcination oven at 475° C. for 4 hours. The one-time (1×) regenerated catalyst was subsequently reevaluated in the Parr bomb under similar reaction conditions. The catalyst was regenerated and reevaluated 10 times, the final 4 of these experiments (i.e., 7× through 10×) being carried out using the same reaction conditions (350° C. for 2 hours), with the exception that the reactant ratio of ammonia to benzene was varied (as further detailed in Table 11, below).

As shown in Table 11, for each of the 4 experiments the ammonia to benzene ratio ranged from a low of 3 (catalyst cycle 7×) to a high of 9 (catalyst cycle 9×), while benzene conversion ranged from 6.3% (7×) to 7.8% (9×), as determined by GC analysis. The aniline selectivity for these reactions remained essentially the same, at about 100% (as determined by GC analysis.

TABLE 11

Effects of NH$_3$/C$_6$H$_6$ Ratio using Ir/Ni-oxide/Mn-oxide/ZrO$_2$ Catalyst

| Catalyst Cycle | NH$_3$:C$_6$H$_6$ Ratio | Conversion (%) |
|---|---|---|
| 7X | 3.0 | 6.3 |
| 8X | 6.0 | 7.5 |
| 9X | 9.0 | 7.8 |
| 10X | 4.5 | 7.0 |

Similarly, the Rh/Ni-oxide/Mn-oxide/ZrO$_2$ catalyst was prepared substantially as described in Example 1A. To study the impact of a change in the reactant ratio, initially benzene was directly aminated with ammonia in accordance with Example 1A, and then recovered as described therein. The recovered catalyst was dried at 110° C. for 1 hour, and then regenerated by reoxidation in air in a calcination oven at 475° C. for 4 hours. The one-time (1×) regenerated catalyst was subsequently reevaluated in the Parr bomb under similar reaction conditions. The catalyst was regenerated and reevaluated 8 times, the final 2 of these experiments (i.e., 7× and 8×) being carried out using the same reaction conditions (325° C. for 2 hours), with the exception that the reactant ratio of ammonia to benzene was varied. More specifically, the ratio was 3.0 for catalyst cycle 7×, while the ratio was increased to 6.0 for catalyst cycle 8×. The benzene conversion for these reactions was about 6.2% and 7.0%, respectively, as determined by GC analysis. The aniline selectivity for these reactions remained essentially the same, at about 100% (as determined by GC analysis.

In light of the detailed description of the invention and the examples presented above, it can be appreciated that the several objects of the invention are achieved.

The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention.

We claim:

1. A method for preparing aniline, the method comprising reacting benzene with ammonia in the presence of a heterogeneous catalyst, the catalyst comprising (1) a noble metal selected from the group consisting of Pd, Pt, Rh, Ir, Ru and Os, and (2) a reducible metal oxide, the benzene being reacted with ammonia in a reaction zone of a reactor without supplying an oxygen-containing gas to the reaction zone.

2. A method for preparing aniline, the method comprising
   (a) contacting a heterogeneous catalyst comprising a noble metal and a reducible metal oxide with benzene and ammonia in a reaction zone of a reactor to form aniline, an initial benzene conversion being achieved with at least about 90% selectivity for aniline based on weight and relative to benzene,
   (b) regenerating at least a portion of the catalyst contacted in step (a) by exposing the catalyst to oxidizing conditions,
   (c) repeating steps (a) and (b) at least four times for at least a portion of the catalyst to form an at least 5×-regenerated catalyst, and
   (d) contacting the at least 5×-regenerated catalyst with benzene and ammonia to form aniline, the benzene conversion being at least about 50% of the initial benzene conversion, with at least about 90% selectivity for aniline based on weight and relative to benzene.

3. The method of claim 2 wherein steps (a) and (b) are repeated at least nine times for at least a portion of the catalyst to form an at least 10×-regenerated catalyst, and the at least 10×-regenerated catalyst is contacted with benzene and ammonia to form aniline, the benzene conversion being at least about 50% of the initial benzene conversion, with at least about 90% selectivity for aniline.

4. The method of claim 2 wherein the catalyst is regenerated in the reaction zone of the reactor.

5. The method of claim 2 wherein at least a portion of the catalyst is regenerated in a space external to the reaction zone of the reactor.

6. The method of claim 2 wherein the reducible metal oxide is reduced during the formation of aniline in step (a), and the reduced metal oxide is oxidized during step (b).

7. The method of claim 2 wherein the catalyst comprises a noble metal selected from the group consisting of Pd, Pt, Rh, Ir and Ru.

8. The method of claim 2 wherein the noble metal is selected from the group consisting of Pd, Rh, Ir and Ru.

9. The method of claim 2 wherein the reducible metal oxide is an oxide of a metal selected from the group consisting of Ni, Mn, V, Ce, Tb, Pr, Te, Re, Co and Bi.

10. The method of claim 2 wherein the reducible metal oxide is an oxide of a metal selected from the group consisting of Ni, Mn, Ce and Co.

11. The method of claim 2 wherein the reducible metal oxide is an oxide of a metal selected from the group consisting of Ni and Mn.

12. The method of claim 2 wherein the noble metal is selected from the group consisting of Pd, Rh, Ir and Ru, and the reducible metal oxide is nickel oxide.

13. The method of claim 2 wherein the noble metal is selected from the group consisting of Pd, Rh, Ir and Ru, the reducible metal oxide is nickel oxide, and the catalyst further comprises a second metal oxide, the second metal oxide being an oxide of a metal selected from the group consisting of alkali metals, alkaline earth metals, rare earth metals and other selected metals, the other selected metals consisting of Ga, Al, Y, Co, Mo, Cr, Mn, Zn, In, Fe, Bi, Sb and V.

14. A method for preparing aniline, the method comprising
    (a) contacting a heterogeneous catalyst with benzene and ammonia in a reaction zone of a reactor to form aniline, the catalyst comprising a noble metal and a reducible metal oxide,
    (b) regenerating at least a portion of the contacted catalyst by exposing the catalyst to oxidizing conditions, and without exposing the catalyst to reducing conditions, and
    (c) repeating steps (a) and (b) at least four times for at least a portion of the catalyst.

15. A process for the preparation of aniline by reaction of benzene with ammonia under conditions effective for oxidation of by-product hydrogen comprising:
    introducing gaseous benzene, ammonia and oxygen into a fluidized bed gas/solid contact zone comprising a fluidized particulate catalyst suspended in a process gas stream flowing through said zone, said catalyst being active for promoting the amination of benzene to aniline, and being subject to reduction in a redox reaction with hydrogen gas produced as a by-product of reaction between benzene and ammonia and to reoxidation by redox reaction with molecular oxygen, said process gas stream comprising the gases introduced into said contact zone and reaction products produced therein;
    the point of introduction of oxygen into said fluidized bed contact zone being spaced upstream from the point of introduction of benzene into said contact zone with respect to the direction of process gas flow through said contact zone;
    the velocity of gas flow, the particle size and configuration of the suspended catalyst and the geometric configuration of said gas/liquid contact zone being such that said process gas flows through said contact zone substantially in plug flow while said suspended catalyst is substantially back-mixed therein.

16. A process as set forth in claim 15 wherein said point of introduction of oxygen is upstream both from said point of introduction of benzene and from said point of introduction of ammonia, a catalyst re-oxidation zone being defined by the region within said contact zone between the point of introduction of oxygen and the point most proximate thereto with respect to the flow of process gas at which either ammonia or benzene is introduced, and an amination reaction zone being defined by the region within said contact zone downstream of said re-oxidation zone.

17. A process as set forth in claim 16 wherein benzene and ammonia are introduced at or near substantially the same point with respect to the flow of process gas within said contact zone.

18. A process as set forth in claim 16 wherein the molecular oxygen component of the process gas is substantially depleted by re-oxidation of said catalyst within said re-oxidation zone, so that the concentration of oxygen in the process gas entering said amination zone is less than about 1000 ppm, relative to the concentration of benzene.

19. A process as set forth in claim 18 wherein the concentration of oxygen is less than about 500 ppm, relative to the concentration of benzene.

20. A process as set forth in claim 19 wherein the concentration of oxygen is less than about 100 ppm, relative to the concentration of benzene.

21. A process as set forth in claim 16 wherein the conversion of benzene to aniline in said amination zone is at least about 5%.

22. A process as set forth in claim 16 wherein molecular hydrogen produced in said amination zone is substantially oxidized therein.

23. A process as set forth in claim 22 wherein hydrogen is substantially absent from the process gas exiting said amination zone.

24. A process as set forth in claim 15 wherein said catalyst comprises a metal which promotes the amination of benzene and a metal oxide which promotes the oxidation of hydrogen.

25. A process as set forth in claim 24 wherein nickel promotes the amination of benzene and nickel oxide promotes the oxidation of hydrogen.

26. A process as set forth in claim 24 wherein hydrogen by-product of the amination of benzene is consumed by reaction with the metal oxide component of said catalyst.

27. A process as set forth in claim 24 wherein the respective rates of introduction of oxygen, benzene and ammonia, the respective partial pressure gradients thereof within the gas/solid contact zone, the temperature range within said contact zone, the length to diameter ratio of said contact zone, and the residence time of process gas within said contact zone are such that the metal oxide component of said back-mixed particulate catalyst is maintained in a metastable partial oxidation state having an oxidation potential high enough to be effective for oxidation of hydrogen but low enough to avoid substantial oxidation of benzene, ammonia or aniline.

28. A process as set forth in claim 15 wherein said process gas further comprises a carrier gas effective to maintain stable plug flow of the process gas while maintaining the suspended particulate catalyst in a substantially back-mixed condition.

29. A process for the preparation of aniline by reaction of benzene with ammonia under conditions effective for oxidation of by-product hydrogen comprising:

introducing gaseous benzene, ammonia and oxygen into a process gas stream that flows through fluidized bed gas/solid contact zone comprising a fluidized particulate catalyst suspended in said process gas stream, said catalyst being active for promoting the amination of benzene to aniline, and being subject to reduction in a redox reaction with hydrogen gas produced as a by-product of reaction between benzene and ammonia and to reoxidation by redox reaction with molecular oxygen, said process gas stream comprising an inert carrier gas into which benzene, ammonia and oxygen are respectively introduced;

introduction of oxygen into said gas/solid contact zone into said process gas stream being temporally alternated with introduction of benzene and ammonia into said process gas stream so that molecular oxygen gas is substantially absent from said process gas in any region of the contact zone containing an excess of ammonia or benzene and ammonia with respect to oxygen, and benzene and ammonia are substantially absent from said process gas in any region of the gas/solid contact zone containing an excess of molecular oxygen gas with respect to benzene or ammonia;

the velocity of gas flow, the particle size and configuration of the suspended catalyst and the geometric configuration of said gas/liquid contact zone being such that said process gas flows through said contact zone substantially in plug flow while said suspended catalyst is substantially back-mixed therein.

30. A process as set forth in claim 29 wherein the concentration of molecular oxygen gas in regions containing an excess of benzene is less than about 1000 ppm, relative to the concentration of benzene therein.

31. A process as set forth in claim 30 wherein the concentration of molecular oxygen gas in regions containing an excess of benzene is less than about 500 ppm, relative to the concentration of benzene therein.

32. A process as set forth in claim 31 wherein the concentration of molecular oxygen gas in regions containing an excess of benzene is less than about 100 ppm, relative to the concentration of benzene therein.

33. A process as set forth in claim 29 wherein the introduction of pulses of benzene and ammonia are alternated with introduction of pulses of oxygen into said process gas stream.

34. A process as set forth in claim 33 wherein pulses of benzene and ammonia are substantially simultaneously introduced into said process gas stream.

35. A process as set forth in claim 33 wherein pulses of oxygen into said gas stream are sufficiently separated in time from pulses of benzene and ammonia so that regions of inert gas devoid of reactive species are established between regions containing benzene or ammonia in excess of molecular oxygen gas and regions containing molecular oxygen gas in excess of benzene and ammonia.

36. The method of claim 1 wherein the noble metal is selected from the group consisting of Pd, Rh, Ir and Ru, and the reducible metal oxide is selected from the group consisting of an oxide of Ni, Mn, Ce, Tb, Pr, Te, Re, Co, Fe, Cu, Bi and combinations thereof.

37. The method of claim 36 wherein the catalyst comprises a noble metal component and a reducible metal oxide, more than 50% of the noble metal component consisting essentially of one of the noble metals selected from the group consisting of Pd, Rh, Ir and Ru.

38. The method of claim 36 wherein the catalyst comprises a noble metal component and a reducible metal oxide, the noble metal component consisting essentially of one of the noble metals selected from the group consisting of Pd, Rh, Ir and Ru.

39. The method of claim 36 wherein the catalyst comprises Pd.

40. The method of claim 39 wherein the catalyst comprises a noble metal component and a reducible metal oxide, more than 50% of the noble metal component consisting essentially of Pd.

41. The method of claim 39 wherein the catalyst comprises a noble metal component and a reducible metal oxide, the noble metal component consisting essentially of Pd.

42. The method of claim 39 wherein the catalyst comprises Pd and oxides of two or more metals selected from the group consisting of Ni, Mn, Ce, Tb, Pr, Te, Re, Co, Fe, Cu and Bi.

43. The method of claim 39 wherein the catalyst comprises Pd and an oxide of a metal selected from the group consisting of Ni, Mn, Ce and Co.

44. The method of claim 39 wherein the catalyst comprises Pd and an oxide of a metal selected from the group consisting of Ni and Mn.

45. The method of claim 39 wherein the catalyst comprises Pd and nickel oxide.

46. The method of claim 39 wherein the catalyst comprises Pd and cobalt oxide.

47. The method of claim 36 wherein the catalyst comprises Rh.

48. The method of claim 47 wherein the catalyst comprises a noble metal component and a reducible metal oxide, more than 50% of the noble metal component consisting essentially of Rh.

49. The method of claim 47 wherein the catalyst comprises a noble metal component and a reducible metal oxide, the noble metal component consisting essentially of Rh.

50. The method of claim 47 wherein the catalyst comprises Rh and oxides of two or more metals selected from the group consisting of Ni, Mn, Ce, Tb, Pr, Te, Re, Co, Fe, Cu and Bi.

51. The method of claim 47 wherein the catalyst comprises Rh and an oxide of a metal selected from the group consisting of Ni, Mn, Ce and Co.

52. The method of claim 47 wherein the catalyst comprises Rh and an oxide of a metal selected from the group consisting of Ni and Mn.

53. The method of claim 47 wherein the catalyst comprises Rh and nickel oxide.

54. The method of claim 47 wherein the catalyst comprises Rh and cobalt oxide.

55. The method of claim 36 wherein the catalyst comprises Ir.

56. The method of claim 55 wherein the catalyst comprises a noble metal component and a reducible metal oxide, more than 50% of the noble metal component consisting essentially of Ir.

57. The method of claim 55 wherein the catalyst comprises a noble metal component and a reducible metal oxide, the noble metal component consisting essentially of Ir.

58. The method of claim 55 wherein the catalyst comprises Ir and oxides of two or more metals selected from the group consisting of Ni, Mn, Ce, Tb, Pr, Te, Re, Co, Fe, Cu and Bi.

59. The method of claim 55 wherein the catalyst comprises Ir and an oxide of a metal selected from the group consisting of Ni, Mn, Ce and Co.

60. The method of claim 55 wherein the catalyst comprises Ir and an oxide of a metal selected from the group consisting of Ni and Mn.

61. The method of claim 55 wherein the catalyst comprises Ir and nickel oxide.

62. The method of claim 55 wherein the catalyst comprises Ir and cobalt oxide.

63. The method of claim 36 wherein the catalyst comprises Ru.

64. The method of claim 63 wherein the catalyst comprises a noble metal component and a reducible metal oxide, more than 50% of the noble metal component consisting essentially of Ru.

65. The method of claim 63 wherein the catalyst comprises a noble metal component and a reducible metal oxide, the noble metal component consisting essentially of Ru.

66. The method of claim 63 wherein the catalyst comprises Ru and oxides of two or more metals selected from the group consisting of Ni, Mn, Ce, Tb, Pr, Te, Re, Co, Fe, Cu and Bi.

67. The method of claim 63 wherein the catalyst comprises Ru and an oxide of a metal selected from the group consisting of Ni, Mn, Ce and Co.

68. The method of claim 63 wherein the catalyst comprises Ru and an oxide of a metal selected from the group consisting of Ni and Mn.

69. The method of claim 63 wherein the catalyst comprises Ru and nickel oxide.

70. The method of claim 63 wherein the catalyst comprises Ru and cobalt oxide.

71. The method of claim 36 wherein the catalyst comprises an amount of the reducible metal oxide ranging from about 5% to about 99.95% by weight relative to the total weight of the catalyst.

72. The method of claim 36 wherein the catalyst further comprises a support, the catalyst comprises an amount of the noble metal ranging from about 0.01% to about 10% by weight relative to a total weight of the catalyst, and the catalyst comprises an amount of the reducible metal oxide ranging from about 5% to about 50% by weight relative to the total weight of the catalyst.

73. The method of claim 36 wherein the catalyst further comprises a support, the catalyst comprises an amount of the noble metal ranging from about 0.05% to about 5% by weight relative to a total weight of the catalyst, and the catalyst comprises an amount of the reducible metal oxide ranging from about 5% to about 30% by weight relative to the total weight of the catalyst.

74. The method of claim 36 wherein the catalyst further comprises a support, and the molar ratio of the noble metal to reducible metal oxide (NM:RMO) ranges from about 1:5,000 to about 1:2.

75. The method of claim 36 wherein the catalyst further comprises a support, and the molar ratio of the noble metal to reducible metal oxide (NM:RMO) ranges from about 1:1000 to about 1:3.

76. The method of claim 36 wherein the catalyst further comprises a support, and the catalyst comprises the noble metal in an amount ranging from about 0.01% to about 10% by weight relative to a total weight of the catalyst, and a reducible metal oxide formed by oxidation of a metal-oxide precursor, the metal-oxide precursor being present in an amount ranging from about 5% to about 50% by weight relative to the total weight of the catalyst.

77. The method of claim 36 wherein the catalyst further comprises a support.

78. The method of claim 77 wherein the catalyst further comprises a $ZrO_2$ support.

79. The method of claim 77 wherein the catalyst further comprises a $TiO_2$ support.

80. The method of claim 79 wherein the $TiO_2$ support is impregnated with an alkali metal oxide or an alkaline earth metal oxide, the concentration of the oxide ranging from about 0.1% to about 10%, relative to the total weight of the support.

81. The method of claim 80 wherein the $TiO_2$ support is impregnated with an oxide of potassium.

82. The method of claim 36 wherein the catalyst comprises an amount of the reducible metal oxide ranging from about 30% to about 90% by weight relative to the total weight of the catalyst.

83. The method of claim 82 wherein the catalyst further comprises a binder.

84. The method of claim 36 wherein a benzene conversion of not less than about 5% is achieved with at least about 90% selectivity for aniline, based on weight and relative to benzene.

85. The method of claim 1 wherein the catalyst additionally comprise a second metal oxide, the second metal oxide being an oxide of a metal selected from the group consisting of alkali metals, alkaline earth metals, rare earth metals and other selected metals, the other selected metals consisting of Ga, Al, Y, Co, Mo, Cr, Mn, Zn, In, Fe, Bi, and Sb.

86. The method of claim 85 wherein the second metal oxide is an oxide of an alkali metal.

87. The method of claim 85 wherein the second metal oxide is an oxide of an alkaline earth metal.

88. The method of claim 85 wherein the second metal oxide is an oxide of a rare earth metal.

89. The method of claim 85 wherein the second metal oxide is an oxide of a metal selected from the group consisting of Ga, Al, Y, Co, Mo, Cr, Mn, Zn, In, Fe, Bi, and Sb.

90. The method of claim 85 wherein the second metal oxide is an oxide of a metal selected from a group consisting of Ga, Al, Y, Co, Cr and Mn.

91. The method of claim 85 wherein the second metal oxide comprises two or more oxides of metals selected from the group consisting of Ga, Al, Y, Co, Mo, Cr, Mn, Zn, In, Fe, Bi, and Sb.

92. The method of claim 85 wherein the reducible metal oxide is an oxide of a metal selected from the group consisting of Ni, Mn, Ce, Tb, Pr, Te, Re, Co, Fe, Cu and Bi.

93. The method of claim 92 wherein the reducible metal oxide is an oxide of a metal selected from the group consisting of Ni, Mn, Ce and Co.

94. The method of claim 92 wherein the reducible metal oxide is an oxide of a metal selected from the group consisting of Ni, Mn, Ce, and Co, and the second metal oxide is an oxide of a metal selected from a group consisting of Ga, Al, Y, Co, Cr and Mn.

95. The method of claim 85 wherein the reducible metal oxide is an oxide of a metal selected from the group consisting of Ni, Mn, Ce, Tb, Pr, Te, Re, Co, Fe, Cu and Bi, the reducible metal oxide being present in an amount ranging from about 5% to about 50% by weight relative to total weight of the catalyst, and the second metal oxide is an oxide of a metal selected from a group consisting of Ga, Al, Y, Co, Cr and Mn, the second metal oxide being present in an amount ranging from about 0.1% to about 5% by weight relative to total weight of the catalyst.

96. The method of claim 85 wherein the catalyst further comprises a support, the molar ratio of the noble metal to the reducible metal oxide ranges from about 1:5,000 to about 1:2, and the molar ratio of the noble metal to the second metal oxide ranges from about 1:1000 to about 250:1.

97. The method of claim 85 wherein the catalyst further comprises a support, the molar ratio of the noble metal to the reducible metal oxide ranges from about 1:1000 to about 1:3, and the molar ratio of the noble metal to the second metal oxide ranges from about 1:200 to about 10:1.

98. The method of claim 85 wherein the catalyst further comprises a support, and the catalyst comprises (i) the noble metal in an amount ranging from about 0.01% to about 10% by weight relative to a total weight of the catalyst, (ii) a reducible metal oxide formed by oxidation of a first metal-oxide precursor, the first metal-oxide precursor being present in an amount ranging from about 5% to about 50% by weight relative to the total weight of the catalyst, and (iii) a second metal oxide formed by oxidation of a second metal-oxide precursor, the second metal-oxide precursor being present in an amount ranging from about 0.1% to about 5% by weight relative to the total weight of the catalyst.

99. The method of claim 85 wherein the noble metal is selected from the group consisting of Pd, Rh, Ir and Ru, the reducible metal oxide is an oxide of a metal selected from the group consisting of Ni and Mn, and the second metal oxide is an oxide of a metal selected from a group consisting of Ga, Al, Y, Co, Cr and Mn.

100. The method of claim 85 wherein the noble metal is selected from the group consisting of Pd, Rh, Ir and Ru, the noble metal is present in an amount ranging from about 0.05% to about 5% by weight relative to total weight of the catalyst, the reducible metal oxide is an oxide of a metal selected from the group consisting of Ni and Mn, the first metal oxide is present in an amount ranging from about 5% to about 50% by weight relative to total weight of the catalyst, the second metal oxide is an oxide of a metal selected from a group consisting of Ga, Al, Y, Co, Cr and Mn, and the second metal oxide is present in an amount ranging from about 0.1% to about 5% by weight relative to total weight of the catalyst.

101. The method of claim 1 wherein the catalyst comprises:
   a noble metal selected from the group consisting of Pd, Rh, Ir and Ru;
   nickel oxide; and,
   a support.

102. The method of claim 101 wherein the catalyst further comprises manganese oxide.

103. The method of claim 101 wherein the catalyst comprises:
   Pd in an amount ranging from about 0.5% to about 4% by weight relative to total weight of the catalyst;
   nickel oxide in an amount ranging from about 20% to about 30% by weight relative to total weight of the catalyst; and,
   manganese oxide in an amount ranging from about 10% to about 20% by weight relative to total weight of the catalyst.

104. The method of claim 101 wherein the catalyst comprises:
   Pd in an amount ranging from about 1% to about 3% by weight relative to total weight of the catalyst,
   nickel oxide in an amount ranging from about 25% to about 30% by weight relative to total weight of the catalyst,
   manganese oxide in an amount ranging from about 12% to about 18% by weight relative to total weight of the catalyst, and
   a zirconium oxide or titanium oxide support.

105. The method of claim 101 wherein the catalyst comprises:
   Rh in an amount ranging from about 0.05% to about 4% by weight relative to total weight of the catalyst;
   nickel oxide in an amount ranging from about 10% to about 20% by weight relative to total weight of the catalyst; and,
   manganese oxide in an amount ranging from about 0.5% to about 5% by weight relative to the total weight of the catalyst.

106. The method of claim 101 wherein the catalyst comprises:
   Rh in an amount ranging from about 0.1% to about 2% by weight relative to total weight of the catalyst;
   nickel oxide in an amount ranging from about 13% to about 17% by weight relative to total weight of the catalyst;
   manganese oxide in an amount ranging from about 0.5% to about 3% by weight; and,
   a zirconium oxide or titanium oxide support.

107. The method of claim 101 wherein the catalyst comprises:
   Ir in an amount ranging from about 0.05% to about 4% by weight relative to total weight of the catalyst;
   nickel oxide in an amount ranging from about 10% to about 20% by weight relative to total weight of the catalyst; and,
   manganese oxide in an amount ranging from about 0.5% to about 5% by weight relative to the total weight of the catalyst.

108. The method of claim 101 wherein the catalyst comprises:
   Ir in an amount ranging from about 0.1% to about 2% by weight relative to total weight of the catalyst;
   nickel oxide in an amount ranging from about 13% to about 17% by weight relative to total weight of the catalyst;
   manganese oxide in an amount ranging from about 0.5% to about 4% by weight relative to the total weight of the catalyst; and,
   a zirconium oxide or titanium oxide support.

109. The method of claim 101 wherein the catalyst comprises:
   Ru in an amount ranging from about 0.05% to about 5% by weight relative to total weight of the catalyst; and,
   nickel oxide in an amount ranging from about 20% to about 30% by weight relative to total weight of the catalyst.

110. The method of claim 101 wherein the catalyst comprises:
   Ru in an amount ranging from about 0.1% to about 4% by weight relative to total weight of the catalyst;

nickel oxide in an amount ranging from about 25% to about 30% by weight relative to total weight of the catalyst;

manganese oxide in an amount ranging from about 5% to about 10% by weight relative to the total weight of the catalyst; and, a zirconium oxide or titanium oxide support.

111. The method of claim 101 wherein the catalyst comprises:

Pd in an amount ranging from about 0.05% to about 4% by weight relative to total weight of the catalyst; and, nickel oxide in an amount ranging from about 20% to about 30% by weight relative to total weight of the catalyst.

112. The method of claim 101 wherein the catalyst comprises:

Pd in an amount ranging from about 0.1% to about 3% by weight relative to total weight of the catalyst;

nickel oxide in an amount ranging from about 25% to about 30% by weight relative to total weight of the catalyst;

manganese oxide in an amount ranging from about 15% to about 20% by weight relative to the total weight of the catalyst; and, a zirconium oxide or titanium oxide support.

113. The method of claim 101 wherein benzene is reacted with ammonia at a temperature ranging from about 200° C. to about 500° C.

114. The method of claim 101 wherein:

benzene is reacted with ammonia in a reaction zone of a reactor;

the molar ratio of ammonia to benzene supplied to the reaction zone ranges from about 0.5:1 to about 100:1;

the weight ratio of reactants to catalyst supplied to the reaction zone ranges from about 0.1:1 to about 20:1;

the temperature of the reaction zone ranges from about 200° C. to about 500° C. during the reaction; and the pressure of the reaction zone ranges from about 1 bar to about 500 bar during the reaction.

* * * * *